US010174341B2

(12) United States Patent
Glorioso, III et al.

(10) Patent No.: US 10,174,341 B2
(45) Date of Patent: Jan. 8, 2019

(54) NON-TOXIC HSV VECTORS FOR EFFICIENT GENE DELIVERY APPLICATIONS AND COMPLEMENTING CELLS FOR THEIR PRODUCTION

(71) Applicants: UNIVERSITY OF PITTSBURGH—OF THE COMMONWEALTH SYSTEM OF HIGHER EDUCATION, Pittsburgh, PA (US); Joseph C. Glorioso, III, Pittsburgh, PA (US); Justus Cohen, Pittsburgh, PA (US); Yoshitaka Miyagawa, Pittsburgh, PA (US); David Krisky, Sewickley, PA (US); James Wechuck, Glenshaw, PA (US); Darren Wolfe, Pittsburgh, PA (US)

(72) Inventors: Joseph C. Glorioso, III, Pittsburgh, PA (US); Justus Cohen, Pittsburgh, PA (US); Yoshitaka Miyagawa, Pittsburgh, PA (US); David Krisky, Sewickley, PA (US); James Wechuck, Glenshaw, PA (US); Darren Wolfe, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/905,708

(22) PCT Filed: Jul. 17, 2014

(86) PCT No.: PCT/US2014/047068
§ 371 (c)(1),
(2) Date: Jan. 15, 2016

(87) PCT Pub. No.: WO2015/009952
PCT Pub. Date: Jan. 22, 2015

(65) Prior Publication Data
US 2016/0153000 A1    Jun. 2, 2016

Related U.S. Application Data

(60) Provisional application No. 61/847,405, filed on Jul. 17, 2013.

(51) Int. Cl.
| | |
|---|---|
| *C12N 5/00* | (2006.01) |
| *C12N 15/86* | (2006.01) |
| *A61K 35/763* | (2015.01) |
| *A61K 48/00* | (2006.01) |
| *C12N 7/00* | (2006.01) |

(52) U.S. Cl.
CPC ............ *C12N 15/86* (2013.01); *A61K 35/763* (2013.01); *A61K 48/0066* (2013.01); *C12N 7/00* (2013.01); *C12N 2710/16621* (2013.01); *C12N 2710/16643* (2013.01); *C12N 2710/16671* (2013.01)

(58) Field of Classification Search
CPC .............................. C12N 15/86; A61K 35/763
See application file for complete search history.

(56) References Cited

U.S. PATENT DOCUMENTS

| | | | |
|---|---|---|---|
| 5,658,724 | A | 8/1997 | DeLuca |
| 5,804,413 | A | 9/1998 | DeLuca |
| 5,849,571 | A | 12/1998 | Glorioso et al. |
| 5,849,572 | A | 12/1998 | Glorioso et al. |
| 5,879,934 | A | 3/1999 | DeLuca |
| 5,998,174 | A | 12/1999 | Glorioso et al. |
| 6,261,552 | B1 | 7/2001 | DeLuca |
| 7,078,029 | B2 | 7/2006 | DeLuca |
| 7,531,167 | B2 | 5/2009 | Glorioso et al. |
| 2008/0008686 | A1 | 1/2008 | Yao |
| 2013/0096186 | A1 | 4/2013 | Glorioso, III et al. |

FOREIGN PATENT DOCUMENTS

| | | |
|---|---|---|
| JP | 2001-508294 A | 6/2001 |
| JP | 2003-518080 A | 6/2003 |
| WO | WO 98/15637 A1 | 4/1998 |

(Continued)

OTHER PUBLICATIONS

Samaniego et al. Journal of Virology 69(9):5707-5715, 1995.*

(Continued)

*Primary Examiner* — Marcia S Noble
(74) *Attorney, Agent, or Firm* — Leydig, Voit & Mayer, Ltd.

(57) ABSTRACT

The invention provides a herpes simplex virus (HSV) vector that does not express toxic HSV genes in non-complementing cells and which comprises a genome comprising one or more transgenes, wherein the vector is capable of expression of a transgene for at least 28 days in non-complementing cells. The disclosed vectors include vectors having deletions in the genes ICP0, ICP4, TCP22, TCP27 and TCP47, or alternative inactivating mutations, or vectors which express one or more of these genes with modified kinetics. The invention also relates to viral stocks of the inventive vectors, compositions thereof suitable for use therapeutically or for in vitro applications, and methods relating thereto. In another aspect, the invention provides a complementing cell, in particular a U2OS cell, engineered to express ICP4 and ICP27 when the cell is infected with HSV for the production of the inventive vector. Said cells are disclosed as naturally complementing ICP0.

13 Claims, 53 Drawing Sheets
Specification includes a Sequence Listing.

(56) References Cited

FOREIGN PATENT DOCUMENTS

| | | |
|---|---|---|
| WO | WO 99/06583 A1 | 2/1999 |
| WO | WO 01/46449 A1 | 6/2001 |

OTHER PUBLICATIONS

Mossman et al. Journal of Virology 74(4):2052-2056, 2000.*
Deluca and Schaffer. Nucleic Acids Research 15(11):4491-4511, 1987.*
Sacks et al. Journal of Virology 55(3):796-805, 1985.*
Akagi et al., *PNAS*, 100 (23): 13567-13572 (2003).
Amelio et al., "A Chromatin Insulator-Like Element in the Herpes Simplex Virus Type 1 Latency-Associated Transcript Region Binds CCCTC-Binding Factor and Displays Enhancer-Blocking and Silencing Activities," *Journal of Virology*, 80(5): 2358-2368 (Mar. 2006).
Anokye-Danso et al., "Highly Efficient miRNA-Mediated Reprogramming of Mouse and Human Somatic Cells to Pluripotency," *Cell Stem Cell*, 8: 376-388 (Apr. 8, 2011).
Antoniou et al., "Optimizing Retroviral Gene Expression for Effective Therapies," *Human Gene Therapy*, 24: 363-374 (Apr. 2013).
Australian Patent Office, International Search Report in International Patent Application No. PCT/US2014/047068 (dated Oct. 31, 2014).
Australian Patent Office, International Preliminary Report on Patentability in International Patent Application No. PCT/US2014/047068 (dated Jan. 19, 2016).
Baines et al., "The Open Reading Frames $U_L3$, $U_L4$, $U_L10$, and $U_L16$ Are Dispensable for the Replication of Herpes Simplex Virus 1 in Cell Culture," *Journal of Virology*, 65(2): 938-944 (Feb. 1991).
Berthomme et al., "Evidence for a Bidirectional Element Located Downstream from the Herpes Simplex Virus Type 1 Latency-Associated Promoter That Increases Its Activity during Latency," *Journal of Virology*, 74(8): 3613-3622 (Apr. 2000).
Bloom et al., "Epigenetic regulation of latent HSV-1 gene expression," *Biochimica et Biophysics Acta*, 1799: 246-256 (2010).
Chen et al., "Herpes Simplex Virus Type 1 ICP0 Protein Does Not Accumulate in the Nucleus of Primary Neurons in Culture," *Journal of Virology*, 74(21): 10132-10141 (Nov. 2000).
Craft et al., "Herpes Simplex Virus-Mediated Expression of Pax3 and MyoD in Embryoid Bodies Results in Lineage-Related Alterations in Gene Expression Profiles," *Stem Cells*, 26: 3119-3129 (2008).
Desai et al., "The RR1 Gene of Herpes Simplex Virus Type 1 Is Uniquely *trans* Activated by ICP0 during Infection," *Journal of Virology*, 67(10): 6125-6135 (Oct. 1993).
Dignam et al., "Accurate transcription initiation by RNA polymerase II in a soluble extract from isolated mammalian nuclei," *Nucleic Acids Research*, 11(5): 1475-1489 (1983).
Douville et al., "Positive and Negative Regulation at the Herpes Simplex Virus ICP4 and ICP0 TAATGARAT Motifs," *Virology*, 207: 107-116 (1995).
EMERY, "The Use of Chromatin Insulators to Improve the Expression and Safety of Integrating Gene Transfer Vectors," *Human Gene Therapy*, 22: 761-774 (Jun. 2011).
European Patent Office, Extended European Search Report in European Patent Application No. 14826236 (dated Mar. 22, 2017).
Gao et al., "BMP2 Is Superior to BMP4 for Promoting Human Muscle-Derived Stem Cell-Mediated Bone Regeneration in a Critical-Sized Calvarial Defect Model," *Cell Transplant.*, 22(12): 2393-2408 (2013).
Gierasch et al., "Construction and characterization of bacterial artificial chromosomes containing HSV-1 strains 17 and KOS," *Journal of Virological Methods*, 135: 197-206 (2006).
Goins et al., "A Novel Latency-Active Promoter Is Contained within the Herpes Simplex Virus Type 1 $U_L$ Flanking Repeats," *Journal of Virology*, 68(4): 2239-2252 (Apr. 1994).
Goins et al., "Herpes Simplex Virus Type 1 Vector-Mediated Expression of Nerve Growth Factor Protects Dorsal Root Ganglion Neurons from Peroxide Toxicity," *Journal of Virology*, 73(1): 519-532 (Jan. 1999).
Goldsmith et al., "Infected Cell Protein (ICP)47 Enhances Herpes Simplex Virus Neurovirulence by Blocking the $CD8^+T$ Cell Response," *J. Exp. Med.*, 187(3): 341-348 (Feb. 2, 1998).
GRANT, "Production and Purification of Highly Replication Defective HSV-1 Based Gene Therapy Vectors," *Doctoral Dissertation, University of Pittsburgh* (2008).
Harkness et al., "Transcription of the Herpes Simplex Virus 1 Genome during Productive and Quiescent Infection of Neuronal and Nonneuronal Cells," *Journal of Virology*, 88(12): 6847-6861 (Jun. 2014).
Hill et al., "Herpes simplex virus turns off the TAP to evade host immunity," *Nature*, 375: 411-415 (Jun. 1, 1995).
JIANG, "Development of an HSV-1 Gene Transfer Vector with Low Toxicity,".
Krisky et al., "Development of herpes simplex virus replication-defective multigene vectors for combination gene therapy applications," *Gene Therapy*, 5: 1517-1530 (1998).
Krisky et al., "Deletion of multiple immediate-early genes from herpes simplex virus reduces cytotoxicity and permits long-term gene expression in neurons," *Gene Therapy*, 5: 1593-1603 (1998).
Lilley et al., "Multiple Immediate-Early Gene-Deficient Herpes Simplex Virus Vectors Allowing Efficient Gene Delivery to Neurons in Culture and Widespread Gene Delivery to the Central Nervous System In Vivo," *Journal of Virology*, 75(9): 4343-4356 (May 2001).
Macdonald et al., "Genome Sequence of Herpes Simplex Virus 1 Strain KOS," *Journal of Virology*, 86(11): 6371-6372 (Jun. 2012).
Macdonald et al., "Genome Sequence of Herpes Simplex Virus 1 Strain McKrae," *Journal of Virology*, 86(17): 9540-9541 (Sep. 2012).
Makino et al., "Mesenchymal to embryonic incomplete transition of human cells by chimeric OCT4/3 (POU5F1) with physiological co-activator EWS," *Experimental Cell Research*, 315: 2727-2740 (2009).
Marconi et al., "Replication-defective herpes simplex virus vectors for gene transfer in vivo," *Proc. Natl. Acad. Sci. USA*, 93(21): 11319-11320 (Oct. 15, 1996).
McGeoch et al., "The Complete DNA Sequence of the Long Unique Region in the Genome of Herpes Simplex Virus Type 1," *J. Gen. Viral.*, 69: 1531-1574 (1988).
Menotti et al., "Substitution on the Murine Nectinl Receptor of a Single Conserved Amino Acid at a Position Distal from the Herpes Simplex Virus gD Binding Site Confers High-Affinity Binding to gD," *Journal of Virology*, 76(11): 5463-5471 (Jun. 2002).
Miyagawa et al., "EWS/ETS Regulates the Expression of the Dickkopf Family in Ewing Family Tumor Cells," *PLoS One*, 4(2): 1-12 (Feb. 2009).
Morimoto et al., "Identification of multiple sites suitable for insertion of foreign genes in herpes simplex virus genomes," *Microbiology and Immunology*, 53: 155-161 (2009).
Palmer et al., "Development and Optimization of Herpes Simplex Virus Vectors for Multiple Long-Term Gene Delivery to the Peripheral Nervous System," *Journal of Virology*, 74(12): 5604-5618 (Jun. 2000).
Pertel et al., "Cell Fusion Induced by Herpes Simplex Virus Glycoproteins gB, gD, and gH-gL Requires a gD Receptor but Not Necessary Heparan Sulfate," *Virology*, 279: 313-324 (2001).
Rajoáni et al., "Peculiarities of Herpes Simples Virus (HSV) Transcription: An overview," *Virus Genes*, 28(3): 293-310 (2004).
Rasty et al., "Deletion of the S component inverted repeat sequence ć and the nonessential genes $U_s1$ through $U_s5$ from the herpes simplex virus type 1 genome substantially impairs productive viral infection in cell culture and pathogenesis in the rat central nervous system," *Journal of NeuroVirology*, 3: 247-264 (1997).
Resnick et al. "DNA Binding by the Herpes Simplex Virus Type 1 ICP4 Protein Is Necessary for Efficient Down Regulation of the ICP0 Promoter," *Journal of Virology*, 63(3): 2497-2503 (Jun. 1989).
Samaniego et al., "The Herpes Simplex Virus Immediate-Early Protein ICP0 Affects Transcription from the Viral Genome and

(56) References Cited

OTHER PUBLICATIONS

Infected-Cell Survival in the Absence of ICP4 and ICP27," *Journal of Virology*, 71(6): 4614-4625 (Jun. 1997).
Samaniego et al., "Persistence and Expression of the Herpes Simplex Virus Genome in the Absence of Immediate-Early Proteins," *Journal of Virology*, 72(4): 3307-3320 (Apr. 1998).
Suzuki et al., "REAP: A two minute cell fractionation method," *BMC Research Notes*, 3(294): 1-6 (2010).
Takahashi et al., "Induction of Pluripotent Stem Cells from Mouse Embryonic and Adult Fibroblast Cultures by Defined Factors," *Cell*, 126: 663-676 (Aug. 25, 2006).
Takahashi et al., "Induction of Pluripotent Stem Cells from Adult Human Fibroblasts by Defined Factors," *Cell*, 131: 861-872 (Nov. 30, 2007).
Tischer et al., "Two-step Red-mediated recombination for versatile high-efficiency markerless DNA manipulation in *Escherichia coli,*" *Bio Techniques*, 40(2): 191-196 (2006).
Tischer et al., "*En Passant* Mutagenesis: A Two Step Markerless Red Recombination System," *Methods in Molecular Biology*, 634: 421-430 (2010).
Uchida et al. "Generation of Herpesvirus Entry Mediator (HVEM)-Restricted Herpes Simplex Virus Type 1 Mutant Viruses: Resistance of HVEM-Expressing Cells and Identification of Mutations That Rescue Nectin-1 Recognition," *Journal of Virology*, 83(7): 2951-2961 (Apr. 2009).
Uchida et al., "A Double Mutation in Glycoprotein gB Compensates for Ineffective gD-Dependent Initiation of Herpes Simplex Virus Type 1 Infection," *Journal of Virology*, 84(23): 12200-12209 (Dec. 2010).
Uchida et al., "Novel Mutations in gB and gH Circumvent the Requirement for Known gD Receptors in Herpes Simplex Virus 1 Entry and Cell-to-Cell Spread," *Journal of Virology*, 87(3): 1430-1442 (Feb. 2013).
Uchida et al., "Effective Treatment of an Orthotopic Xenograft Model of Human Glioblastoma Using an EGFR-retargeted Oncolytic Herpes Simplex Virus," *Molecular Therapy*, 21(3): 561-569 (Mar. 2013).
Ueki et al., "Hepatic B7 Homolog 1 Expression Is Essential for Controlling Cold Ischemia/Reperfusion Injury After Mouse Liver Transplantation," *Hepatology*, 54(1): 216-228 (Jul. 2011).
Watanabe et al., "Properties of a herpes simplex virus multiple immediate-early gene-deleted recombinant as a vaccine vector," *Virology*, 357: 186-198 (2007).
Wernig et al., "In vitro reprogramming of fibroblasts into a pluripotent ES-cell-like state," *Nature*, 448: 318-324 (Jul. 2007).
Wolfe et al. "A Herpes Simplex Virus Vector System for Expression of Complex Cellular cDNA Libraries," *Journal of Virology*, 84(14): 7360-7368 (Jul. 2010).
Yao et al. "An Activity Specified by the Osteosarcoma Line U2OS Can Substitute Functionally for ICP0, a Major Regulatory Protein of Herpes Simplex Virus Type 1," *Journal of Virology*, 69(10): 6249-6258 (Oct. 1995).
Yoshida et al., *Hepatology*, 58: 2163-2175 (2013).
Yu et al., "Induced Pluripotent Stem Cell Lines Derived from Human Somatic Cells," *Science*, 318: 1917-1920 (Dec. 21, 2007).
Yu et al., "Human Induced Pluripotent Stem Cells Free of Vector and Transgene Sequences," *Science*, 324: 797-801 (May 8, 2009).
Zwaagstra et al., *Virology*, 182: 287-297 (1991).
Amelio et al., "A Chromatin Insulator-Like Element in the Herpes Simplex Virus Type 1 Latency-Associated Transcript Region Binds CCCTC-Binding Factor and Displays Enhancer-Blocking and Silencing Activities,", *J. of Virology*, 80(5): 2358-2368 (Mar. 2006).
Lilley et al., "Multiple Immediate-Early Gene-Deficient Herpes Simplex Virus Vectors Allowing Efficient Gene Delivery to Neurons in Culture and Widespread Gene Delivery to the Central Nervous System In Vivo," *J. of Virology*, 75:9: 4343-4356 (May 2001).
Thomas et al., "Equine Herpesvirus 1 Gene 12 Can Substitute for vmw65 in the Growth of Herpes Simplex Virus (HSV) Type 1, Allowing the Generation of Optimized Cell Lines for the Propagation of HSV Vectors with Multiple Immediate-Early Gene Defects," *J. of Virology*, 73(9): 7399-7409 (Sep. 1999).
Japanese Patent Office, Office Action in Japanese Patent Application No. 2016-527106, 16 pp. (dated Jun. 5, 2018).
Chinese Intellectual Property Office, Office Action in Chinese Patent Application No. 2014800512737, 9 pp. (dated Aug. 31, 2018).
Jiang, "Development of an HSV-1 Gene Transfer Vector with Low Toxicity," Master's Thesis, Univ. of Pittsburgh, 68 pp. (Dec. 8, 2005).

* cited by examiner

FIG. 8

Underlined seq..... checked by sequencing

Lower case: plasmid derived, i.e. bacterial or linker

LAP1:-

CACGGCGGCCACCGCCGCCGCCGCCGACACCGCAGAGCCGGCGCGCGCACA
CACAAGCGGCAGAGGCAGAAAGGCCCCGAGTCATTGTTTATGTGGCCGCGGGCC
AGCAGACGGCCCGCGACACCCCCCCCGCCCGTGTGGGTATCCGGCCCCCCGCCC
CGCGCCGGTCCATTAAGGGCGCGCGTGCCCGCGAGATATCAATCCGTTAAGTGCT
CTGCAGACAGGGGCACCGCGCCCGGAAATCCATTAGGCCGCAGACGAGGAAAAT
AAAATTACATCACCTACCCATGTGGTGCTGTGGCCTGTTTTGCTGCGTCATCTGA
GCCTTTATAAAAGCGGGGGCGCGGCCGTGCC<u>GATCGC</u>CGGTGGTGCGAAAGACT
TTCCGGGCGCGTCCGGGTGCCGCGGCTCTCCGGGCCCCC (GATCGC =
LAT transcription start region)

LAP2:-

CCGGGGCGGCCAAGGGGCGTCGGCGACATCCTCCCCCTAAGCGCCGGCCGGCCG
CTGGTCTGTTTTTCGTTTTCCCCGTTTCGGGGGTGGTGGGGGTTGCCGGTTTCTGT
TTCTTTAACCCGTCTGGGGTGTTTTTCGTTCCGTCGCCGGAATGTTTCGTTCGTCT
GTCCCCTCACGGGGCGAAGGCCGCGTACGGCCCGGGACGAGGGGCCCCCGACCG
CGGCGGTCCGGGCCCCGTCCGGACCCGCTCGCCGGCACGCGACGCGAAAAAGGC
CCCCCGGAGGCTTTTCCGGGTTCCCGGCCCGGGGCCTGAGATGAACACTCGGGGT
TACCGCCAACGGCCGGCCCCCGTGGCGGCCCGGCCCGGGGCCCCGGCGGACCCA
AGGGGCCCCGGCCCGGGGCCCCACAACGGCCCGGCGCATGCGCTGTGGTTTTTTT
TTCCTCGGTGTTCTGCCGGGCTCCGTCGCCTTTCCTGTTCTCGCTTCTCCCCCCCC
CCTTCACCCCAGTACCCTCCTCCCTCCCTTCCTCCCCCGTTATCCCACTCGTCGA
GGGCGCCCCGGTGTCGTTCAACAAAGACGCCGCCGTTTCCAG

FIG. 8 (Continued)

LAT 2kb→

GTAGGTTAGACACCTGCTTCTCCCCAATAGAGGGGGGGGGACCCAAACGACAGG
GGGCGCCCCAGAGGCTAAGGTCGGCCACGCCACTCGCGGGTGGGCTCGTGTTAC
AGCACACCAGCCCGTTATTTTCCCCCCCTCCCACCCTTAGTTAGACTCTGTTACTT
ACCCGTCCGACCACCAACTGCCCCCTTATCTAAGGGCCGGCTGGAAGACCGCCA
GGGGGTCGGCCGGTGTCGCTGTAACCCCCCACGCCAATGACCCACGTACTCCAA
GAAGGCATGTGTCCCACCCCGCCTGTGTTTTGTGCCTGGCTCTCTATGCTTGGGT
CTTACTGCCTGGGGGGGGGAGTGCGGGGAGGGGGGGGGTGTGGAAGGAAAT
GCACGGCGCGTGTGTACCCCCCCTAAAGTTTGTCCTAAAGCGAGGATATGGAGG
AGTGGCGGGTGCCGGGGGACCGGGGTGATCTCTGGCACGCGGGGGTGGGAAGG
GTCGGGGGAGGGGGGGATGG░░░░░░GGCCCACCTGGCCGGCGCGGGTGCGCGT
GCCTTTGCACACCAACCCCACGTCCCCCGGCGGTCTCTAAGAAACACCGCCCCCC
CTCCTTCATACCACCGAGCATGCCTGGGTGTGGGTTGGTAACCAACACGCCCATC
CCCTCGTCTCCTGTGATTCTCTGGCTGCACCGCATTCTTGTTTTCTAACTATGTTCC
TGTTTCTGTCTCCCCCCCCACCCCTCCGCCCCACCCCCCAACAC░░░░░░░░░░

(5' recombination position; LAT P2 is defined as the PstI-BstXI fragment, i.e. LAP2 + the 5' portion of 2kb LAT)

ccatggttataaaaccctaggcctataactagttattaatagtaatcaattacggggtcattagttcatagcccatatatggagttcc (←
from CAG donor plasmid, bacterial sequence)

CAG promoter-

GCGTTACATAACTTACGGTAAATGGCCCGCCTGGCTGACCGCCCAACGACCCCCG
CCCATTGACGTCAATAATGACGTATGTTCCCATAGTAACGCCAATAGGGACTTTC
CATTGACGTCAATGGGTGGAGTATTTACGGTAAACTGCCCACTTGGCAGTACATC
AAGTGTATCATATGCCAAGTACGCCCCCTATTGACGTCAATGACGGTAAATGGCC
CGCCTGGCATTATGCCCAGTACATGACCTTATGGGACTTTCCTACTTGGCAGTAC
ATCTACGTATTAGTCATCGCTATTACCATGGTCGAGGTGAGCCCCACGTTCTGCTT
CACTCTCCCCATCTCCCCCCCCTCCCCACCCCCAATTTTGTATTTATTTATTTTTA
ATTATTTTGTGCAGCGATGGGGGCGGGGGGGGGGGGGAAAAAGCGAAGCGCG

FIG. 8 (Continued)

CGGCGGGCGGGAGTCGCTGCGCGCTGCCTTCGCCCCGTGCCCCGCTCCGCGCCGC
CTCGCGCCGCCCGCCCCGGCTCTGACTGACCGCGTTACTCCCACAGGTGAGCGGG
CGGGACGGCCCTTCTCCTCCGGGCTGTAATTAGCGCTTGGTTTAATGACGGCTTG
TTTCTTTTCTGTGGCTGCGTGAAAGCCTTGAGGGGCTCCGGGAGGGCCCTTTGTG
CGGGGGGAGCGGCTCGGGGGGTGCGTGCGTGTGTGTGCGTGGGGAGCGCCGC
GTGCGGCTCCGCGCTGCCCGGCGGCTGTGAGCGCTGCGGGCGCGGCGCGGGGCT
TTGTGCGCTCCGCAGTGTGCGCGAGGGGAGCGCGGCCGGGGCGGTGCCCCGCG
GTGCGGGGGGGCTGCGAGGGGAACAAAGGCTGCGTGCGGGGTGTGTGCGTGG
GGGGGTGAGCAGGGGGTGTGGGCGCGTCGGTCGGGCTGCAACCCCCCTGCACC
CCCCTCCCCGAGTTGCTGAGCACGGCCCGGCTTCGGGTGCGGGGCTCCGTACGGG
GCGTGGCGCGGGCTCGCCGTGCCGGGCGGGGGGTGGCGGCAGGTGGGGGTGCC
GGGCGGGCGGGGCCGCCTCGGCCGGGAGGGCTCGGGGGAGGGGCGCGGCG
GCCCCCGGAGCGCCGGCGGCTGTCGAGGCGCGGCGAGCCGCAGCCATTGCCTTT
TATGGTAATCGTGCGAGAGGGCGCAGGGACTTCCTTTGTCCCAAATCTGTGCGGA
GCCGAAATCTGGGAGGCGCCGCCGCACCCCTCTAGCGGGCGCGGGGCGAAGCG
GTGCGGCGCCGGCAGGAAGGAAATGGGCGGGGAGGGCCTTCGTGCGTCGCCGCG
CCGCCGTCCCCTTCTCCCTCTCCAGCCTCGGGGCTGTCCGCGGGGGGACGGCTGC
CTTCGGGGGGACGGGGCAGGGCGGGGTTCGGCTTCTGGCGTGTGACCGGCGGC
TCTAGAGCCTCTGCTAACCATGTTCATGCCTTCTTCTTTTCCTACAGCTCCTGGG
CAACGTGCTGGTTATTGTGCTGTCTCATCATTTTGGCAAAgaattcgagctcggtaccggtcgc
cacc

FIG. 8 (Continued)

EGFP coding-
ATGGTGAGCAAGGGCGAGGAGCTGTTCACCGGGGTGGTGCCCATCCTGGTCGAG
CTGGACGGCGACGTAAACGGCCACAAGTTCAGCGTGTCCGGCGAGGGCGAGGGC
GATGCCACCTACGGCAAGCTGACCCTGAAGTTCATCTGCACCACCGGCAAGCTGC
CCGTGCCCTGGCCCACCCTCGTGACCACCCTGACCTACGGCGTGCAGTGCTTCAG
CCGCTACCCCGACCACATGAAGCAGCACGACTTCTTCAAGTCCGCCATGCCCGAA
GGCTACGTCCAGGAGCGCACCATCTTCTTCAAGGACGACGGCAACTACAAGACC
CGCGCCGAGGTGAAGTTCGAGGGCGACACCCTGGTGAACCGCATCGAGCTGAAG
GGCATCGACTTCAAGGAGGACGGCAACATCCTGGGGCACAAGCTGGAGTACAAC
TACAACAGCCACAACGTCTATATCATGGCCGACAAGCAGAAGAACGGCATCAAG
GTGAACTTCAAGATCCGCCACAACATCGAGGACGGCAGCGTGCAGCTCGCCGAC
CACTACCAGCAGAACACCCCCATCGGCGACGGCCCCGTGCTGCTGCCCGACAAC
CACTACCTGAGCACCCAGTCCGCCCTGAGCAAAGACCCCAACGAGAAGCGCGAT
CACATGGTCCTGCTGGAGTTCGTGACCGCCGCCGGGATCACTCTCGGCATGGACG
AGCTGTACAAGTCCGGACTC*AGATCTTTTTCCCTCTGCCAAAAATTATGGGGACATCA*
*TGAAGCCCCTTGA* (←rabbit β-globin derived sequence (italics), provides GFP stop codon)
β-globin polyA region /signal (caps); lower case: plasmid-derived
GCATCTGACTTCTGGCTAATAAAGGAAATTTATTTTCATTGCAATAGTGTGTTGG
AATTTTTTGTGTCTCTCACTCGGAAGGACATATGGGAGGGCAAATCATTTAAAAC
ATCAGAATGAGTATTTGGTTTAGAGTTTGGCAACATATGCCCATATGCTGGCTGC
CATGAACAAAGGTTGGCTATAAAGAGGTCATCAGTATATGAAACAGCCCCCTGC
TGTCCATTCCTTATTCCATAGAAAAGCCTTGACTTGAGGTTAGATTTTTTTATAT
TTGTTTTGTGTTATTTTTTCTTTAACATCCCTAAAATTTTCCTTACATGTTTTACT
AGCCAGATTTTTCCTCCTCTCCTGACTACTCCCAGTCATAGCTGTCCCTCTTCTCTT
ATGGAGATCcctcgacctgcagcccaagcttggcgtaatcatggtcatagctgtttcctgtgaaattgtatccgctcacaatt
ccacacaacatacgagccggaagcataaagtgtaaagcctggggtgcctaatgagtgagctaactcacattaattgcgttgcgctcact
gcccgctttccagtcgggaaacctgtcgtgccagctgcattaatgaatcggccaacgcgcggggagaggcggtttgcgtattgggcgct
cttccgcttcctcgctcactgactcgctgcgctcggtcgttcggctgcggcgagcggtatcagctcactcaaaggcggtaatacggttat
ccacagaatcaggggataacgcaggaaagaacatgtgagcaaaaggccagcaaaaggccaggaaccgtaaaaaggccgcgttgctgg

FIG. 8 (Continued)

LAT resumes (3' recombination position)

TGCCAGTGGCAGGATGCTTTCGGGGATCGGTGGTCAGGCAGCCCGGGCCGCGGC
TCTGTG<mark>TTAAT</mark>ACCAGAGCCTGCCCAA CTRL2 insulator CATGGCACCCCACTCCCACGCACCCCACTCCCACGCACCCCACTCCCACGCA
CCCCACTCCCACGCACCCCACTCCCACGCACCCCACTCCCACGCACCCCAC
TCCCACGCACCCCACTCCCACGCACCCCACTCCCACGCACCCCACTCCCACG
CACCCCACTCCCACGCACCCCACTCCCACGCACCCCACTCCCACGCACCCCC
ACTCCCACGCACCCCACTCCCACGCACCCCGCGATACATCCAACACAGACAG
GAAAAGATACAAAAGTAAACC<mark>TTTATT</mark>TCCCAACAGACAGCAAAAATCCCCTG
AGTTTTTTTATTAGGGCCAACACAAAAGACCCGCTGGTG
TGTGGTGCCCGTGTCTTTCACTTTTCCCCTCCCCGACACGGATTGGCTGGTGTAGT
GGGCGCGGCCAGAGACCACCCAGCGCCCG← ICP0 mRNA end (opposite strand) with
<mark>polyA signal</mark>

End LAT sequence, LAT 2kb splice acceptor deleted, ICP0 coding and most of the 3'UTR
deleted, sequence picks up (opposite strand) with piece of ICP0 5'UTR followed by the TK
promoter originally driving ICP0 expression in JDβββ4 (βICP0):

caattggatatcGGGGCCCGCGGTACCGTCGACTGCAGAATTCGAAGCTTGAGCTCGAG
ATC
TGCGGCACGCTGTTGACGCTGTTAAGCGGGTCGCTGCAGGGTCGCTCGGTGTTCG
AGGCCACACGCGTCACCTTAATATGCGAAGTGGACCTGGGACCGCGCCGCCCCG
ACTGCATCTGCGTGTTCGAATTCGCCAATGACAAGACGCTGGGCGGGGTTTGTGT
CATCATAGAACTAAAGACATGCAAATATATTTCTT

B.

C.

A.

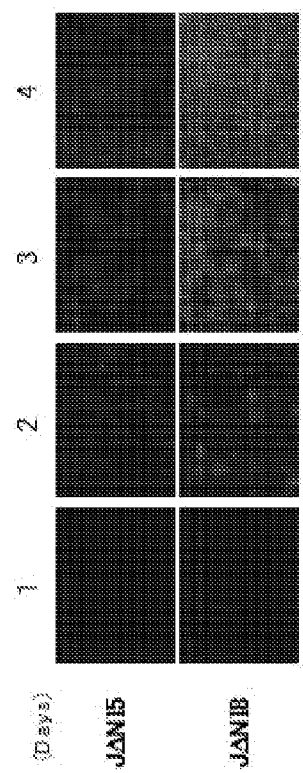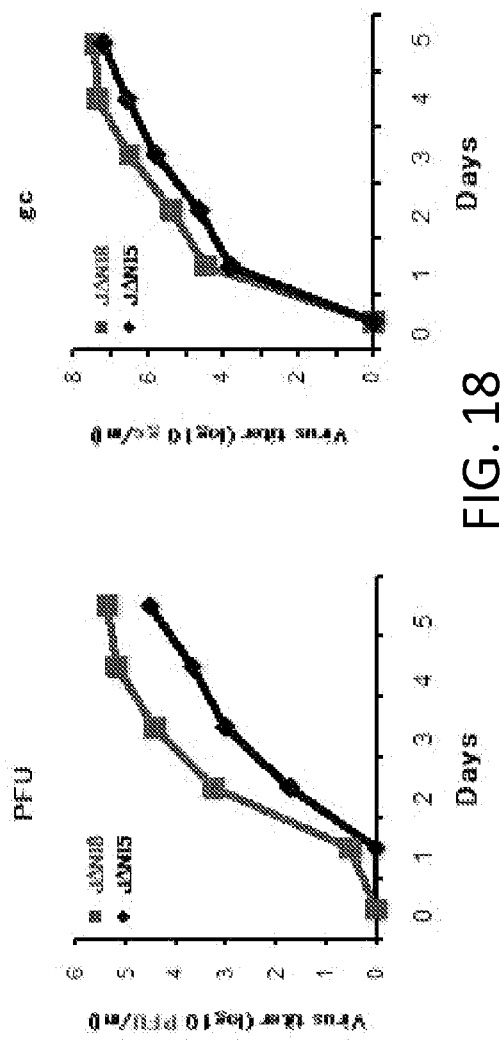
FIG. 18

NON-TOXIC HSV VECTORS FOR EFFICIENT GENE DELIVERY APPLICATIONS AND COMPLEMENTING CELLS FOR THEIR PRODUCTION

CROSS-REFERENCE TO RELATED APPLICATIONS

This application claims priority to U.S. Provisional Patent Application No. 61/847,405, filed Jul. 17, 2013, the entire contents of which are incorporated herein in their entirety.

STATEMENT REGARDING FEDERALLY SPONSORED RESEARCH AND DEVELOPMENT

This invention was made with Government support under Grant Numbers PO1DK044935 and 5RO1NS064988 awarded by the National Institutes of Health. The Government has certain rights in this invention.

BACKGROUND OF THE INVENTION

Among many viral and non-viral genetic vector systems, Herpes Simplex Virus (HSV)-based vectors have been investigated for use as gene transfer vectors, including for possible therapeutic use in human patients. HSV is a complex, non-integrating DNA virus capable of infecting a very wide range of human and animal cells. The viral genome contains more than 80 genes and is composed of two unique segments, $U_L$ and $U_S$, each flanked by inverted repeats that encode critical diploid genes. An important feature of HSV replication is the expression of its genes in waves referred to as cascade regulation (Rajcani, *Virus Genes*, 28: 293-310 (2004)). Removal of the essential immediate-early (IE) genes ICP27 and ICP4 renders the virus completely defective and incapable of expression of early (E) genes involved in viral genome replication and late (L) genes functioning in progeny virion assembly. These replication-defective viruses can be grown on complementing cells that express (complement) the missing ICP4 and ICP27 gene products and can then be used to infect non-complementing cells where the viral genome takes residence as a stable nuclear episome. However, vectors that preserve the ICP0 and ICP22 IE genes are toxic to cells, but inactivation or deletion of these genes, the ICP0 gene in particular, hampers transgene expression.

Accordingly, there remains a need for an HSV vector capable of expressing a transgene in any tissue or cell, in vitro or in vivo, without harming the cell or tissue and a system for propagating such vectors.

BRIEF SUMMARY OF THE INVENTION

The present invention relates to a breakthrough in HSV vector engineering that has provided the opportunity to express transgenes in a wide variety of tissues or cells (particularly mammalian), in vitro or in vivo, without expression of any harmful viral genes. The inventive HSV vector does not express any toxic viral genes in non-complementing cells, yet is capable of vigorous, persistent (e.g., for at least 14 days, such as at least 28 days, and preferably for at least 60 days) transgene expression. As such, it fills an extremely important niche in vector technology since HSV is the only vector that combines the capability of carrying large single- or multi-transgene expression cassettes controlled by general or cell-specific promoters with the property of highly efficient infection without vector integration. The inventive vector will allow efficient gene delivery to tissues, such as liver, for which no effective vector is currently available.

In one embodiment, the invention provides a herpes simplex virus (HSV) vector that does not express toxic HSV genes in non-complementing cells and which comprises a genome comprising one or more transgenes, wherein the vector is capable of expression of a transgene for at least 28 days in non-complementing cells. The inventive vector can comprise a transgene inserted in operable connection with one or more insulator sequences within the genome, wherein the vector does not express ICP0, ICP4, ICP22, ICP27, and ICP47 as immediate early genes. Depending on the activity of the promoter controlling the transgene, the inventive vector can express the transgene in any type of mammalian (especially human) cell that it can infect without the cytotoxicity associated with viral gene expression.

In another aspect, the invention provides a complementing cell for the production of the inventive vector. The inventive cell line is derived from 2OS cells, which have been engineered to express ICP4 and ICP27 when the cell is infected with HSV.

BRIEF DESCRIPTION OF THE DRAWINGS

FIG. 1A key: TR, terminal repeats; IR, internal repeats; UL, unique long region; US, unique short; numbers identify the location of the different IE genes; Δ, deletion; β, early promoter; CTRL, insulator; LAT P2, long-term expression element; CAG, CMV/actin/globin enhancer/promoter/intron cassette. FIG. 1B key: HDF, human dermal fibroblasts; hpi, hours post-infection; dpi, days post-infection; MOI, multiplicity of infection.

FIG. 2A shows GFP ("EGFP") and mCherry expression in HDF and U2OS cells infected at the indicated MOIs. Fluorescence microscopy images were acquired 3 days after infection. FIG. 2B shows the duration of transgene expression in infected HDF (MOI=0.5). Images were acquired at 1-14 days post-infection.

FIG. 4 key: Zeo, zeomycin-resistance gene; Cm, chloramphenicol-resistance gene; ccdB, toxin gene for negative selection; LATP2, LAT long-term expression element; CTRL2, chromatin boundary/insulator element 2 of the LAT locus.

FIG. 5 key: p, promoter; bla, blasticidin resistance gene.

FIG. 8 is the sequence of the LAT region of JΔN17-GFP vector of the present invention. This sequence is SEQ ID NO:1.

(FIG. 9A) Schematic representations of the wild-type HSV-1 KOS genome in KOS-37 BAC (24) and the genomes of the IE gene-deleted derivatives JΔNI2, JΔNI3 and JΔNI5. UL, unique long segment; US, unique short segment. Open boxes: terminal and internal inverted repeats. The BAC elements, including a chloramphenicol-resistance gene and β-galactosidase expression cassette, are located between loxP sites in the UL37-UL38 intergenic region (Gierasch et al., *J. Virol. Methods* 135, 197-206 (2006)). The US region in KOS-37 BAC and its derivatives is inverted compared to the standard representation of the HSV genome. Deletions in the JΔNI constructs are indicated by black boxes and the Δ symbol; the ICP47 promoter and translation initiation codon are removed as part of the joint deletion. IE genes converted to early expression kinetics by promoter replacement (ICP0, ICP27) or TAATGARAT deletion (ICP22) are represented by hatched boxes and the β symbol in front of the ICP number. All JΔNI recombinants contain the hyper-activating N/T mutations in the gB gene (Uchida et al., *J. Virol.* 84, 12200-09 (2010)) and a ubiquitin C promoter (UbCp)-mCherry cassette in the ICP4 locus; the SV40 polyA region of the mCherry cassette is represented by a small patterned box. (FIG. 9B) Western blot analysis of complementing cells. Uninfected cells and cells infected with QOZHG (left) or JΔNI5 virus (right) at an MOI of 1 were harvested at 24 hpi and extracts were prepared for gel electrophoresis. Blots were probed with antibodies for ICP4, ICP27, or α-tubulin as a loading control. (FIG. 9C) JΔNI2 and JΔNI5 virus growth in U2OS, U2OS-ICP4, U2OS-ICP4/27, and Vero-7b cells. Cells were infected at an MOI of 0.001 and extracellular virus was harvested daily from triplicate wells and titered on U2OS-ICP4/27 cells.

(FIG. 11A) In vitro cytotoxicity assay. HDFs and Vero cells were infected at 25,000 gc/cell and cell viability in triplicate wells was measured at 5 dpi by MTT assay. Plotted values represent the mean ratio of virus-infected to mock-infected cells. Brackets with asterisks indicate statistically significant differences ($p<0.05$) between JΔNI2- and JΔNI3-infected Vero cells and between JΔNI3- and JΔNI5-infected Vero cells. (FIG. 11B). Immunoblot analysis of IE gene products in HDFs. Cells were infected with KOS, QOZHG or JΔNI viruses at 1 PFU/cell and extracts were prepared at 24 hpi. Blots were probed with antibodies for the indicated IE gene products or α-tubulin as a loading control. (FIG. 11C) JΔNI IE gene expression measured by qRT-PCR. HDFs were infected with the indicated viruses at 1,000 gc/cell. mRNA was isolated at 12 hpi and reverse-transcribed for qPCR determination of the cDNA levels for the genes listed at the top. Expression was normalized to 18S rRNA levels and is shown relative to JΔNI2-infected cells. (FIG. 11D) qRT-PCR analysis for expression of early (upper panels) and late genes (lower panels). HDFs were infected and processed as in (FIG. 11C). ICP6 may be considered a delayed IE gene and is grouped with the early genes here as its expression is reportedly more dependent on ICP0 than on VP16 or ICP4 (Desai et al., *J. Virol.* 67, 6125-35 (1993); Sze et al., *Virus Res.* 26, 141-52 (1992); Harkness et al., *J. Virol.* 88(12) 6847-61 (2014)).

(FIG. 12A) mCherry fluorescence. Cells were infected at the indicated gc/cell and photographed at 24 hpi. (FIG. 12B) Relative mCherry mRNA levels. HDFs were infected at 5,000 gc/cell and harvested at 6 hpi for mRNA isolation, reverse transcription and qPCR as in FIG. 3C. (FIG. 12C) mCherry fluorescence in U2OS cells. Cells were infected at 1,000 gc/cell and photographed at 24 hpi. (FIG. 12D) Induction of mCherry expression in JΔNI5-infected HDFs. Cells were infected at the indicted gc/cell, superinfected at 24 h with QOZHG at 5,000 gc/cell, and photographed 24 h later.

(FIG. 13A) JΔNI7GFP contains a CAG promoter-EGFP expression cassette in the 2-kb LAT intron region between the LATP2 long-term expression/enhancer region and a downstream CTCF-binding motif (CTRL2) in the intron. LATP2 extends from the LAT transcription initiation site to within the 2-kb intron. JΔNI6GFP contains the same CAG promoter-EGFP expression cassette between the UL3 and UL4 genes. The rabbit β-globin polyA region of the CAGp-EGFP cassette is represented by a small patterned box. (B-D) EGFP and mCherry expression in infected HDFs. (FIG. 13B) Cells were infected with JΔNI6GFP or JΔNI7GFP virus at different gc/cell and fluorescence was visualized at 3 dpi. (FIG. 13C) HDFs were infected with JΔNI6GFP or JΔNI7GFP vector at 12,500 gc/cell and harvested 3 or 5 d later for mRNA extraction and qRT-PCR analysis for the 2 reporter genes. Expression normalized to 18S rRNA is shown relative to JΔNI6GFP-infected cells on day 3. (FIG. 13D) HDFs were infected with JΔNI6GFP or JΔNI7GFP virus at 25,000 gc/cell and EGFP fluorescence was photographed at 7, 14 and 28 dpi.

(FIG. 14A) Genome representations of JΔNI7GFP and derivatives deleted for CTRL1 (ΔC1), CTRL2 (ΔC2) or LATP2 (ΔLP2) individually or in combinations. The deletion of positions 8978-9161 in JQ673480 encompassed CTRL1, and a deletion of positions 5694-5857 in JQ673480 encompassed CTRL2. These deletions encompass a few bases beyond the CTCF binding motifs. (FIG. 14B) Reporter gene expressin in infected HDFs. Cells were infected with the indicated viruses at 12,500 gc/cell and fluorescence was recorded at 3 dpi. (FIG. 14C) Relative EGFP mRNA levels in HDFs infected with JΔNI7GFP, derivatives deleted for LAT elements, or JΔNI6GFP; viruses are identified by abbreviated names. Cells were infected at 12,500 gc/cell and processed at 3 dpi for qRT-PCR analysis. Expression levels were normalized to 18S rRNA and are presented relative to the level in JΔNI7GFP-infected cells.

(FIG. 15A) Construction of JΔNI9 and JΔNI10 vectors. An XhoI fragment encompassing CTRL1, LATP2 and CTRL2 was removed from the JΔNI5 genome and a GW recombination cassette was introduced between UL45 and UL46 to generate JΔNI9GW or between UL50 and UL51 to produce JΔNI10GW (upper). The same XhoI sites were used to isolate a CAGp-GFP-containing LAT fragment from JΔNI7GFP (lower left). The XhoI fragment was cloned into pENTR1A (lower right) and transferred into JΔNI9GW or JΔNI10GW by attL/attR recombination with the respective GW cassettes (LR reaction) to produce JΔNI9LAT-GFP and JΔNI10LAT-GFP, respectively. As controls, the CAGp-GFP cassette without LAT sequences was recombined via a pENTR1A intermediate into the GW locus of JΔNI9GW or JΔNI10GW, producing JΔNI9GFP and JΔNI10GFP. (FIG. 15B) Reporter gene expression in HDFs infected with JΔNI9 or JΔNI10 viruses. HDFs were infected with the indicated viruses at 12,500 gc/cell. EGFP and mCherry fluorescence were recorded at 3 dpi. (FIG. 15C) EGFP mRNA levels in infected HDFs determined by qRT-PCR as in earlier figures. Levels are shown relative to JΔNI9GFP- or JΔNI10GFP-infected cells. JΔNI10ΔC12LP2-GFP was constructed by transfer of the XhoI LAT fragment from JΔNI7ΔC12LP2-GFP into the GW site of JΔNI10GW similar to the construction of JΔNI10LAT-GFP above. (FIG. 15D) Effect of the deletion of both CTRLs and LATP2 from JΔNI10LAT-GFP on transgene expression. HDFs were infected at 12,500 gc/cell and EGFP and mCherry fluorescence were recorded at 3 dpi.

(FIG. 16A) The cells listed at the top were infected with JΔNI6GFP or JΔNI7GFP at the gc/cell indicated below the panels. EGFP and mCherry fluorescence were recorded at 3 dpi. (FIG. 16B) EGFP gene expression in cells infected as in (FIG. 16A) was measured at 3 dpi by qRT-PCR analysis. Results normalized to 18S rRNA are shown relative to JΔNI6GFP-infected cells. (FIG. 16C) hMDSCs were infected with JΔNI6GFP or JΔNI7GFP virus at 50,000 gc/cell and EGFP fluorescence was photographed at 14 and 28 dpi. (FIG. 16D) qRT-PCR determination of EGFP mRNA levels in hEK, hPAD and hHEP cells 3 d after infection with JΔNI10GFP or JΔNI10:LAT-GFP at 12,500 gc/cell. Normalized expression is shown relative JΔNI10GFP-infected cells.

FIG. 18 presents data concerning the growth of JΔNI8 relative to JΔNI5 in complementing cells (U2OS-ICP4/27) after infection at 1 genome copy (gc)/cell. The upper panel depicts reporter gene expression (mCherry), whereas the lower left panel reports virus yields in plaque forming units (PFU), and the lower right panel reports virus yields in genome copies (gc).

DETAILED DESCRIPTION OF THE INVENTION

The following patents and publications, which relate to various HSV vector technologies, are herein incorporated by reference. U.S. Pat. No. 5,658,724 relates to HSV strains deficient for ICP4 and ICP27 and methods for their production, growth, and use. U.S. Pat. No. 5,804,413 relates to a cell line comprising DNA encoding ICP4, ICP27, and ICP0. U.S. Pat. No. 5,849,571 relates to latency active herpes virus promoters and their use. U.S. Pat. No. 5,849,572 relates to a HSV-1 vector containing a LAT promoter. U.S. Pat. No. 5,879,934 relates to a recombinant HSV vector comprising genomic mutations within the ICP4 and ICP27 genes such that the ICP4 and ICP27 gene products are defective. U.S. Pat. No. 5,998,174 relates to methods of preparing a HSV vector. U.S. Pat. No. 6,261,552 relates to a HSV vector comprising a HSV genome having a deletion or mutation within a native TAATGARAT sequence, whereby said deletion or mutation causes the kinetics of expression of a native immediate early gene within said genome to be delayed when said genome is within a cell that contains HSV ICP4 gene products. U.S. Pat. No. 7,078,029 relates to HSV having a genome with a mutation of a TAATGARAT sequence such that, in the presence of a ICP4 gene product, a native immediate early gene is expressed from the genome with delayed kinetics. U.S. Pat. No. 7,531,167 relates to a HSV vector comprising deletions in only the ICP4, ICP27, and UL55 genes. U.S. Patent Application Publication No. 2013/0096186 relates to a HSV vector comprising a mutant gB and/or a mutant gH glycoprotein. International Patent Application Publication No. WO 1999/06583 relates to a HSV comprising an envelope including a non-native ligand.

Figure 32:
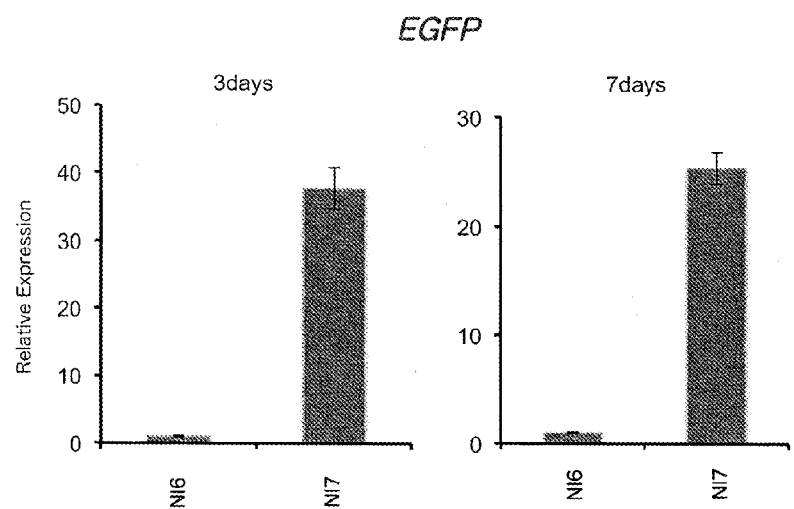
FIG. 32 presents data comparing EGFP mRNA levels between JΔNI7GFP- and JΔNI6GFP-infected HDF cells as determined by quantitative reverse transcription (RT)-PCR.

In one embodiment, the invention provides a herpes simplex virus (HSV) vector that does not express toxic native HSV genes in non-complementing cells and is capable of persistent expression of a transgene. For example, the inventive HSV vector can express a transgene for at least 14 days, such as at least 28 days, and preferably for at least 60 days, in cultured human dermal fibroblast (HDF) cells. Desirably, such expression of a transgene from the inventive vector occurs in the absence of measurable ICP0 gene product within such cells, such as the absence of any ICP0 gene product within such cells. In a particular embodiment, a vector according to the present invention having a transgene (e.g., encoding Enhanced Green Fluorescent Protein (EGFP) or another marker) inserted into the LAT region between the LAT P2 element and the CTRL2 element, and which has both CTRL1 and CTRL2, can express the transgene at least 20 (or at least about 20) times the level as can a vector having otherwise identical genetic mutations but in which such a transgene is inserted between $U_L3$ and $U_L4$, as determined by quantitative RT-PCR seven days post infection and at least 30 (or at least about 30) times the level as determined by quantitative RT-PCR three days post infection. See FIGS. 13 and 32. Such vector desirably expresses such transgene at such levels and for such period of time wherein the transgene is under the operable control of a CMV enhancer/chicken beta-actin promoter/chimeric intron. That such cells can be cultured for such periods having been infected with the inventive HSV vector also is evidence that the vector is not toxic to such cells (that is, not expressing toxic native HSV genes within the cells). Of course, the non-complementing cell(s) can be another cell type as well, and can be a cell in vivo, which is of interest for therapeutic applications.

For example, the inventive HSV vector can comprise a genome comprising a transgene inserted (a) within a latency-associated transcript (LAT) gene region, (b) within an ICP4 locus (and preferably only one, where the joint is deleted, as discussed herein) and/or (c) within the genome of the vector in operable connection with one or more insulator sequences within the genome. Preferably, the vector does not express ICP0, ICP4, ICP22, ICP27, and ICP47 as immediate early genes (although in some embodiments, expression of ICP47 may be desired). Without wishing to be bound by theory, it is believed that, depending on the activity of the promoter within the transgene, the inventive vector can express the transgene in any type of mammalian (especially human) cell that it can infect without the cytotoxicity associated with viral gene expression. The inventive vector can be present as isolated DNA, DNA within a cell, or packaged in a viral envelope.

Any suitable method can be employed to render the inventive vector incapable of expressing ICP0, ICP4, ICP22, ICP27, and ICP47 as immediate early genes within non-complementing cells. For example, the genome of the inventive vector can be engineered to comprise inactivating mutations (e.g., deletions) of one or all of these genes (e.g., deletions within or of the entire coding sequence of one or more of the ICP0, ICP4, ICP22, ICP27, and ICP4? genes (preferably comprising inactivating deletions of at least ICP0, ICP4, and ICP27, more preferably comprising inactivating deletions of ICP0, ICP4, ICP27 and ICP47), or also alternatively including the promoter or other regulatory sequences of such gene(s)). Alternatively, one or more of these HSV genes can be engineered to be expressed as an early or late gene. For example, the genome of certain embodiments of the inventive vector can be engineered to retain the coding sequence of one of more of these genes, but replace its promoter with one rendering the gene expressed as an early (beta) or late (gamma), but not immediate early (alpha) gene. For example, such gene can be placed under the control of a promoter responsive to ICP4 (an approach preferred at least with respect to ICP22, so as to express ICP22 as an early gene, rather than an immediate early gene). A suitable promoter for expressing such gene with early (beta) kinetics is the HSV tk promoter. The ICP22 promoter may be converted to early kinetics by truncation, i.e. deletion of regulatory sequences including TAATGAR-ATs. The entire ICP47 promoter and initiation codon can be deleted. Alternatively, in some embodiments, the ICP47 gene can be expressed as an immediate early gene to protect infected cells against immune recognition (Hill er al, *Nature* 1995, 375(6530): 411-415; Goldsmith et al, *J Exp Med.* 1998; 187(3): 341-348).

In addition to the perturbation of ICP0, ICP4, ICP22, ICP27, and ICP47 expression, desirably the inventive vector also does not express UL41 (i.e., the host shut-off (vhs) gene). UL41 is an RNAse that degrades many host and viral mRNAs, causes rapid shutoff of host cell protein synthesis, and enters cells as a virion tegument component. Thus, for example, the gene encoding UL41 can be deleted from the genome of the inventive vector. Without wishing to be bound by theory, it is believed that such manipulation additionally enhances the ability of the inventive vector to grow in complementing cells by sparing the complementing ICP4 and ICP27 mRNAs, and enhances the expression of transgenes in non-complementing cells by sparing the transgene mRNAs.

It should be recognized that the genome sequences of several HSV strains are known to persons of ordinary skill (e.g., MacDonald, *J. Virol.*, 86(11): 6371 (2012); McGeoch, *J. Gen. Virol.*, 69: 1531-1574 (1988); GenBank Accession No. JQ673480; NCBI Reference Sequence: NC_001806.1; MacDonald, *J. Virol.* 86(17): 9540 (2012); GenBank Accession No. JX142173, which are incorporated herein by reference). Accordingly, manipulation of the sequence of HSV genes and loci is within the level of ordinary skill. It should also be noted that these published sequences are merely exemplary and that other strains or variants of HSV can be employed as a source genome in engineering the inventive vector.

Additionally, the genome of the inventive vector can comprise a bacterial artificial chromosome (BAC) cassette. The inclusion of such BAC cassette facilitates propagation and manipulation of the inventive vector's genome within bacteria. The BAC cassette can include bacterially-expressed sequences that assist in the use of bacterial strains, e.g., selectable genes, such as genes conferring bacterial resistance to antibiotics or toxins (e.g., preferably chloramphenicol, but other resistance genes (e.g., for tetracycline, ampicillin, zeocin, etc.) can also be employed). The BAC cassette can further include reporter genes (e.g., LacZ (encoding beta-galactosidase), or a fluorescent protein-encoding gene (e.g., gfp (encoding green fluorescent protein), yfp (encoding yellow fluorescent protein), rfp (encoding red fluorescent protein), and analogues thereof (e.g., encoding iRFP, EGFP, and the like)) under the control of a eukaryotic promoter, such as a constitutive mammalian promoter (e.g., an SV40, RSV, CMV, ubiquitin C (UbC), CAG, or β-actin promoter, etc.).

The BAC cassette can be placed into the genome of the inventive vector in any suitable location, such as the UL37-UL38 intergenic region within the vector genome (e.g., Gierash, *J. Virol. Meth.*, 135: 197-206 (2006) and Morimoto, *Microbiol. Immunol.*, 53: 155-161 (2009)). Also, desirably, the BAC cassette is flanked by sequences facilitating removal of the BAC cassette, such as by site-specific recombinase recognition sites/consensus sequences (e.g., those recognized by enzymes such as cre, dre, flp, KD, B2, B3, R, etc.). The inclusion of such sites facilitates excision of the BAC cassette, if desired, since BAC sequences have been shown to reduce virus growth in cultured cells (e.g., Gierash, *J. Virol. Meth.*, 135: 197-206 (2006)). Also, excision of the BAC cassette can increase the capacity for the vector to incorporate one or more transgenes, since BAC cassettes are on the order of about 11 kb. It will be appreciated that, the inventive vector also can have a consensus sequence for a recombinase enzyme (e.g., loxP), particularly one not native to the HSV genome, for example as a result of removal of a BAC cassette using a cell line that expresses an appropriate site-specific recombinase for excizing the BAC cassette, as such leaves a single copy of the consensus sequences for a recombinase enzyme within the HSV genome (e.g., within the UL37-UL38 intergenic region, if such was the location of a BAC cassette insert).

As noted above, the inventive vector can include at least one transgene inserted in operable connection with one or more insulator sequences within the HSV vector genome. By "operably connected," it is to be understood that the one or more insulator sequences permit the transgene to be expressed in a cellular environment in which genetic elements (i.e., "genes") otherwise present within the HSV genome are transcriptionally silent. Without wishing to be bound by any particular theory, it is believed that such insulator sequences prevent the formation of heterochromatin at the sites of such insulator sequences and within from about 1 kb to about 5 kb thereof, which, if formed, silences gene expression. Thus, an insulator sequence for use in the inventive vector typically is a sequence that interferes with the binding or formation of heterochromatin, which would otherwise silence expression of the transgene. Non-limiting examples of suitable insulator sequences include HSV chromatin boundary (CTRL/CTCF-binding/insulator) elements CTRL1 and CTRL2 (which can be native to the LAT locus, as described herein, or moved to an ectopic location within the genome), chicken hypersensitive site 4 insulator (cHS4), human HNRPA2B1—CBX3 ubiquitous chromatin opening element (UCOE), and the scaffold/matrix attachment region (S/MAR) from the human interferon beta gene (IFNB1) (Emery, *Hum. Gene Ther.* 22, 761-74 (2011); Antoniou et al., *Hum. Gene Ther.* 24, 363-74 (2013)).

Aside from a transgene being inserted near insulator sequences native to the HSV genome (such as the CTRL1 and CTRL2 sequences within the LAT region), insulator sequences can be inserted into the vector genome at any suitable site. These insulator/boundary elements can be introduced into the genome of the inventive vectors by standard methods, and may be included in the same cassette as a transgene, or introduced separately into the genome so as to flank or otherwise be in operable connection with a given a transgene cassette. Thus, it is possible to insert a genetic cassette including, for example, one or more ectopic insulator sequences functionally similar to those found natively in the LAT region flanking, or otherwise in operable connection to, a transgene. It will be understood that the inventive vector can include multiple transgenes, operably linked to multiple insulator sequences, including at sites ectopic to LAT. In an embodiment in which one or more transgenes is inserted at a site other than LAT and is operably linked to CTRL1 and/or CTRL2, it is desired to delete from LAT or mutate the CTRL1 and/or CTRL2 sequences within LAT to minimize or eliminate recombination events between the native sequences within LAT and those engineered to be operably linked to a transgene within an ectopic (non-LAT) site of the inventive vector. Whether CTRL1 and CTRL2 remain within LAT or are moved ectopically, a preferred site for a transgene to be inserted into the genome of the inventive vector is between CTRL1 and CTRL2 (e.g., within about 1-4 kb of each of CTRL1 and CTRL2, wherein the CTRL1 and CTRL2 flank the transgene).

Within the inventive vector, one or more of such insulator sequences are operably linked with a transgene such that the transgene is insulated from gene silencing and is expressed. Generally, the transgene and the insulator sequence(s) should be in close proximity within the genome, such as separated by less than about 5 kb, or less than about 4 kb, or less than about 3 kb, or less than about 2 kb, or less than about 1 kb. It also can be desirable for an expression cassette (including a transgene) to be functionally between two insulator sequences such that the insulator sequences flank the transgene(s) of interest (See, e.g., Emery, *Hum. Gene Ther.* 22, 761-74 (2011); Antoniou et al., *Hum. Gene Ther.* 24, 363-74 (2013)).

One preferred site for insertion of a transgene (e.g., a first transgene) in the inventive vectors is between insulator sequences within the LAT gene region of the vector genome—specifically inserted between chromatin boundary (CTRL/CTCF-binding/insulator) elements located upstream of the LAT promoter LAP1 (CTRL1) and within the LAT 2-kb intron (CTRL2), respectively (Amelio et al, *J Virol* 2006, 80(5): 2358-2368; Bloom, *Biochim. Biophys. Acta*, 1799: 246-256 (2010)). This region is referred to herein as the LAT (gene) region or locus. Thus, desirably, the genome of the inventive vector comprises (e.g., retains) CTRL1 and CTRL2 (see FIG. 7, top). Without wishing to be bound by theory, it is believed that the presence of CTRL1 and CTRL2 protects the region against heterochromatin formation and, thus, contributes to the LAT gene region as being a privileged site for the expression of transgenes. Thus, the vector expresses the transgene inserted in the LAT gene region in non-complementing cells. In a preferred embodiment, the vector comprises a plurality of transgene cassettes within the LAT gene region, each comprising a separate promoter and coding region, and wherein each can be mono- or polycistronic.

Also, it is preferred for the LAT region of the inventive vector (which comprises at least one transgene, as noted herein) also to comprise (e.g., retain) a LATP2 or LAP2 enhancer element. Again without wishing to be bound by theory, it is believed that the presence of a LATP2 or LAP2 enhancer element contributes to the ability of the transgene within the LAT gene region to express the coding sequence(s) long-term (Goins, *J. Virol.*, 73: 519-532 (1999); Lilley, *J. Virol.*, 75: 4343-4356 (2001)). In a particularly preferred embodiment, the transgene(s) within the LAT gene region is inserted downstream of the LATP2 or LAP2 enhancer element. However, the invention contemplates embodiments in which the transgene(s) is inserted upstream (relative to the direction of LAT transcription) of the LATP2 or LAP2 enhancer element. Desirably, the transgene points away from the LATP2 or LAP2 elements within the LAT gene region (see, e.g., FIG. 7, top).

Another preferred site for insertion of a transgene (e.g., a second transgene) in the inventive vectors is within an ICP4 gene locus. For example, a UbC promoter-controlled transgene inserted in this locus within the inventive vector can produce a long-term signal in hippocampal neurons and is active at least short-term in rat DRGs.

Transgenes can also be inserted in operable connection with (e.g., near (<5 kb)) other insulator sequences within the genome of the inventive vectors. Aside from being inserted near insulator sequences native to the HSV genome, insulator sequences can be inserted into the vector genome at any suitable site. Thus, it is possible to insert a genetic cassette including, for example, ectopic insulator sequences functionally similar to those found natively in the LAT region flanking a transgene. It will be understood that the inventive vector can include multiple transgenes.

Within the transgene(s) inserted into the inventive vector, there are at least a promoter sequence and a transcribed sequence such that the transcribed sequence(s) is controlled by the promoter. The promoter within the transgene can be any promoter desired to control/regulate the expression of the transcribed sequence(s). For example, the promoter can be a cell-specific or tissue-specific promoter (e.g., EOS, OCT4, Nanog (for ESC/iPSC), SOX2 (for neural stem cells), αMHC, Brachyury, Tau, GFAP, NSE, Synapsin I (for neurons), Apo A-I, Albumin, ApoE (for liver), MCK, SMC α-Actin, Myosin heavy chain, Myosin light chain (for muscle), etc.), such as a promoter that specifically or preferentially expresses genes in a defined cell type (e.g., within a liver cell, lung cell, epithelial cell, cardiac cell, neural cell, skeletal muscle cell, embryonic, induced pluripotent, or other stem cell, cancer cell, etc.). Preferred promoters for use in sensory neurons include TRPV1, CGRP, and NF200. In other embodiments, the promoter within a transgene inserted into the inventive vector can be an inducible promoter (e.g., TRE3G combined with rtTA3G expression from a separate promoter in LAT or other inducible promoters as are known in the art). Of course, the promoter within a transgene expression cassette inserted into the inventive vector can be a constitutive mammalian promoter, such as are known in the art (e.g., SV40, CMV, CAG, EF1α, UbC, RSV, β-actin, PGK, and the like).

In addition to the promoter(s) and coding sequence(s), the transgene(s) inserted into the genome of the inventive vector also can comprise additional regulatory element(s). For example, the transgene(s) can include one or more sites for binding of microRNA. In preferred embodiments, the transgene(s) comprise tandem binding sites for such microRNAs, such as 2, 3, 4, 5, or 6 tandem sites (four being typical). The presence of such sites, particularly tandem binding sites for such microRNAs, facilitates down-regulation of the transgene expression in certain cell types. Thus, for example, a vector comprising a transgene desired to be expressed in a cancer or tumor cell (which may be toxic to many cell types) can comprise binding sites for microRNAs of "normal" (i.e., non-malignant) cells, so that the expression of the transgene is suppressed in non-malignant cells.

It should be noted that the transgene(s) within the inventive vector can be monocistronic (i.e., encoding a single protein or polypeptide) or polycistronic (i.e., encoding multiple proteins or polypeptides). Moreover all or part of the transcribed portion of the transgene also can encode non-translated RNA, such as siRNA or miRNA, for example. Also the inventive vector can comprise multiple separate monocistronic or polycistronic transgene units (preferably two separate transgene units but possibly more (e.g., three, four, five, or more separate units)), each with its own respective promoter, translated sequence(s) or non-translated RNA sequence(s), and other regulatory elements.

As noted, the transgene(s) include(s) one or more transcribed sequence(s), which are expressed under the control of the promoter and optionally other regulatory elements within the transgene (including the operable connection to the insulator sequence(s)). A transcribed sequence can be any sequence desired to be expressed within a given cell into which the vector is to be introduced. Non-limiting examples of transcribed sequences that can be present in a transgene within the inventive vector include Oct4, Klf4, Sox2, c-Myc, L-myc, dominant-negative p53, Nanog, Glis1, Lin28, TFIID, GATA4, Nkx2.5, Tbx5, Mef2C, Myocd, Hand2, SRF, Mesp1, SMARCD3, SERCA2a, Pax3, MyoD, Lhx2, FoxG1, FoxP2, Isl1, Ctip2, Tbr1, Ebf1, Gsx2, Srebp2, Factor VIII, Factor IX, Dystrophin, CFTR, GlyRα1, enkephalin, GAD67 (or other GAD isoforms, e.g., GAD 65), TNFα, IL-4, a neurotrophic factor (e.g., NGF, BDNF, GDNF, NT-3), Ascl1, Nurr1, Lmx1A, Brn2, Mytl1, NeuroD1, FoxA2, Hnf4α, Foxa1, Foxa2 or Foxa3, any microRNA or combination of miRNAs (e.g., hsa-mir-302/367 gene cluster; hsa-miR200c; hsa-miR369; hsa-mir-124) and/or one or more other non-coding RNAs ("ncRNA(s)") or a reporter gene for expression in mammalian cells, such as LacZ (encoding beta-galactosidase), CAT (encoding chloramphenicol acetyltransferase), or a fluorescent protein-encoding gene (e.g., GFP, YFP, RFP, and analogues thereof such as iRFP, EGFP, and the like).

In addition to the foregoing, the inventive vector optionally also can comprise an expression cassette inserted in a site other than the LAT region or other than in the vicinity of known insulator sequences. A preferred site for such expression cassette is ICP4. For example, when the vector comprises a complete or inactivating deletion of the ICP4 gene, the expression cassette can be inserted into the site of the ICP4 deletion. Desirably, the coding sequence of the expression cassette inserted into a site other than the LAT region is controlled by a constitutive mammalian promoter (e.g., SV40, CMV, CAG, EF1α, UbC, RSV, β-actin, PGK, and the like), but other promoters (as discussed herein and otherwise known in the art) can be used, if desired. One exemplary expression cassette includes UbCp driving expression of mCherry, engineered into a deleted ICP4 locus. Of course, such a transgene can encode a factor of therapeutic interest as well.

In addition to the foregoing, the inventive HSV vector also desirably comprises a deletion of the internal repeat (Joint) region, comprising IR$_S$ and IR$_L$. Deleting this region can contribute to the stability of the vector genome, and deleting this sequence of HSV DNA also allows for the vector to accommodate large transgenes (at least 15 kb) and still be packaged correctly into mature virions. Deletion of the Joint eliminates one copy each of the IE genes ICP0 and ICP4 such that the remaining copies can be easily manipulated. It also deletes the promoter for the ICP22 or ICP47 immediate early gene. If desired, expression of the ICP47 gene can be restored by insertion of an immediate early promoter, preferably the ICP0 promoter or the HCMV major IE promoter, to minimize immune recognition of infected cells (Hill er al, *Nature* 1995, 375(6530): 411-415; Goldsmith et al, *J Exp Med.* 1998; 187(3): 341-348).

HSV is able to infect a wide variety of mammalian cells; thus, the inventive vector has broad applicability. However, to enhance infectivity, desirably the envelope of the inventive vector can further include a mutant glycoprotein that enhances infection and/or lateral spread relative to a wild-type glycoprotein. Alternatively or in addition, the envelope of the inventive vector can further include a mutant glycoprotein that directs HSV entry into cells through non-canonical receptors. For example, such mutant glycoprotein(s) can be gB, gC, gD, gH, or gK; of course, the vector can have more than one such mutant (enhanced-penetration or -spread) glycoproteins (e.g., a combination of two, more, or even all thereof). Furthermore, technology for mutating such glycoproteins to enhance HSV infection and/or lateral spread is known, and any such technology can be employed in the context of the present invention (see, e.g., U.S. Patent Application Publication No. 2013-0096186 A1; International Patent Application Publication No. WO/1999/006583, Uchida, *J. Virol.*, 84: 12200-12209 (2010), Uchida et al., J. Virol., 87(3). 1430-42 (2013), and Uchida, *Mol. Ther.*, 21: 561-569 (2013), which are incorporated herein by reference). Moreover, the genome of the inventive vector can comprise a mutant gene encoding such mutant glycoprotein(s).

Figure 7:
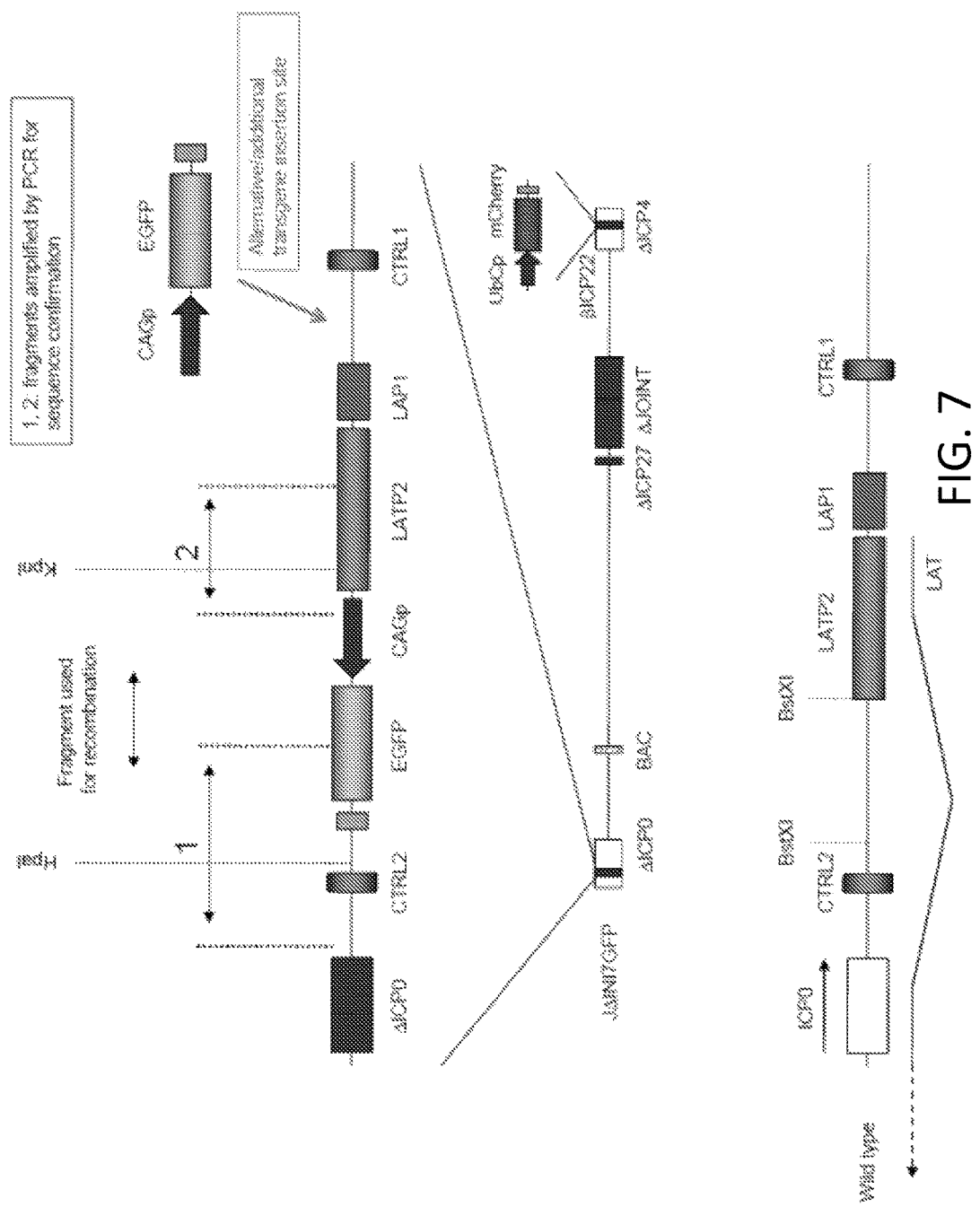
FIG. 7 is a schematic of a HSV vector of the present invention (JΔNI7-GFP, center), the LAT region of JΔNI7-GFP (top), and the LAT region of a wild-type HSV (bottom).

Exemplary vector "backbones" embodying the invention are described herein as "JΔNI5" and "JΔNI8" with the understanding that, as "backbones," it is contemplated that transgenes with or without extraneous control elements can be inserted into the LAT region of these specific vectors (see, e.g., FIG. 7, top).

One application of the inventive vectors is the reprogramming of a variety of cell types to produce pluripotent stem cells. Stem cells have been at the forefront of biomedical research in recent years and hold a great deal of promise for understanding human development, genetic disease and the creation of new therapies in regenerative medicine. In 2006, Yamanaka and colleagues discovered a means of creating embryonic-like stem cells by reprogramming adult fibroblasts (Takahashi and Yamanaka, *Cell* 126: 663-76, 2006). These novel cells, designated induced pluripotent stem (iPS) cells, are functionally similar to ES cells (Wernig et al, *Nature* 448: 318-24, 2007) and when derived from human somatic cells (Takahashi et al, *Cell* 131: 861-72, 2007; Yu et al, *Science* 318: 1917-20, 2007), sidestep the ethical concerns involving the use of human ES cells. Four reprogramming genes were originally employed for iPS cell production (Takahashi and Yamanaka, *Cell* 126: 663-76, 2006; Takahashi et al, *Cell* 131: 861-72, 2007, but the efficiency of reprogramming with these or other genes has remained problematic due to inefficient gene transfer methods. The inventive vector system addresses this issue by combining high transduction efficiency for many cell types with the capability of expressing multiple transgenes simultaneously from a single vector. For example, the JΔNI7 and JΔNI8 vectors described herein are replication-defective and non-toxic due to deletion or altered expression kinetics of the five viral IE genes. Since they do not integrate into the cellular genome, such vectors are diluted during cell division, providing a hit-and-run gene delivery system.

To facilitate growing, producing, and propagating the inventive vectors and producing stocks thereof, an aspect of the invention provides a complementing cell line, which complements ICP0 and ICP4, desirably ICP0, ICP4 and ICP27. Preferably, the ICP0 complementation is achieved without expressing HSV ICP0, to reduce toxicity within the complementing cell. Thus, a preferred complementing cell according to the present invention is derived from a cell type that naturally complements HSV ICP0 function, such as U2OS cells (Yao, *J. Virol.*, 69: 6249-6258 (1995), which is incorporated herein by reference). Such cells can be engineered to express ICP4 or ICP4 and ICP27 by methods known in the art (e.g., by introducing ICP4 or ICP4 and ICP27 expression cassettes within the cells so that they express ICP4 and ICP27, respectively, from genetic constructs other than the HSV genome, such as the cellular chromosomes). Desirably, the cell line expresses ICP4 and ICP27, respectively, in trans. Desirably, the introduced ICP4 or ICP4/ICP27 coding sequences are under the control of their cognate viral promoters. Also, one or both of the ICP4 and ICP27 complementing coding sequences can be inducibly expressed within such cells in response to infection with HSV.

As noted above, embodiments of the inventive vector comprise a BAC flanked by sequences facilitating removal of the BAC cassette by a site-specific recombinase recognition. Accordingly, the inventive complementing cell can be engineered to further express a gene encoding a site-specific recombinase appropriate to the recognition sequences within the vector, thereby producing the recombinase protein. Thus, the inventive complementing cell can express and produce cre, dre, flp, KD, or B2, B3, R, and the like, or a mutant derivative thereof, as appropriate. Passage through such a cell line, thus, recovers room for transgenes (about 11 kb) and can improve virus growth by over 10 fold, such as over 25 fold, or over 50 fold, such as about 100 fold. The improved viral growth can be assayed by standard procedures (to produce growth curves) in comparison with cells that lack the recombinase. This involves infection of replicate wells of cells at low MOI, virus collection at different times post infection, and titration of the yields typically by plaque assay.

Additionally, the complementing cell line can be engineered to express a gene encoding a selectable marker, such as markers typically employed in engineering packaging cells or cells expressing any other foreign gene. Suitable selectable genes include those conferring resistance to neomycin/G418, hygromycin, blasticidin, puromycin, zeocin, and the like.

It will be understood that methods for engineering a source cell type (e.g., U2OS cells) to contain expression constructs encoding the HSV ICP4 and ICP27 proteins, as well as other proteins (such as the recombinase and/or the selectable gene product) are known to persons of ordinary skill. For example, the gene of interest with a selectable marker can be subcloned into lentiviral vectors, the source cell infected with the lentiviral vectors, selected for expression of the marker (e.g., blasticidin resistance), and then expression of the transgene of interest (e.g., HSV ICP27) confirmed.

Of course, the inventive complementing cell can be propagated and cloned. Thus, the invention provides a clonal population, i.e., a cell line, comprising or consisting of or essentially of the complementing cell line as described herein.

Using the inventive complementing cells of the invention, the inventive HSV vector can be propagated. Accordingly, the invention provides a method of propagating the HSV vector of the present invention. In accordance with the inventive method, the complementing cell line is transfected with vector DNA and then cultured until plaques form. The viral DNA, as noted, can have a BAC, and, if so, then the inventive cell can express the recombinase appropriate for excising the BAC from the viral genome, if it is desired not to include the BAC in the packaged vector. The viral population is amplified by repeated transfer of infectious particles to increasingly large, fresh populations of the complementing cells. For these repeated transfers, multiplicity of infection (MOI) can be between about 0.001 pfu/cell and about 0.03 pfu/cell. Ultimately, the inventive vectors (as packaged viruses) are purified from the cells at 90% cytopathic effect.

Generally, the inventive HSV vector is most useful when enough of the virus can be delivered to a cell population to ensure that the cells are confronted with a suitable number of viruses. Thus, the present invention provides a stock, preferably a homogeneous stock, comprising the inventive HSV vector. The preparation and analysis of HSV stocks is well known in the art. For example, a viral stock can be manufactured in roller bottles containing cells transduced with the HSV vector. The viral stock can then be purified on a continuous nycodenze gradient, and aliquotted and stored until needed. Viral stocks vary considerably in titer, depending largely on viral genotype and the protocol and cell lines used to prepare them. Preferably, such a stock has a viral titer of about $10^6$ pfu/ml or even more preferably about $10^7$ pfu/ml (or at least about such values). In still more preferred embodiments, the titer can be about $10^8$ pfu/ml, or about $10^9$ pfu/ml (or at least about such values), and high titer stocks of about $10^{10}$ pfu/ml or about $10^{11}$ pfu/ml or even about $10^{12}$ pfu/ml (or at least about such values) are most preferred. Thus, the titer of an HSV stock according to the present invention can vary from about $10^6$ pfu/ml to about $10^{12}$ pfu/ml (preferably between about $10^9$ to about $10^{11}$ pfu/ml). Genome copy (gc) numbers provide a cell line-independent measure of the number of virus particles, but include defective particles. Typically gc values for wild-type HSV-1 are several to 20×, up to 100×, higher than the pfu values of the same stocks. For mutant viruses, especially defective viruses grown on complementing cells, this can increase to 10,000× higher or even more. Gc and pfu values increase proportionally with the size of the stock.

The invention additionally provides a composition comprising the HSV vector and a carrier, preferably a physiologically-acceptable carrier. The carrier of the composition can be any suitable carrier for the vector. The carrier typically will be liquid, but also can be solid, or a combination of liquid and solid components. The carrier desirably is a pharmaceutically acceptable (e.g., a physiologically or pharmacologically acceptable) carrier (e.g., excipient or diluent). Pharmaceutically acceptable carriers are well known and are readily available. The choice of carrier will be determined, at least in part, by the particular vector and the particular method used to administer the composition. The composition can further comprise any other suitable components, especially for enhancing the stability of the composition and/or its end-use. Accordingly, there is a wide variety of suitable formulations of the composition of the invention. The following formulations and methods are merely exemplary and are in no way limiting.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the vector and physiological distress. Immune system suppressors can be administered with the composition method to reduce any immune response to the vector itself or associated with a disorder. Alternatively, immune enhancers can be included in the composition to up-regulate the body's natural defenses against disease. Antibiotics, i.e., microbicides and fungicides, can be present to reduce the risk of infection associated with gene transfer procedures and other disorders.

Using the inventive vector (and stocks and compositions comprising the vector), the invention provides a method of expressing a transgene within a nucleated cell, especially a non-complementing cell. In accordance with the method, the inventive vector is exposed to the cell under conditions suitable for the vector to infect the cell. Once the cell is infected, the transgene inserted within the vector's LAT region will be transcribed (expressed) within the cell, provided the promoter within the transgene is one which is active in the cell and that the transgene is not suppressed by another regulatory mechanism (e.g., the microRNAs discussed herein). In other words, the inventive vectors serve as gene transfer and expression vectors within mammalian cells.

The inventive method can be employed to express transgene(s) within cells either in vivo or in vitro, as desired. For use in vivo, the cell can be any type of desired cell, such as exocrine secretory cells (e.g., glandular cells, such as salivary gland cells, mammary gland cells, sweat gland cells, digestive gland cells, etc.), hormone secreting gland cells (e.g., pituitary cells, thyroid cells, parathyroid cells, adrenal cells, etc.), ectoderm-derived cells (e.g., keratinizing epithelial cells (e.g., making up the skin and hair), wet stratified barrier epithelial cells (e.g., of the cornea, tongue, oral cavity, gastrointestinal tract, urethra, vagina, etc.), cells of the nervous system (e.g., peripheral and central neurons, glia, etc.)), mesoderm-derived cells, cells of many internal organs (such as kidney, liver, pancreas, heart, lung) bone marrow cells, and cancerous cells either within tumors or otherwise. Preferred, and non-limiting examples of cells suitable for infection by the inventive vectors include liver cells, lung cells, epithelial cells, cardiac cells, muscle cells, stem cells, and cancer cells.

It will be observed that, when used in vivo, the inventive method can treat a disease or a condition within a subject, when the transgene within the vector encodes one or more prophylactically- or therapeutically-active proteins, polypeptides, or other factor (e.g., non-coding RNA (ncRNA) such as siRNA or miRNA). Thus, the invention provides a method of treating a disease or condition in a subject, comprising administering the vector of the present invention to the subject, in an amount and at a location sufficient to infect cells of the subject such that the transgene is expressed within the cells of the subject, and wherein the transgene encodes one or more prophylactically or therapeutically active proteins, polypeptides or ncRNA. For example, the disease or condition can be a type of cancer, in which the transgene can encode an agent that enhances tumor killing activity (such as TRAIL or tumor necrosis factor (TNF)). As additional non-limiting example, the transgene can encode an agent suitable for the treatment of conditions such as muscular dystrophy (a suitable transgene encodes Dystrophin), cardiovascular disease (suitable transgenes include, e.g., SERCA2a, GATA4, Tbx5, Mef2C, Hand2, Myocd, etc.), neurodegenerative disease (suitable transgenes include, e.g., NGF, BDNF, GDNF, NT-3, etc.), chronic pain (suitable transgenes encode GlyRα1, an enkephalin, or a glutamate decarboxylase (e.g., GAD65, GAD67, or another isoform), lung disease (e.g., CFTR), or hemophilia (suitable transgenes encode, e.g., Factor VIII or Factor IX).

In other embodiments, the inventive method can be used in vitro to cause expression of the transgene within cells in culture. Again, any type of cells can be infected in vitro with the inventive method, such as stem cells and fibroblasts, such as a human dermal fibroblast (HDF) or a human lung fibroblast (HLF). Other preferred types of cells for use in vitro include keratinocytes, peripheral blood mononuclear cells, hematopoietic stem cells (CD34+), or mesenchymal stem/progenitor cells. In one embodiment, the transgene(s) encode one or more factors that can effect the differentiation of the cell. For example, expression of one or more of Oct4, Klf4, Sox2, c-Myc, L-Myc, dominant-negative p53, Nanog, Glis1, Lin28, TFIID, mir-302/367, or other miRNAs can cause the cell to become an induced pluripotent stem (iPS) cell. See also, Takahashi and Yamanaka, *Cell,* 126: 663-676 (2006); Takahashi, *Cell,* 131: 861-872 (2007); Wernig, *Nature,* 448: 318-324 (2007); and Yu, *Science,* 318: 1917-1920 (2007), the disclosures of which are incorporated herein by reference. Alternatively, the transgene(s) within the inventive vectors can encode a factor for transdifferentiating the cells (e.g., one or more of GATA4, Tbx5, Mef2C, Myocd, Hand2, SRF, Mesp1, SMARCD3 (for cardiomyocytes); Ascl1, Nurr1, Lmx1A, Brn2, Mytl1, NeuroD1, FoxA2 (for neural cells), Hnf4a, Foxa1, Foxa2 or Foxa3 (for hepatic cells)

In practicing the inventive method involving infecting a cell in vivo or in vitro with the vector, composition, or stock of the invention, the cell can be any mammalian nucleated cell for which it is desired to express the transgene. HSV has broad infectivity and, as noted herein, the inventive vector can be engineered to alter its natural tropism and to enhance infectivity by mutating viral envelope glycoproteins. Thus, the vector can be employed to infect cells of many mammalian species. It is believed that the inventive methods can be applied in agriculture, such as to express exogenous genes or supplement for deficient genes in animals such as cattle, horses, sheep, goats, swine, and the like. Similarly, the inventive method can be employed in a veterinary context for companion animals, such as cats, dogs, and the like.

Of course, the inventive method can be used in vivo in humans as well, to provide for the expression of a prophylactically- or therapeutically-active agent, or factor, in a medical setting. The factor (supplied by expression of one or more of the transgenes within the inventive vectors) can be exogenous, or one that complements a genetic deficiency.

The following examples further illustrate the invention but, of course, should not be construed as in any way limiting its scope.

Example 1

This example describes the development of a complementing cell line for replicating and producing the inventive HSV vectors.

Several of the immediate early (IE) genes of HSV are essential for virus replication, but these and other IE genes have toxic effects in a variety of cell types. While the removal of these genes prevents vector toxicity, the essential products must be provided in order to produce infectious viral particles. A novel cell line, based on U2OS human osteosarcoma cells, was engineered to conditionally express the essential IE genes ICP4 and ICP27. These genes were introduced under the control of their cognate viral promoters by retrovirus-mediated insertion. As such these genes may remain silent until HSV infection delivers the HSV tegument protein VP16 to the nucleus where it promotes high-level expression of the integrated ICP4 and ICP27 genes by activation of their promoters. Thus, prior to HSV infection, these genes can be stably maintained in the engineered U2OS cells without unsuitable toxicity. HSV growth also relies on the expression of ICP0, but this protein inhibits cell replication, causing cell cycle arrest and programmed cell death. Remarkably, U2OS cells naturally complement ICP0 functions and thus the introduction of ICP4 and ICP27 is sufficient to provide a cellular environment for efficient production of vectors deleted for all three IE genes. This novel engineered cell line is stable, grows well in culture and can be used for clinical production of non-toxic HSV vectors.

U2OS-ICP4/27 cells and 7b (Vero-ICP4/ICP27) cells were infected with E1G6 (ΔICP4::HCMVp-eGFP/ΔICP27/B22/1347) or JDQOZEH1 (ΔICP4/ΔICP27/ΔICP22/ΔICP0::HCMV-eGFP) viruses. After 3 days, virus in the cell supernatants were titered on U2OS-ICP4/27 cells.

| Virus | Production Cell Line | Titer (PFU/ml) | Fold Difference (U2OS-ICP4/27 vs 7b) |
|---|---|---|---|
| E1G6 | U2OS-ICP4/27 | $2.9 \times 10^5$ | 328x decrease |
|  | 7b | $9.5 \times 10^7$ |  |
| JDQOZEH1 | U2OS-ICP4/27 | $2.6 \times 10^5$ | 2600x increase |
|  | 7b | $1.0 \times 10^2$ |  |

The data show that E1G6 (ICP4- and ICP27-deleted; no expression of ICP22 and ICP47) grew on both cell lines whereas JDQOZEH1 (deleted for ICP0, ICP4, ICP27 and ICP22) was only able to grow on U2OS-ICP4/27 cells. The JDQOZEH1 titer in 7b supernatant likely represents residual input from the 7b infection.

Example 2

This example describes an embodiment of a HSV vector comprising a genome comprising a transgene inserted within a LAT gene region, wherein the vector does not express ICP0, ICP4, ICP22, ICP27, and ICP47 as immediate early genes.

The vector genome (FIG. 1A) contains a Cre-removable bacterial artificial chromosome (BAC) cassette in the UL37-UL38 intergenic region allowing propagation and manipulation in bacteria. It is deleted for the non-essential internal repeat region (Joint, 14 kb) separating the $U_L$ and $U_S$ segments to provide space for transgene insertion and increase vector stability. The vector is replication defective due to deletion of the ICP4 and ICP27 genes, and is additionally deleted for the toxic IE gene ICP0 and the promoter and start codon of the ICP47 IE gene; the remaining toxic IE gene, ICP22, is controlled by an ICP4-dependent (early, 13) promoter, so as to express ICP22 during the "early," rather than the "immediate early," phase of HSV gene expression in ICP4-complementing cells. Because U2OS cells naturally complement ICP0, the vector was grown in a U2OS-based virus producer cell line, U2OS-ICP4/ICP27, that complements the functions of all of these IE genes except that of the dispensable ICP47 gene. The vector genome also contains a pair of mutations in the gB gene that enhance virus entry into cells and a ubiquitin (UbC) promoter-mCherry reporter gene expression cassette at the position of the ICP4 deletion. In non-complementing cells, the latency-associated transcript (LAT) promoter region, which is located between insulator (CTRL) elements that protect the region against heterochromatin formation remains active. This region includes an enhancer element, LAT P2 or LAP2, that promotes long-term gene expression. A CAG promoter-GFP expression cassette was inserted between LATP2 and CTRL2 and robust GFP expression was observed in infected human dermal fibroblast (HDF) cells whereas minimal expression was observed from the same GFP cassette inserted at other locations in the genome or from the mCherry cassette (FIG. 1B). Thus, in the complete absence of IE gene expression, the LAT locus is a privileged site for transgene expression.

FIG. 1A shows structures of the complete HSV-1 genome with the BAC sequences in UL (top), and the base vector construct. The LAT and UL3-UL4 regions are enlarged underneath and the alternative positions of CAG-GFP insertion are indicated. FIG. 1B shows GFP expression from alternative positions in the vector genome in infected HDFs. The GFP gene within this vector encodes EGFP.

Example 3

This example lists the structure and properties of various HSV vector constructs.

| Virus | vector feature | | | | | | | | | | |
|---|---|---|---|---|---|---|---|---|---|---|---|
| | ICP 0 | ICP 4* | ICP 22 | ICP 27 | ICP 47 | LAT | $UL_{41}$ | $UL_{3-4}$ | HDF toxicity | mCherry expression ** | GFP expression ** |
| JΔβββ3 | β | Δ | β | β | Δp | wt | wt | wt | ++++ | + | n/a |
| JΔNI3 | Δ | Δ | β | β | Δp | wt | wt | wt | +++ | − | n/a |
| JΔβββ4 | β | Δ | β | β | Δp | wt | wt | EF1α-GW | ++++ | + | n/a |
| JΔNI4 | Δ | Δ | β | β | Δp | wt | wt | EF1α-GW | +++ | − | n/a |
| JΔNI5 | Δ | Δ | β | Δ | Δp | wt | wt | wt | + | − | n/a |
| JΔNI6 | Δ | Δ | β | Δ | Δp | wt | wt | EF1α-GW | = | − | n/a |
| JΔNI6-EF1αGFP | Δ | Δ | β | Δ | Δp | wt | wt | EF1α-GFP | + | − | − |
| JΔNI6-CAGGFP | Δ | Δ | β | Δ | Δp | wt | wt | CAG-GFP | + | − | − |
| JΔNI7-GFP | Δ | Δ | β | Δ | Δp | CAG-GFP | wt | wt | + | − | +++ |
| JΔNI7-EF1α2GFP | Δ | Δ | β | Δ | Δp | ²EF1α2-GFP | wt | wt | + | − | + |
| JΔNI7-miR302GFP | Δ | Δ | β | Δ | Δp | ²EF1α2-miR302/367-GFP | wt | wt | ? | ? | ? |
| JΔNI8 | Δ | Δ | β | Δ | Δp | wt | Δ | wt | − | − | n/a |
| JΔNI8-GFP | Δ | Δ | β | Δ | Δp | CAG-GFP | Δ | wt | − | + | +++ |

† Δ = deletion; β = converted to early expression kinetics; Δp = promoter and start codon deleted
¹ CAG promoter
²Contains EF1α first intron following the EF1α promoter
*All have the same mCherry expression construct in the deleted ICP4 locus
** In HDF (human dermal fibroblasts) at 3 dpi Example 4

Figure 1:
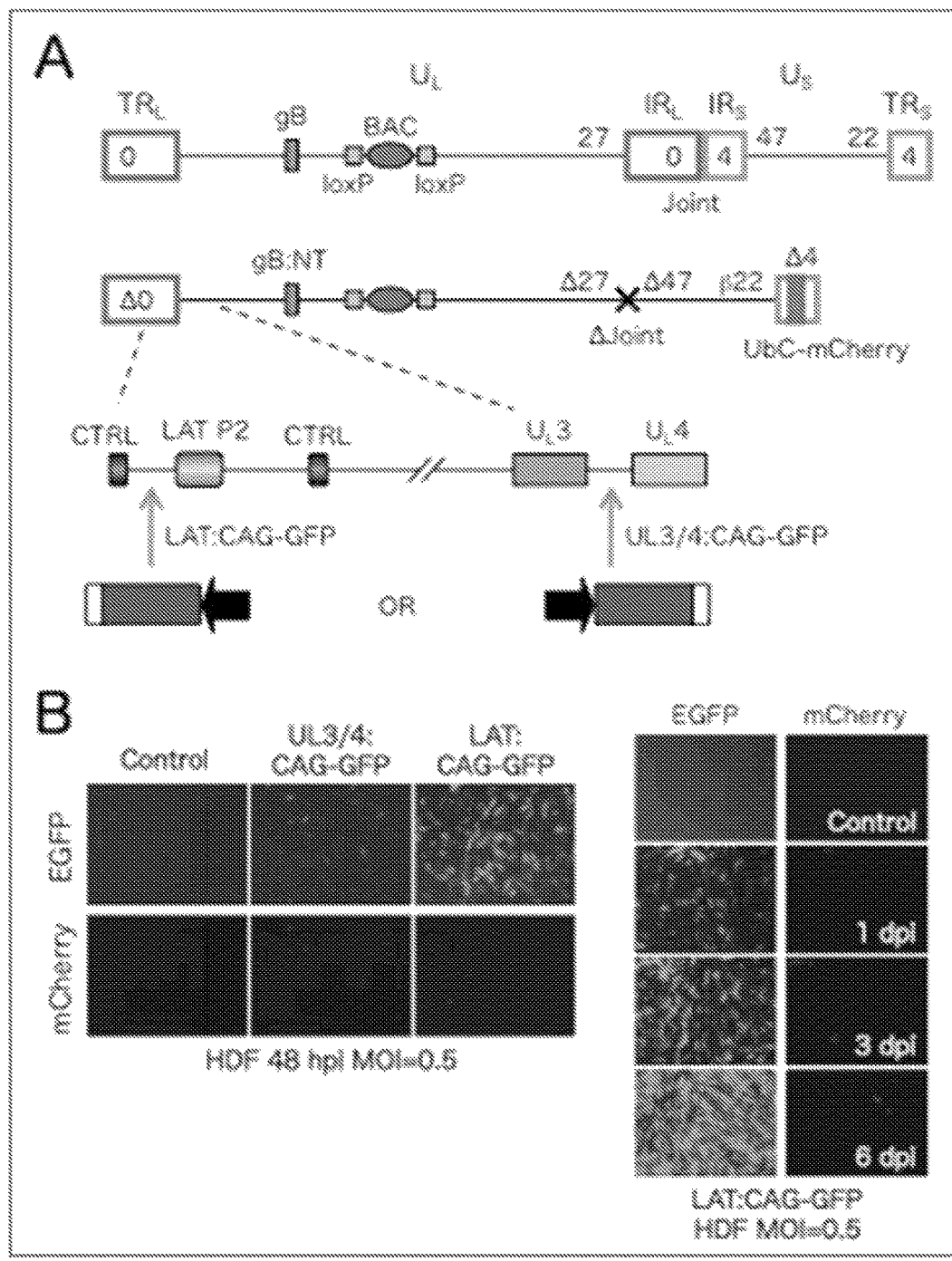
FIG. 1A is a vector schematic showing reporter gene expression. The top line represents the full-length wild-type HSV-1 strain KOS BAC clone (Gierash, *J. Virol. Meth.*, 135: 197-206 (2006)) used to generate the JΔNI vectors of the invention. The second line represents JΔNI5, i.e. the backbone of JΔNI7-GFP. The third line is a blow-up of the LAT to UL4 region of JΔNI5. The left side of the 4th line (LAT:CAG-GFP) shows the position of the reporter expression cassette in JΔNI7-GFP. The right side of the 4th line (UL3/4:CAG-GFP) shows the position of the same expression cassette in a JΔNI5-derived control vector (JΔNI6-CAGGFP).
FIG. 1B is a set of photographs showing reporter gene expression.

This example demonstrates the transgene expression in JΔNI7-GFP- and JΔNI6-CAGGFP-infected cells. The location of CAG-GFP in JΔNI7-GFP is shown in FIG. 1 as LAT:CAG-GFP; its location in JΔNI6-CAGGFP is shown in FIG. 1 as UL3/4:CAG-GFP. Furthermore, the sequence of the LAT region of JΔNI7-GFP HSV is set forth in FIG. 8 (SEQ ID NO:1), including the sequences of various genetic elements within the LAT region. It will be noted that the GFP within these vectors encodes EGFP.

The biological titer of the virus stock was determined on U2OS-ICP4/ICP27 cells and the genome copy (gc) titer was determined by quantitative real-time PCR for the viral glycoprotein D gene. The particle (gc)-to-plaque forming units (PFU) ratios for JΔNI6-CAGGFP and JΔNI7-GFP were comparable. See Example 8, table 2.

Figure 2A:
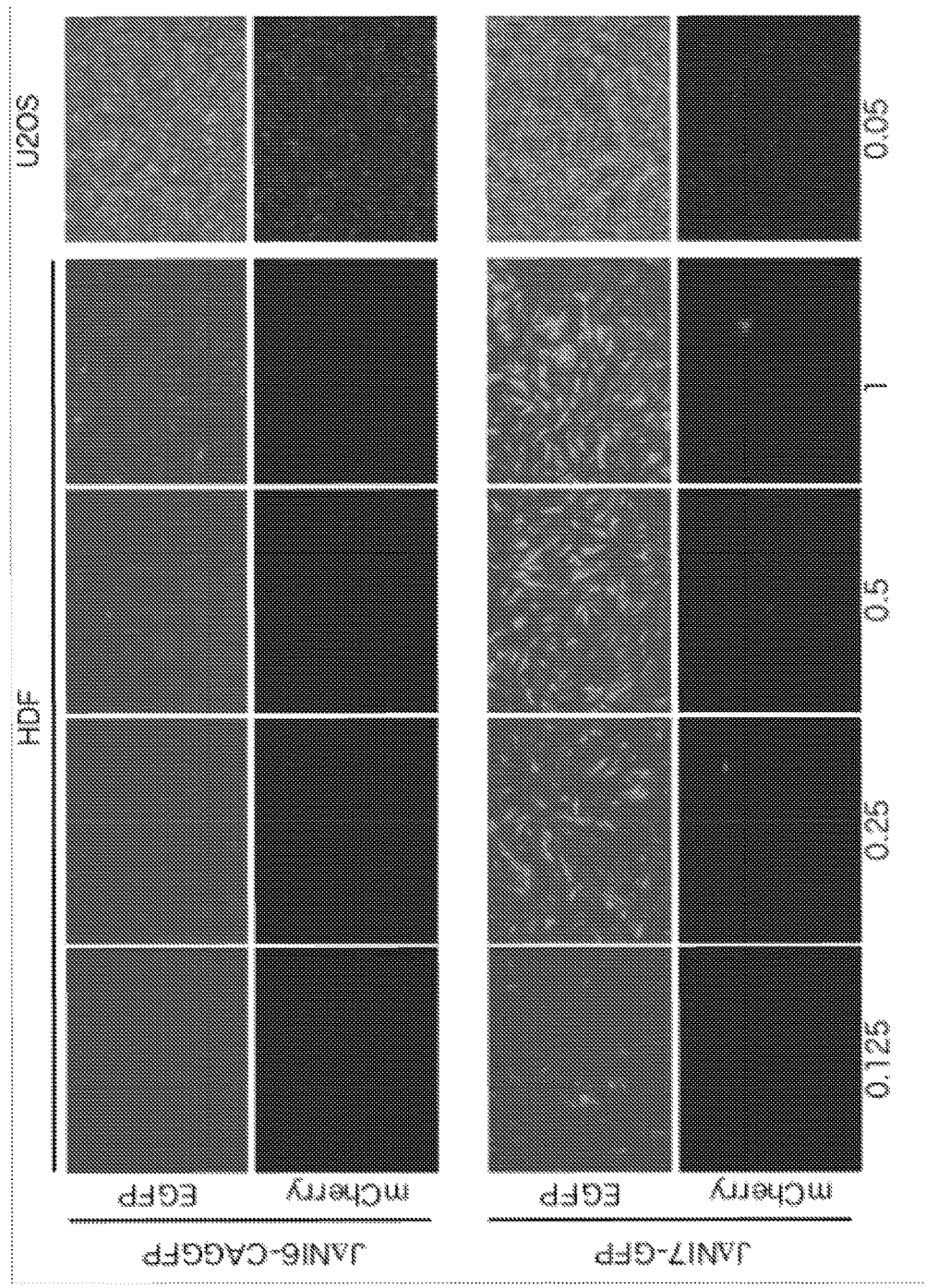
FIGS. 2A-2B is a set of photographs comparing transgene expression in JΔNI6-CAGGFP- and JΔNI7-GFP-infected cells.
Figure 2B:
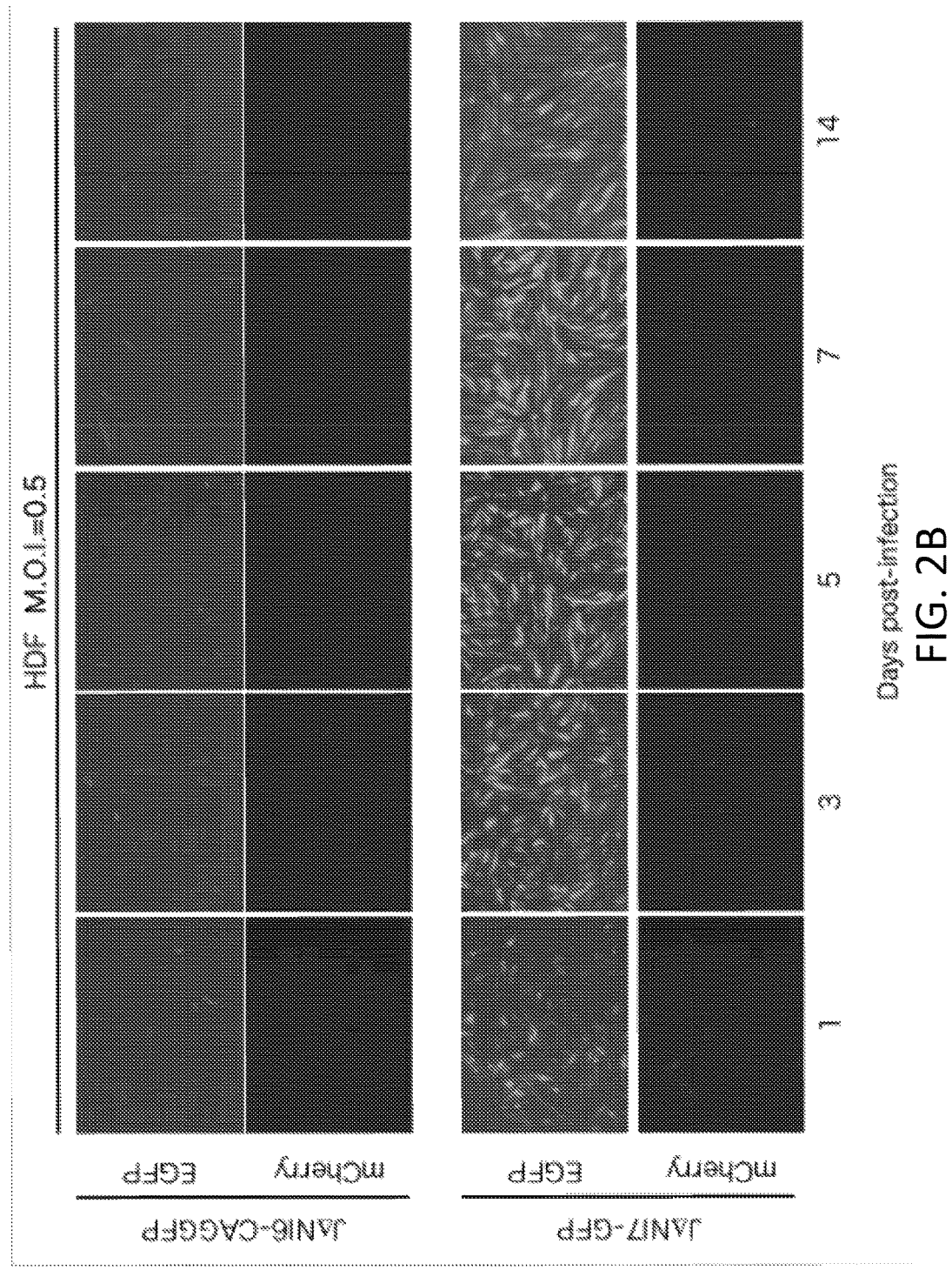

Non-complementing human dermal fibroblasts (HDF) and ICP0-complementing U2OS cells were infected with each virus in order to compare their transgene expression. JΔNI7-GFP, containing the CAG-GFP cassette in the LAT locus, showed strong, viral dose-dependent GFP expression in HDF whereas the highest dose of JΔNI6-CAGGFP yielded only minimal GFP expression (FIG. 2A, left panels, EGFP). GFP expression in JΔNI7-GFP-infected HDF remained detectable 2 weeks after infection (FIG. 2B, EGFP). However, little or no mCherry expression was observed from either virus in HDF (FIG. 2A, 2B, mCherry), suggesting that genes outside the LAT locus are silenced in HDF. In contrast, abundant GFP and mCherry expression was observed for both viruses at low MOI in U2OS cells (FIG. 2A, right column), consistent with the interpretation that the ICP0-like activity of these cells prevents the silencing of non-LAT loci occurring in HDF. Together, these results strongly indicated that the LAT locus is a preferred site for transgene expression from replication-defective, ICP0-deficient vectors.

Example 5

This example demonstrates the production of two isolates of JΔNI7-miR302GFP BAC in U2OS-ICP4/ICP27 cells.

Figure 3:
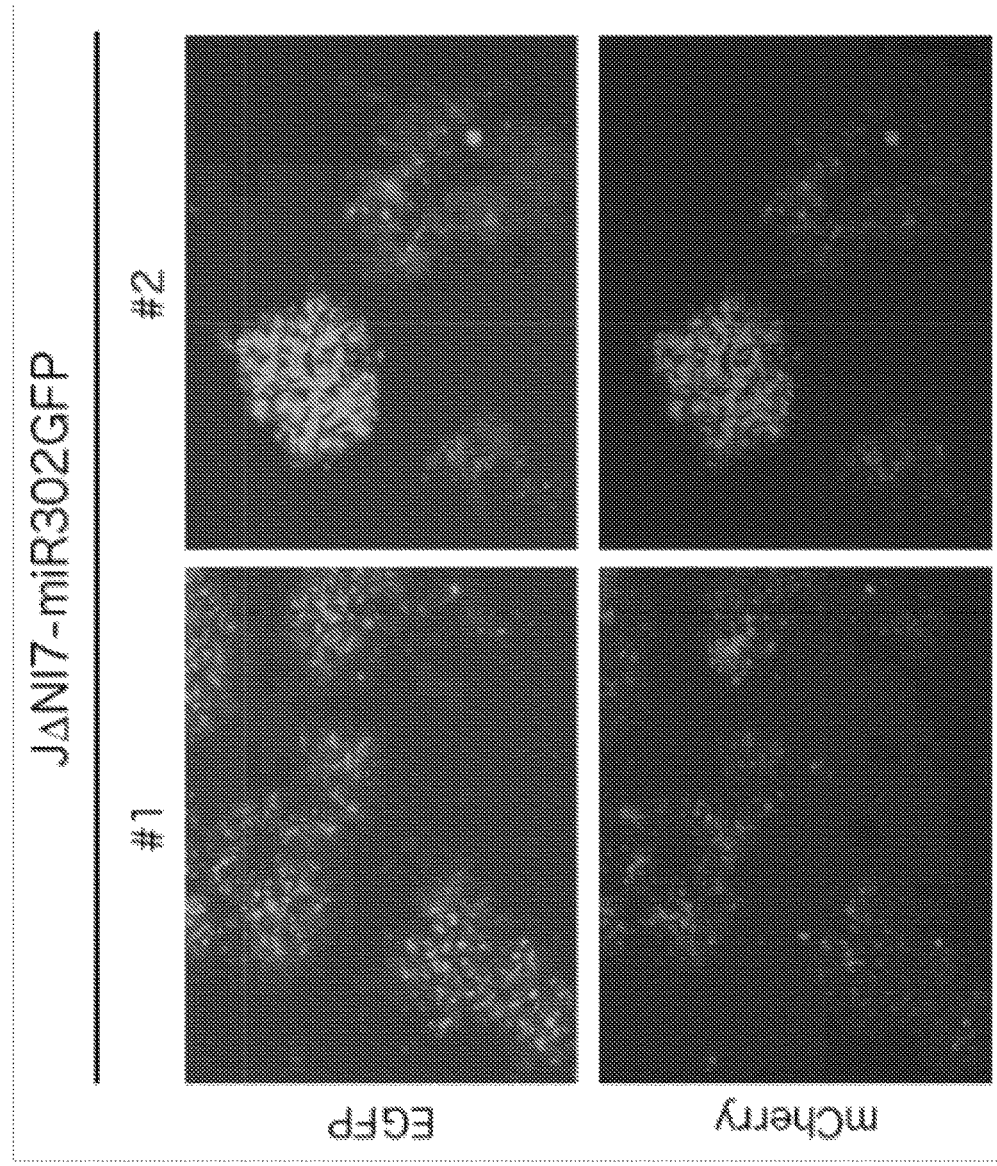
FIG. 3 is a set of photographs showing expansion of JΔNI7-miR302GFP virus on complementing (U2OS-ICP4/ICP27) cells. Photographs were taken at 3 days post-infection.

The JΔNI7-miR302GFP BAC construct carries in the LAT locus an expression cassette for the miR302s/367 cluster (Anokye-Danso, *Cell Stem Cell*, 8: 376-388 (2011)) as an alternative for the typical Yamanaka somatic cell reprogramming gene cocktail (OKSM: Oct4, Klf4, Sox2, c-Myc) (Takahashi and Yamanaka, *Cell*, 126: 663-676 (2006); Takahashi, *Cell*, 131: 861-872 (2007). The miR302s/367 gene cluster is located in an intron connecting the EF1α promoter to the GFP coding sequence. Two isolates of JΔNI7-miR302GFP BAC DNA were purified and introduced into U2OS-ICP4/ICP27 cells to produce virus particles for examination of virus growth and transgene expression. On observation of 90% cytopathic effect in the cultures, virus was collected from cells and supernatants and used to infect fresh U2OS-ICP4/ICP27 cells. Transgene expression and virus spread were then monitored daily. As shown in FIG. 3, at three days post infection, both BAC isolates produced plaque-forming virus and both viruses expressed EGFP and mCherry.

Example 6

This example describes the construction of a targeting plasmid for insertion of a tetracycline-inducible promoter and Gateway recombination cassette into the LAT locus of a HSV vector.

Different strategies may be used to prevent genetic rearrangement and inactivation of an OKSM expression cassette during virus expansion, where the cassette has been inserted into the LAT locus of JΔNI5 or JΔNI8. One of these strategies is to replace the constitutively active CAG promoter of the OKSM cassette with a tetracycline-inducible promoter. Because the tetracycline-inducible promoter is only active in the presence of both its transactivator (rtTA) and tetracycline/doxyxycline, transgene expression can be tightly regulated (repressed) during virus expansion.

Figure 4:
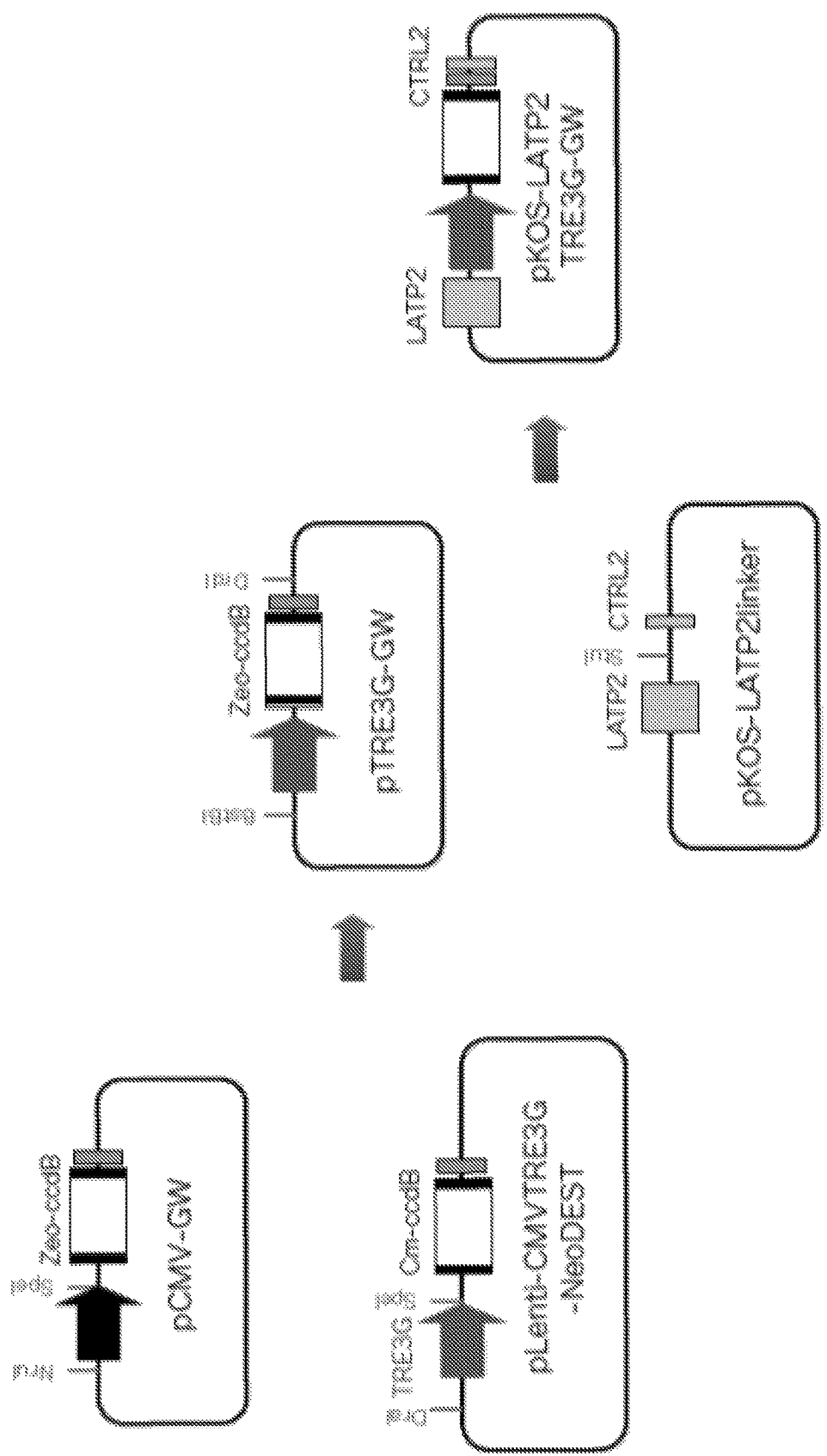
FIG. 4 is a schematic of the construction of a targeting plasmid for insertion of a tetracycline-inducible promoter and Gateway recombination cassette into the LAT locus of a HSV vector.

A targeting plasmid for insertion of the tetracycline-inducible promoter into the LAT locus was developed (FIG. 4). A lentivirus construct (pLenti-CMVTRE3G-NeoDEST, Addgene) carrying the tetracycline-inducible TRE3G promoter was used as a starting construct. The TRE3G promoter was isolated from pLenti-CMVTRE3G-NeoDEST as a DraI-SpeI fragment and inserted between the NruI and SpeI sites of plasmid pCMV-GW, replacing the resident CMV promoter. Plasmid pCMV-GW contained a zeocin (Zeo)-selectable gene in the Gateway (GW) cassette instead of the chloramphenicol (Cm)-selectable gene in GW of the lentiviral plasmid. The TRE3G-GW (Zeo) expression cassette was isolated and cloned between LAT sequences in a plasmid containing a portion of the LAT locus to add "homology arms" to the TRE3G-GW (Zeo) cassette for recombination into BAC DNA.

Example 7

This example demonstrates immunofluorescence staining and a complementation assay for ICP27.

Figure 6A:
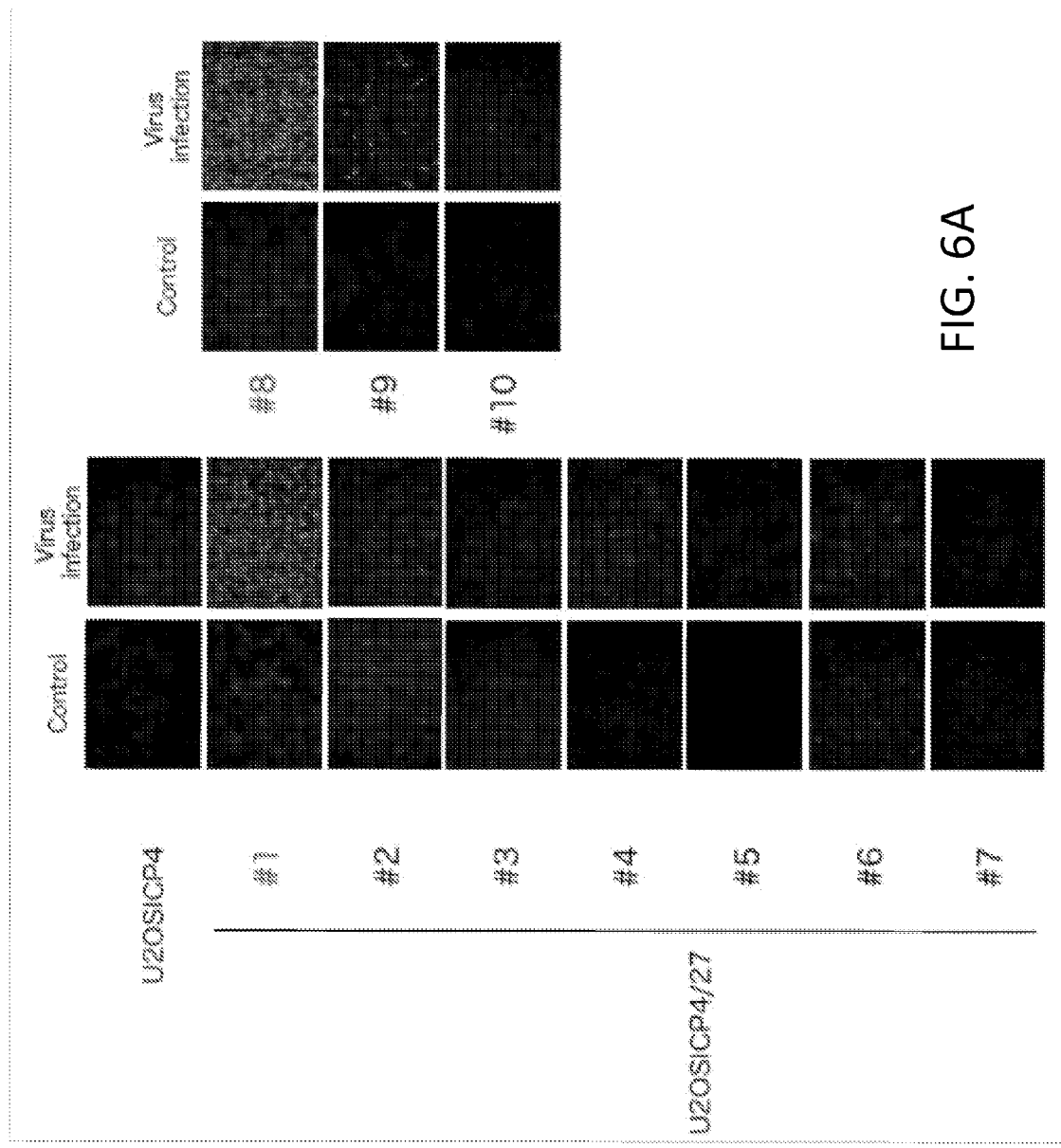
FIG. 6A is a set of photographs showing ICP27 immunofluorescence staining of U2OS-ICP4 cells and different clonal U2OS-ICP4/ICP27 cells infected with QOZHG virus (ICP4-null; ICP27-null).
Figure 6B:
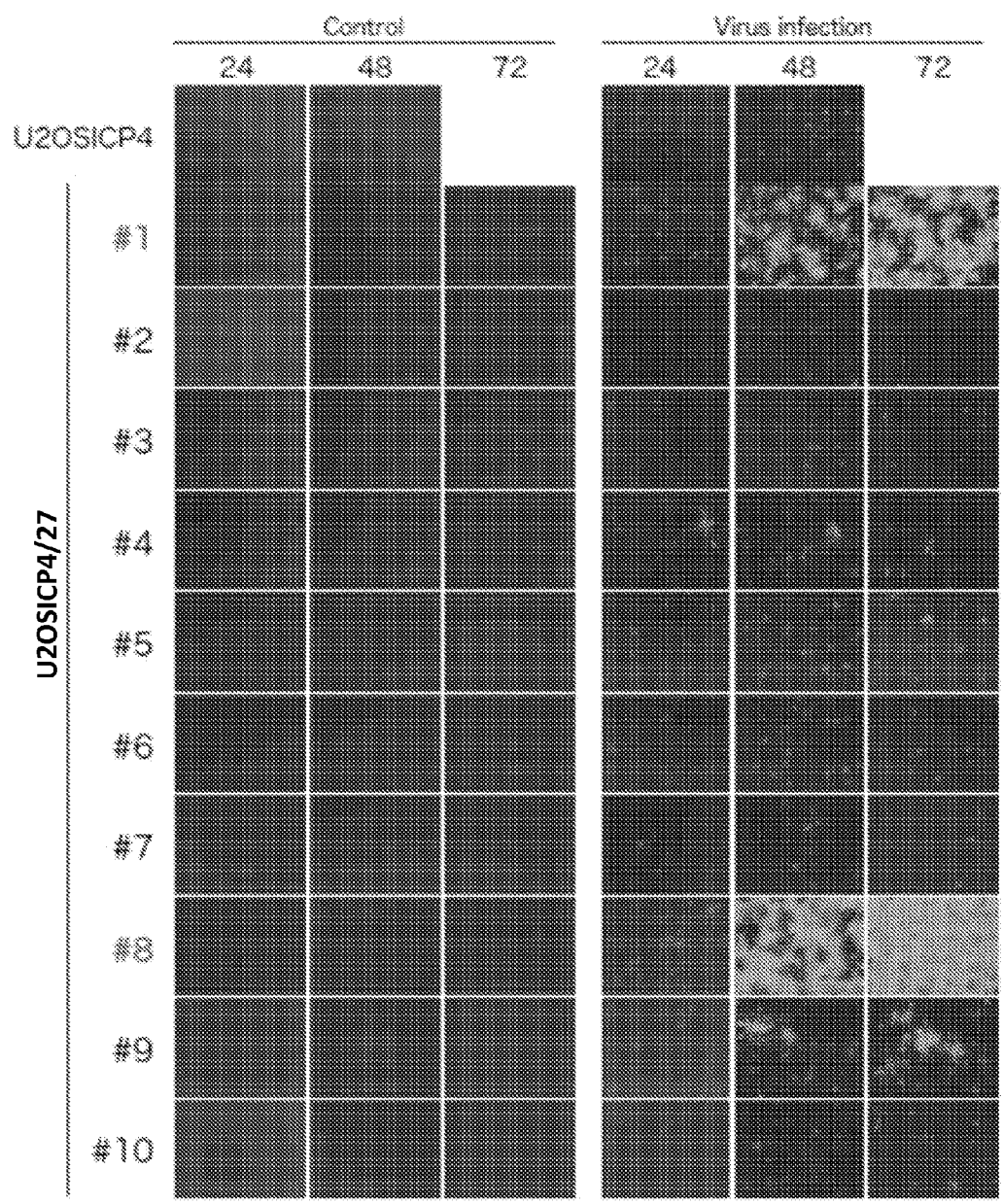
FIG. 6B is a set of photographs showing the growth of the QOZHG virus (GFP expression from an HCMV promoter-GFP cassette in the viral genome) in U2OS-ICP4 and U2OS-ICP4/ICP27 cells.

U2OS-ICP4 cells and individual clones of ICP27 lentivirus-infected U2OS-ICP4 cells selected for acquisition of resistance to blasticidin were infected with QOZHG virus (ΔICP4, ΔICP27::HCMV IEp-GFP, β-ICP22, β-ICP47, AUL41::ICP0placZ; Chen, *J. Virol.*, 74: 10132-10141 (2000)) at MOI of 0.5 for ICP27 immunofluorescence staining and 0.01 for the complementation assay. For ICP27 immunofluorescence staining, the cells were fixed and stained 24 hours post-infection (FIG. 6A). Clones #1 and #8 showed robust induction of ICP27 expression by ICP27-deficient HSV (QOZHG) infection. For the complementation assay, virus growth was monitored, and photographs were taken at 24, 48, and 72 hours post-infection (FIG. 6B). U2OS-ICP4/27 clones #1 and #8 showed and the strongest ability to support QOZHG virus growth.

Example 8

This example demonstrates the construction and testing of several HSV vectors.
Materials and Methods
Cells Human osteosarcoma U2OS cells (ATCC, Manassas, Va., USA) were grown in DMEM with 10% FBS and penicillin-streptomycin (P/S). Human neonatal dermal fibroblasts (HDFs) (ATCC, PCS-201-010) and BJ human foreskin fibroblasts (ATCC, CRL-2522) were grown in DMEM with 10% Embryonic Stem Cell Qualified FBS (Invitrogen) and P/S. Vero, Vero-7b (Krisky et al., *Gene Ther.* 5, 517-30 (1998)) and 293T cells were cultured in DMEM containing 5% FBS and P/S. Human hepatocytes (hHEP) were isolated and cultured as described (Ueki et al., *Hepatology* 54, 216-28 (2011); Yoshida et al., *Hepatology* 58, 163-75 (2013)). Human subcutaneous preadipocytes (hPAD) (PT-5020, Lonza) were maintained with PBM™-2 Basal Medium (Lonza). Human muscle-derived stem/progenitor cells (hMDSCs) were cultured as described (Gao et al., *Cell Transplant* 22, 2393-408 (2013)). Human neonatal keratinocytes (hEK) (Invitrogen) were cultured in EpiLife® Medium supplemented with Human Keratinocyte Growth Supplement (both from Invitrogen). Dorsal root ganglia (rDRGs) were micro-dissected from day 15 rat embryos, dissociated with 3 mg/ml type-I collagenase (Sigma, St. Louis, Mo.) in Leibovitz's L-15 media for 30 min at 37° C. with constant shaking, and plated on poly-D-lysine (Sigma)-coated coverslips at approximately $10^5$ cells/well in 24-well plates in 500 μl defined Neurobasal medium with B27 supplement, Glutamax-I, Albumax-II, and P/S (Gibco/Invitrogen, Grand Island, N.Y.), supplemented with 100 ng/ml 7.0S NGF (Sigma). At 1-3 d post plating, cultures were treated with 10 μM uridine and 10 μM fluorodeoxyuridine (Sigma) in the above media for 1-2 d to limit the expansion of dividing cells such as fibroblasts and glia. Cells were then washed with PBS and incubated with NGF-supplemented Neurobasal medium as above. Virus infections were performed at 10-15 d after plating.

U2OS-ICP4 cells were generated by infection of U2OS cells with purified ICP4 lentivirus (see below), isolation of puromycin-resistant clones (2 mg/ml), and immunofluorescence screening for ICP4 expression after infection with ICP4-deficient virus (QOZHG) at a multiplicity (MOI) of 0.5. U2OS-ICP4/27 cells were similarly generated by infection of U2OS-ICP4 cells with purified ICP27 lentivirus, selection for resistance to puromycin and blasticidin (10 mg/ml), and screening of QOZHG-infected clones for ICP27 immunofluorescence and virus growth (FIG. 6).

Lentiviruses

Figure 5:
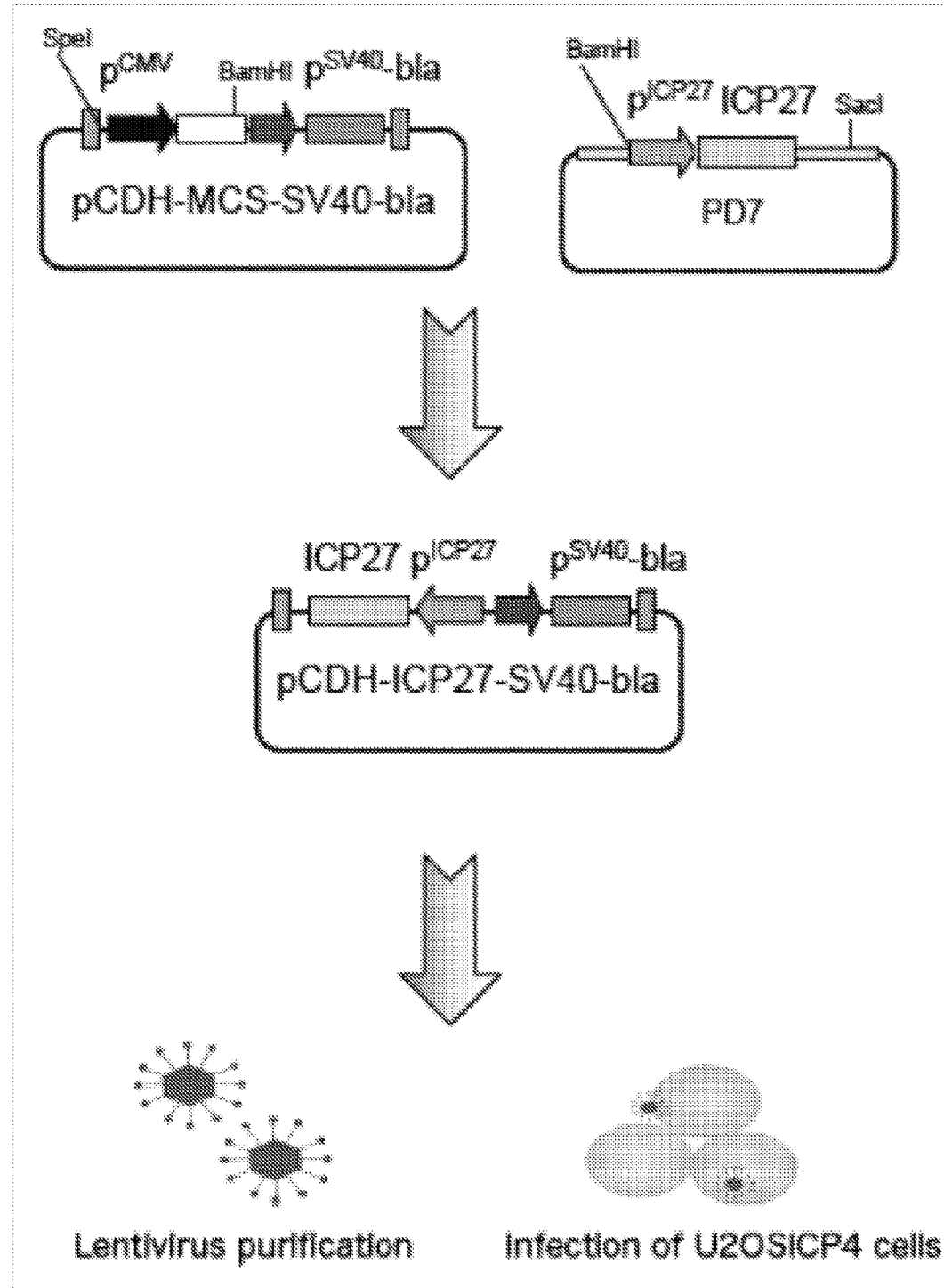
FIG. 5 is a schematic of the construction of a lentivirus plasmid for expressing ICP27 in a U2OS-ICP4 cell line.

Lentiviral ICP4 expression plasmid pCDH-ICP4-puro was constructed by replacing the complete HCMV IE promoter of plasmid pCDH-CMV-MCS-EF1-Puro (Systembio) with the ICP4 promoter and coding region from plasmid S3 which consists of the SphI fragment from pICP4-lox-pac (Rasty et al., *J. Neurovirol.* 3, 247-64 (1997)) (GenBank JQ673480.1 HSV-1 KOS map positions 131,587-124,379; D. Krisky and J. C. G., unpublished) inserted in the SphI site of pUC19. Lentiviral ICP27 expression plasmid pCDH-ICP27-SV40-bla was constructed, first, by replacement of the puromycin-resistance cassette of pCDH-CMV-MCS-EF1-Puro with the blasticidin-resistance cassette of pcDNA6/BioEase™-DEST (Invitrogen) to create pCDH-CMV-MCS-SV40-bla (FIG. 5). The ICP27 promoter and coding region were then isolated by digestion of plasmid PD7 containing the ICP27 gene and flanking sequences between EcoRV and SacI sites (GenBank JQ673480.1 map positions 110,580-115,666; D. Krisky and J. C. G., unpublished) with BamHI (map position 113,244) and SacI, and the isolated fragment was used to replace the CMV promoter in pCDH-CMV-MCS-SV40-bla. The resulting plasmid, pCDH-ICP27-SV40-bla, is depicted in FIG. 5.

Lentiviruses were produced using the ViraPower™ Lentiviral Packaging Mix (Invitrogen) according to the manufacturer's instructions. Briefly, 293T cells were transfected with pCDH-ICP4-puro or pCDH-ICP27-SV40-bla in ViraPower™ mix. Supernatants were harvested 2 d later, clarified, filtered through a 0.45 µm filter, and concentrated by centrifugation. Lentiviruses produced from pCDH-ICP4-puro are referred to herein as ICP4 lentivirus; lentiviruses produced from pCDH-ICP27-SV40-bla are referred to as ICP27 lentivirus.

HSV-BAC Engineering

All HSV-BAC constructs generated in this study and converted to virus particles are listed in Table 2 and were derived from KOS-37 BAC (24), a kind gift from D. Leib (Dartmouth Medical School, NH). All BAC engineering was performed by scarless Red recombination with pRed/ET (Gene Bridges, Heidelberg, Germany) and either pBAD-I-sceI plasmid (kindly provided by N. Osterrieder, Free University of Berlin, Germany) or in *E. coli* strain GS 1783 (from G. Smith, Northwestern University, Chicago, Ill.), as described (Tischer et al., *Methods Mol. Biol.* 634, 421-30 (2010); Tischer et al., *Biotechniques*, 40, 191-97 (2006)), or by in vitro Gateway (GW) recombination according to the Gateway Technology Manual (Invitrogen) (http://tools.lifetechnologies.com/content/sfs/manuals/gateway-man.pdf). All constructs were confirmed by PCR analysis, FIGE analysis of restriction enzyme digests, and targeted DNA sequencing. Targeting plasmids for Red recombination were constructed as described (Tischer et al., *Biotechniques*, 40, 191-97 (2006)). The kanamycin-resistance gene flanked by an I-SceI restriction site (I-SceI-aphAI fragment) was amplified from pEPkan-S2 (from N. Osterrieder) (Tischer et al., *Biotechniques*, 40, 191-97 (2006)) by PCR with the different targeting primers specified below and listed in Table 1. Primer portions targeting the viral genome were designed based on the sequence of HSV-1 strain-17 (GenBank JN555585.1). All targeting fragments for Red recombination were purified by Qiagen gel extraction kit (Qiagen) or SpinSmart Nucleic Acid Prep & Purification Columns (Denville Scientific). Nucleotide positions provided below refer to the GenBank JQ673480 sequence of HSV-1 strain KOS.

To construct the JΔNI vectors, the previously described hyperactive N/T double mutation was introduced into the gB gene (Uchida et al., *J. Virol.*, 84, 12200-09 (2010)) of KOS-37 BAC and the internal repeat (joint) region was deleted. The I-SceI-aphAI fragment was cloned into the SnaBI site of plasmid pgB1:D285N/A549T (Uchida et al., J. Virol., 84, 12200-09 (2010)). The resulting plasmid, pgB: N/T-kan, was used as template for amplification with primers 61 and 62 (Table 1), and the product was recombined with the native gB gene of KOS-37 BAC followed by I-SceI-enhanced deletion of the aphAI gene in pBAD-I-sceI plasmid-transformed bacteria. Next, I-SceI-aphAI was amplified with nested forward primers 46, 48 and reverse primer 47 for Red-mediated deletion of the joint region (GenBank JQ673480 positions 117,080-132,466) along with the first 14 nucleotides (nts) of the adjacent unique short ($U_S$) segment of the genome, followed by removal of the aphAI gene. $U_S$ in KOS-37 BAC is in the reverse orientation relative to the typical representation of the HSV genome, placing the $U_S12$ (ICP47) gene directly adjacent to the joint and the $U_S1$ gene adjacent to the $U_S$ terminal repeat. The 14-nt deletion beyond the joint (GenBank JQ673480 positions 145,377-145,390) thereby removed the ICP47 translation initiation codon.

Replacement of the ICP4 locus in the joint-deleted gB:N/T BAC with an mCherry expression cassette was achieved as follows. Plasmid pUbC-mCherry-SV40 pA was constructed by cloning of the human ubiquitin C promoter (UbCp) from pBluescriptUB-Flag-mArt (a gift from H. Nakai, Oregon Health & Science University, Portland, Oreg.), the mCherry gene from pEP-miR (Cell Biolabs, San Diego, Calif.), and the SV40 polyadenylation (polyA or pA) region from pEP4-EO2SCK2M-EN2L (Addgene plasmid 20924) (Yu et al., *Science* 324, 797-801 (2009)) into pBluescript KS+ (Stratagene). The I-SceI-aphAI fragment was then cloned into the BamHI site of pUbC-mCherry-SV40 pA at the boundary between UbCp and mCherry to generate pUbC-mCherry-SV40 pA-KAN. The insert was PCR amplified with primers 51 and 52 (Table 1) for Red-mediated recombination with the ICP4 target locus. The resulting construct was deleted for HSV-1 KOS positions 146,113-151,581 of the GenBank JQ673480 sequence, including the TAATGARAT motifs of the ICP22 promoter.

Replacement of the ICP0 and ICP27 IE promoters with the early (β) HSV-1 thymidine kinase (TK) promoter to generate JΔNI2 was performed by PCR through the TK promoter in front of both the ICP0 and the ICP27 coding region in the JΔββ virus genome (Craft et al., *Stem Cells* 26, 3119-29 (2008)) with nested primer pairs 81/82 and 83/84, respectively, cloning of the product of each reaction into pCRblunt (Invitrogen) to produce pCRBlunt-β0 and pCR-Blunt-β27, respectively, insertion of I-Sca-aphAI into the BglII site of pCRBlunt-β0 and the HpaI site of pCRBlunt-β27 yielding pCRBlunt-30-KAN and pCRBlunt-β27-KAN, and PCR amplification of the inserts with primer pairs 85/86 and 87/88, respectively, for Red recombination with the joint-deleted UbCp-mCherry gB:N/T BAC. JΔNI3 was then derived from JΔNI2 by Red-mediated clean deletion of the ICP0 coding sequence using nested targeting forward primers 41, 42 and reverse primer 43 for I-SceI-aphAI amplification. JΔNI5 was likewise derived from JΔNI3 by clean deletion of the ICP27 coding sequence using primer pair 44/45 to produce the targeting I-Sca-aphAI fragment.

JΔNI6-CAGGFP was generated by insertion of an EGFP expression cassette between the UL3 and UL4 genes of JΔNI5. First, plasmid pCAG-GFP was constructed by replacing the gH gene between the CAG promoter (CMV enhancer/chicken beta-actin promoter/chimeric intron) and rabbit β-globin polyA region in plasmid pPEP100 (a gift from P. Spear, Northwestern University) (Pertel et al., *Virology* 279(1), 313-24 (2001)) with the EGFP gene from pEGFP-C1 (Clontech). I-SceI-aphAI was then inserted into the SnaBI site of pCAG-GFP to create plasmid pCAG-GFPKAN. Separately, multi-step PCR using KOS-37 BAC DNA as initial template was performed to generate a fragment that contained novel cloning sites (MCS) between the UL3 and UL4 polyA regions, as follows. First, extension PCR was performed to amplify the 3' UTRs of UL3 and UL4 with primer pairs 57/58 and 59/60, respectively, that added an overlapping MCS region to each 3'UTR fragment. The 2 PCR products were gel-purified and 100 ng of each was used for overlapping PCR with primers 57 and 59 to create a continuous fragment. This product was cloned into pCR-Blunt (Invitrogen), yielding plasmid pCRBluntUL3-4linker. The insert of pCAG-GFPKAN was then cloned between the AccI and PsiI sites in the MCS of pCRBluntUL3-4linker. The resulting plasmid was digested with MfeI and PpuMI and the UL3-CAG-GFPKAN-UL4 fragment was isolated for recombination with the UL3-UL4 intergenic region of JΔNI5 followed by aphAI gene removal.

To create JΔNI7GFP, an XhoI fragment (~6.2 kb) containing the 2 CTRLs, LAP1 and LATP2 of the HSV-1 LAT locus was isolated from KOS-37 BAC DNA and cloned into pBluescript KS+. An internal KpnI-SalI fragment extending from near the end of LATP2 to ~250 bp downstream of CTRL2 was isolated from this recombinant and cloned between the KpnI and SalI sites of pSP72 (Promega) to produce pSP72KOS-LAT. A multicloning site was then introduced between 2 BstXI sites located ~240 and ~430 bp downstream of the KpnI site, yielding pSP72KOS-LATlinker. Separately, plasmid pCAG-GW was constructed by replacing the gH gene of pPEP100 (Pertel et al., *Virology* 279(1), 313-24 (2001)) with a PCR-amplified modified GW recombination cassette [GW-Zeo; zeocin resistance instead of chloramphenicol resistance (Wolfe et al., *J. Virol.* 84, 7360-68 (2010))]. The insert of pCAG-GW was then cloned into the MCS of pSP72KOS-LATlinker to produce pSP72KOS-LATlinker-GW. The plasmid was digested with KpnI and HpaI to isolate the CAG-GW region with flanking LAT sequences for Red-mediated recombination with the LAT locus of JΔNI5 in ccdB-resistant HerpesHogs bacteria (Wolfe et al., *J. Virol.* 84, 7360-68 (2010)). Finally, the GW cassette in the resulting JΔNI5 recombinant BAC was replaced with the EGFP gene by Red-mediated recombination with an AatII-PsiI fragment, including CAG and polyA sequences, of plasmid pCAG-GFPKAN. JΔNI7GFP derivatives deleted for specific LAT region elements outside the EGFP cassette (CTRL1, CTRL2, LATP2) were generated by Red-mediated recombination of JΔNI7GFP DNA with targeted I-SceI-aphAI cassettes produced by PCR with the respective F1, F2 and R primers listed in Table 1 (63-65, 66-68, and 69-71, respectively).

For the construction of the different JΔNI9 and JΔNI10 vectors, the ~6.2-kb LAT XhoI fragment described above was deleted from the JΔNI5 genome by recombination with LAT-targeted I-SceI-aphAI generated by PCR with primers 78, 79 and 80, producing JΔNI5ΔL. GW-Zeo was then amplified with targeting primers for the intergenic region between UL45 and UL46 (74/75) or UL50 and UL51 (76/77) and the product of each reaction was recombined with JΔNI5ΔL BAC DNA to create JΔNI9GW and JΔNI10GW. JΔNI7GFP BAC DNA was digested with XhoI and the ~7.2-kb CAG-GFP-containing fragment from the LAT locus was isolated and cloned into pENTR1A (pENTR-LAT-XhoI). The corresponding ~5.3-kb XhoI fragment of JΔNI7GFPΔC12LP2 was likewise isolated and cloned into pENTR1A (pENTR-LATA-XhoI) and lastly, the insert of pCAG-GFP (see above) was transferred into pENTR1A (pENTR-CAG-GFP). In vitro LR Clonase (Invitrogen) reactions were then performed to recombine the different pENTR constructs with JΔNI10GW BAC DNA, producing JΔNI10LAT-GFP, JΔNI10DC12LP2-GFP and JΔNI10GFP, respectively, and pENTR-LAT-XhoI and pENTR-CAG-GFP were recombined with JΔNI9GW BAC DNA to generate JΔNI9LAT-GFP and JΔNI9GFP.

KNTc was constructed by introduction of the gB:N/T mutations into KOS-37 BAC as described above and the UbCp-mCherry cassette into the intergenic region between UL3 and UL4 locus of KOS-BAC by Red recombination with I-SceI-aphAI targeted by amplification with primers 53 and 54.

Viruses

JΔNI BAC DNAs were converted to infectious viruses by transfection of U2OS-based complementing cells. DNA in 500 µl OptiMEM (Invitrogen) was incubated with 1 µl Lipofectamine Plus Reagent (Invitrogen) for 5 min at room temperature, 6.25 µl Lipofectamine LTX (Invitrogen) was added, the mixture was incubated for 30 min at room temperature and added to cells. After incubation at 37° C. for 6 h, the transfection mix was removed and the cells were cultured overnight at 37° C. with serum-free DMEM, transferred to a 33° C. incubator, and monitored for 100% cytopathic effect (CPE). Supernatants were titered and then amplified by infection of sequentially larger cultures at a multiplicity (MOI) of 0.001 PFU/cell. KNTc infectious virus was produced by transfection of Vero cells using 3 Lipofectamine Plus Reagent and 9 µl Lipofectamine LTX for 4 h at 37° C.; an MOI of 0.01 PFU/cell was used for KNTc virus amplification on Vero cells. Complementing cells for transfections and/or virus growth were as follows: U2OS-ICP4 (JΔNI2, JΔNI3), U2OS-ICP4/27 (JΔNI5 and derivatives), and Vero-7b [QOZHG virus (ΔICP4, ΔICP27:: HCMV IEp-GFP β-ICP22, β-ICP47 and ΔUL41::ICP0p-lacZ) (Chen et al., *J. Virol.* 74, 10132-41 (2000))]. All virus stocks were titered on U2OS-ICP4/27 cells (Table 2). Physical titers [genome copies (gc)/ml] were determined by quantitative real-time PCR as described below. Fluorescent images of infected cells were obtained with a Nikon Diaphot fluorescence microscope (Nikon, Melville, Pa.) at 40× magnification.

Virus Growth Curves

Replicate wells of Vero-7b, U2OS, U2OS-ICP4 and U2OS-ICP4/27 cells in a 24-well plate were infected at a multiplicity (MOI) of 0.001 for 2 h, treated with 0.1 M glycine (pH 3.0) for 1 min to inactivate extracellular virus, and incubated at 37° C. and 5% $CO_2$. Media were harvested daily and titered by standard plaque assay on U2OS-ICP4/27 cells.

Cytotoxicity Assay $5×10^3$ HDF and Vero cells were seeded in a 96-well plate and infected with KOS, QOZHG or JΔNI viruses at 25,000 gc/cell. Cell viability was determined 5 d later by MTT assay essentially as described (Uchida et al., *J. Virol.* 87, 1430-42 (2013)).

Western Blotting and Immunofluorescence

Cell lysate preparation and Western blotting were performed as described (Miyagawa et al., *PLoS One* 4, e4634

(2009)). Polyclonal rabbit anti-ICP0 antibodies were produced in our laboratory, anti-ICP27 (10-H44) was from Fitzgerald Industries International (Concord, Mass.), anti-ICP22 was a gift from John Blaho (Mt Sinai School of Medicine, NY), anti-ICP4 (10F1) was from Santa Cruz Biotechnology, and anti-α-tubulin (T6793) was from Sigma. Immunofluorescence using the same ICP4 and ICP27 antibodies was performed essentially as described (Uchida et al., *J. Virol.* 83, 2951-61 (2009)) and was examined under a Nikon Fluorescence microscope.

Quantitative Reverse Transcription-PCR (qRT-PCR) and Genome PCR

For qRT-PCR, total RNA was typically extracted by RNeasy kit (Qiagen). cDNA was synthesized with a RETROscript® Kit (Ambion). Real-time PCR was carried out by the StepOnePlus Real-Time PCR System (Applied Biosystems). For small numbers of cells, a Cells-to-cDNA™ II Kit (Ambion) was used for cell lysis and reverse transcription. Results for 18S ribosomal (r) RNA were used to normalize the data. All qRT-PCR primers used in this study are listed in Table 1.

For the determination of physical (genome copy) titers of virus stocks, 5 ml of virus was incubated with 300 U/ml of Benzonase nuclease (Sigma) for 1 h at 25° C. in the presence of 2 mM $MgCl_2$ and viral DNA was extracted by DNeasy Blood & Tissue Kit (Qiagen). gc titers were determined by qPCR for the glycoprotein D (gD) gene with the gD primers (38/39) and probe (40) listed in Table 1. Amounts of nuclear viral DNA were determined by rinsing the cells at 2 hpi, isolation of nuclei as described (Dignam et al., *Nucleic Acids Res.* 11, 1475-89 (1983); Suzuki et al., *BMC Res. Notes* 3, 294 (2010)), DNA extraction with the DNeasy Blood & Tissue Kit, and qPCR for the gD gene as above. Cellular 18S ribosomal DNA levels were measured with the use of TaqMan® Ribosomal RNA Control Reagents (Invitrogen) and were used to normalize viral DNA amounts.

Statistics

All values are presented as the mean+/−SD. Differences between pairs were analyzed by Student's t test using Microsoft Excel 14.4.1. P values below 0.05 (P<0.05) were considered statistically significant.

Results

Vector Engineering and Virus Growth

Figure 9:
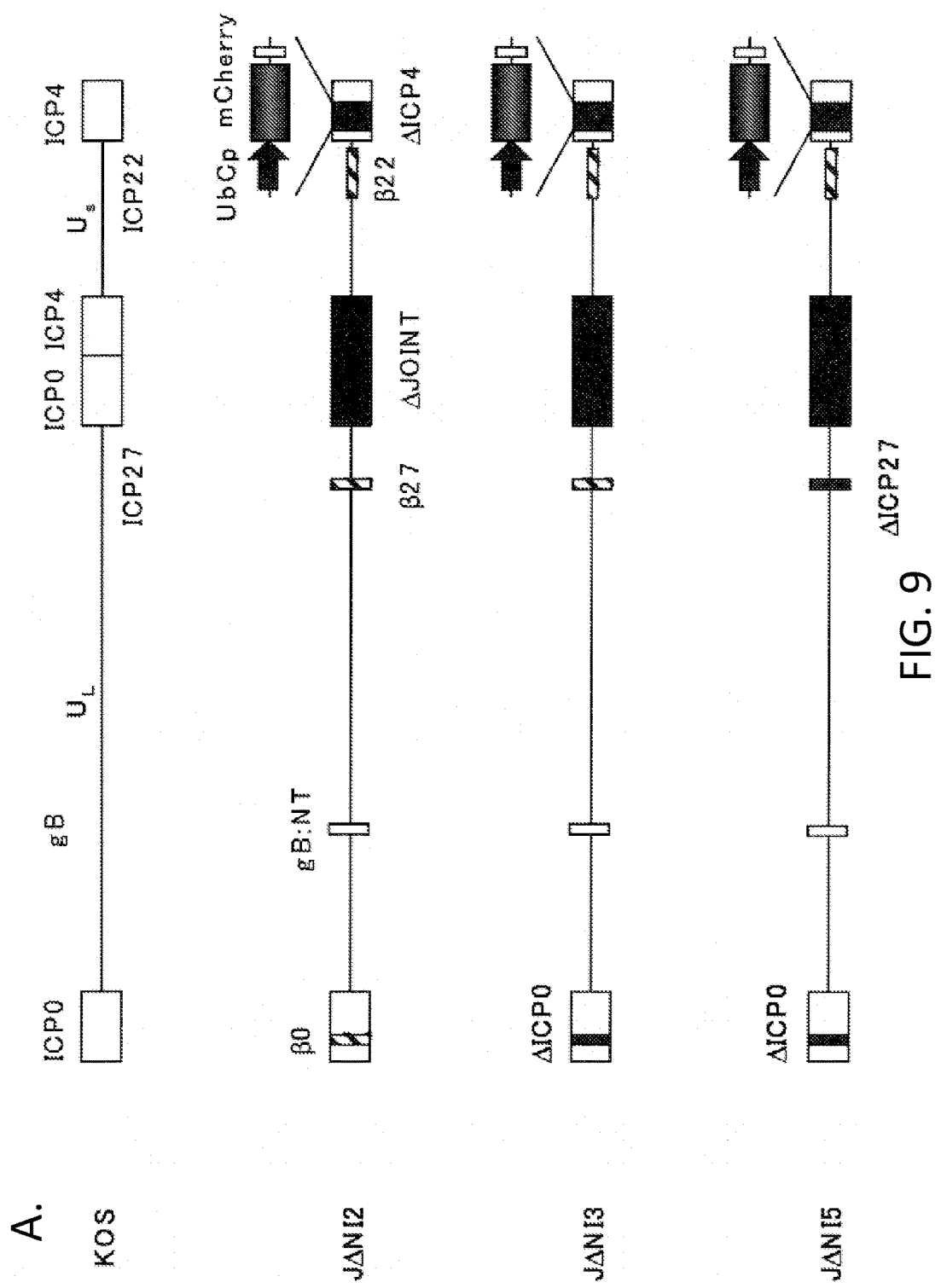
FIGS. 9A-9C. Vector genome structures and complementing cells for virus production.
Figure 9:
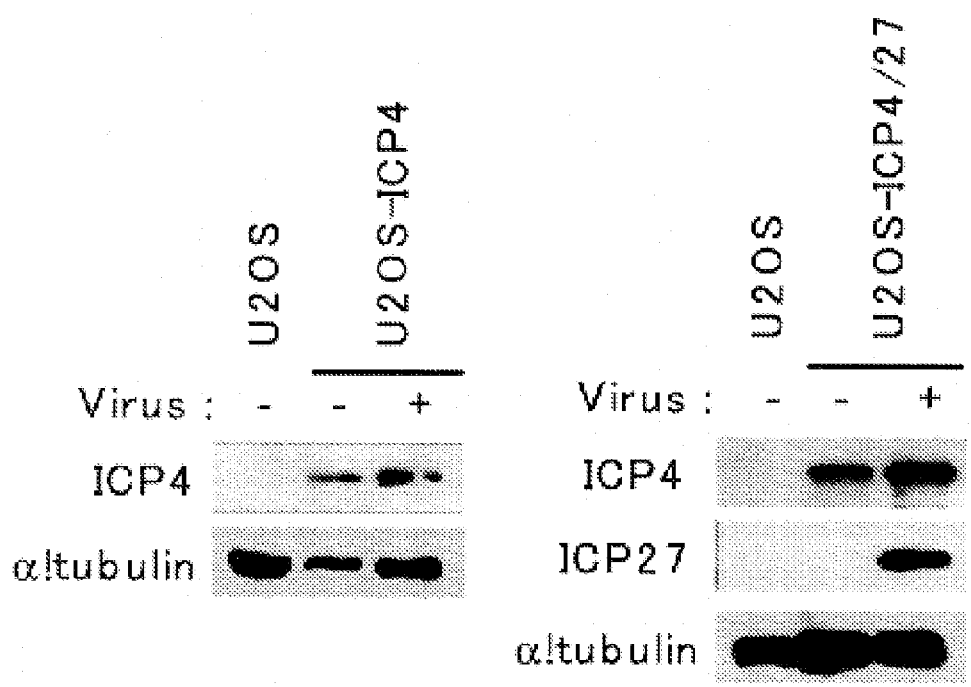
Figure 9:
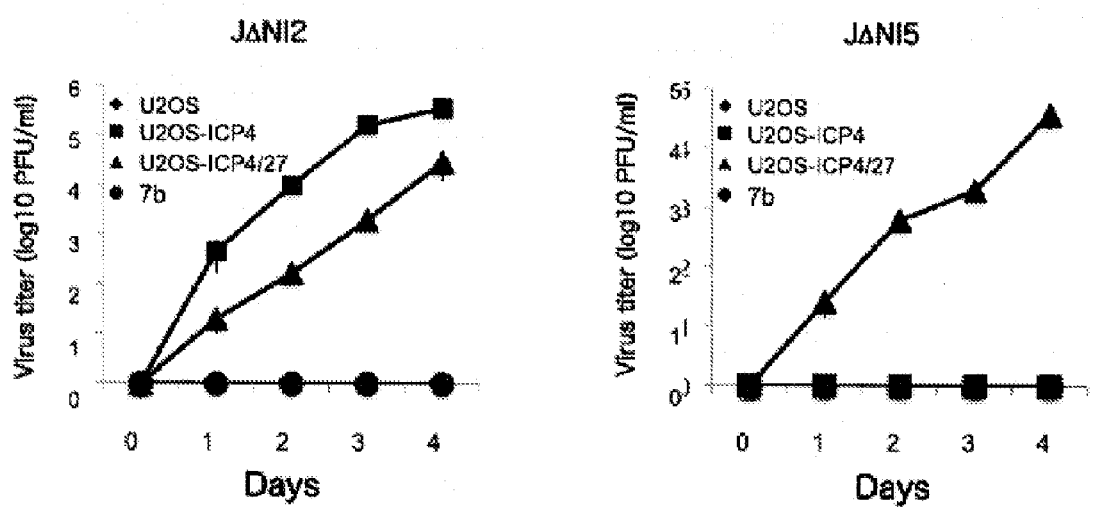

Efficient transduction of mouse embryonic stem cells (mESC) with a defective HSV vector, JDββ, has been reported (Craft et al., *Stem Cells* 26, 3119-25 (2008)), without detectable damage to the cells. JDββ was deleted for the internal repeat region ("joint") of the HSV genome and for two IE genes (ICP4 and ICP22). In addition, the promoters of two other IE genes (ICP0 and ICP27) were replaced with copies of the viral thymidine kinase (TK) early (E or β) gene promoter. JDββ-infected non-complementing cells showed minimal IE gene expression, but the vector was capable of efficient transgene expression in mESC without interference with embryoid body formation or developmental transcription programs. To facilitate the utilization of this vector backbone for diverse gene transfer applications, Red-mediated recombineering was performed in bacteria (Tischer et al., *Biotechniques* 40, 191-97 (2006)) to derive backbone, JΔNI2 (FIG. 9A), from KOS-37 BAC, a bacterial artificial chromosome (BAC) containing the complete genome of HSV-1 strain KOS (Gierasch et al., *Virol. Methods* 135:197-206 (2006)). JΔNI2 was deleted for ICP4 and the joint, including the ICP47 promoter, contained the same ICP0 and ICP27 promoter replacements as JDββ, and the consensus VP16-binding (TAATGARAT) motifs in the ICP22 regulatory region were deleted to change the kinetics of ICP22 expression to that of an early gene. To visualize infection and monitor viral transcriptional activity, an mCherry reporter gene expression cassette was introduced at the position of the deleted ICP4 locus. In addition, the glycoprotein B gene was replaced with a hyper-active allele, gB:N/T (Uchida et al., *J. Virol* 84:12200-9 (2010)), to enhance virus entry into the cells. To eliminate the potential for low-level production of the toxic ICP0 and ICP27 proteins in non-complementing cells, two derivatives of JΔNI2 also were constructed by deletion of the complete coding sequences for ICP0 (JΔNI3) or ICP0 and ICP27 (JΔNI5) (FIG. 9A).

To convert the different JΔNI vector constructs to infectious virus particles, a cell line capable of complementing ICP0, ICP4 and ICP27 was created. Human osteosarcoma U2OS cells naturally complement ICP0 (Yao et al., *J. Virol.* 69, 6249-58 (1995)), eliminating the need to express this toxic protein. U2OS cells were transduced with a lentivirus carrying the ICP4 gene under the control of its own regulatory sequences and a clonal line was isolated that permanently expresses ICP4 (U2OS-ICP4; FIG. 9B). Transduction of these cells with a second lentivirus carrying the ICP27 gene and control region (FIG. 6) was then used to select a cell line, U2OS-ICP4/27, that in addition expresses ICP27 on infection with an ICP4/ICP27-deleted virus (FIG. 9B and FIG. 6). While the abilities of U2OS cells to activate the ICP4 promoter in the absence of the viral VP16 protein and tolerate sustained ICP4 expression were unanticipated, it is unknown whether these features relate to the native ICP0-complementing activity of these cells. DNA from BAC constructs JΔNI2 and JΔNI3 could be converted to infectious virus by transfection of U2OS-ICP4 cells, while DNA from the JΔNI5 construct yielded infectious particles only when transfected into U2OS-ICP4/27 cells (data not shown). FIG. 9C illustrates the growth of JΔNI2 and JΔNI5 viruses initially produced by transfection of U2OS-ICP4 or U2OS-ICP4/27 cells with JΔNI2 or JΔNI5 BAC DNA, respectively. Neither virus could grow on unmodified U2OS cells or on Vero-7b cells that complement ICP4 and ICP27, but not ICP0. JΔNI2 was able to grow on U2OS-ICP4 cells without ICP27 complementation whereas JΔNI5 growth required this additional complementing activity. The stability of the JΔNI5-complementing properties of the U2OS-ICP4/27 cells was tested by plaque assay at different cell passages and no significant decline was observed in plaquing efficiency through at least 20 passages (Table 3). These results were consistent with the engineered IE gene modifications in these viruses and allowed for comparisons of their biological properties.

Standardization of Virus Input

Figure 10:
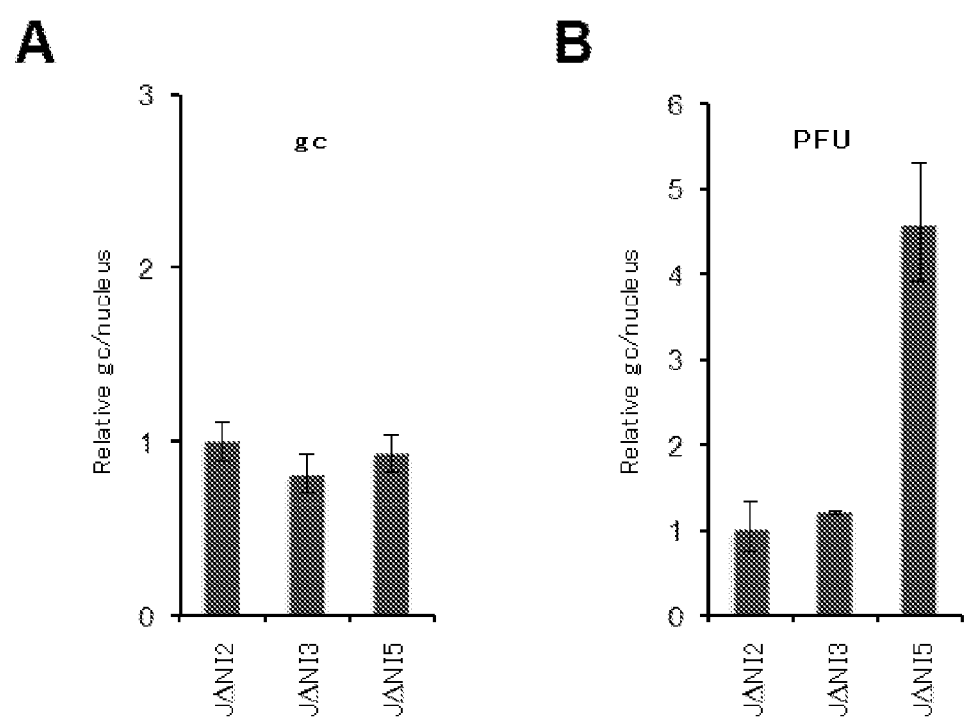
FIGS. 10A-10B. Relative nuclear viral DNA levels after infection with equal gc or PFU. HDFs were infected with the indicated JΔNI vectors at 5,000 gc/cell (FIG. 10A) or 1 PFU/cell (FIG. 10B). At 2 hpi, nuclear DNA was isolated and relative viral gc numbers were determined by qPCR for the gD gene normalized to the cellular 18S rRNA genes.

The relative amounts of each virus needed to deliver equal amounts of viral DNA to the infected cell nucleus was assessed. The biological and physical titers of the various virus stocks were determined by standard plaquing assay on U2OS-ICP4/27 cells and qPCR for the viral glycoprotein D gene, respectively; a difference in genome copy (gc) to plaque-forming units (PFU) ratios of approximately 3-fold was observed between the JΔNI2, JΔNI3 and JΔNI5 virus stocks (Table 2). HDFs were infected with equal PFU or equal gc of the 3 viruses and the number of HSV genomes in the cell nuclei at 2 hours (h) post infection (pi) was determined by qPCR. When equal gc were used for infection, the number of viral genomes in the nuclei at 2 hpi were similar between JΔNI2-, JΔNI3- and JΔNI5-infected cells (FIG. 10A). In contrast, infection with equal PFU resulted in a higher number of JΔNI5 genomes in the nuclei than JΔNI2 or JΔNI3 genomes (FIG. 10B). Thus in the remainder of this study, gc numbers were used to standardize virus input.

Characterization of Vector Properties in Non-Complementing Cells

Figure 11:
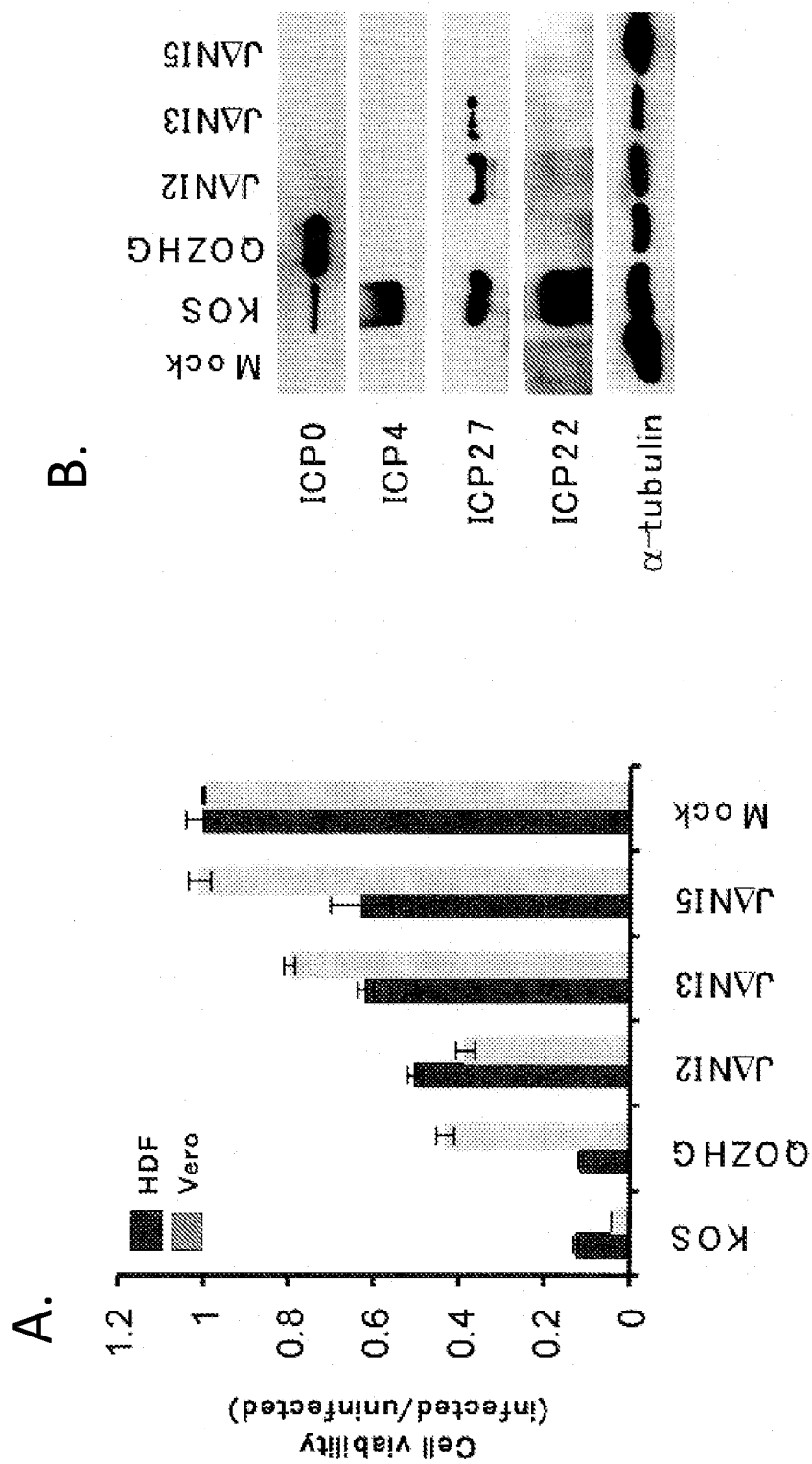
FIGS. 11A-11D. JΔNI cytotoxicity and viral gene expression in non-complementing cells.
Figure 11:
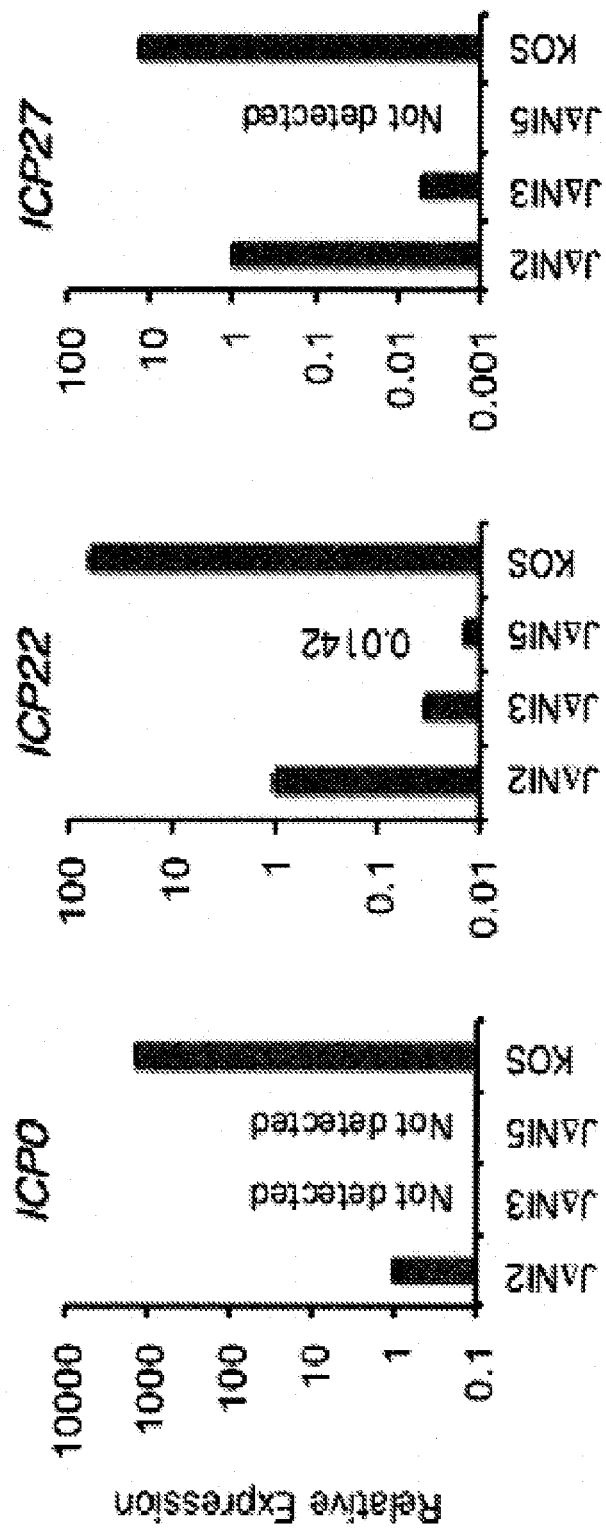
Figure 11:
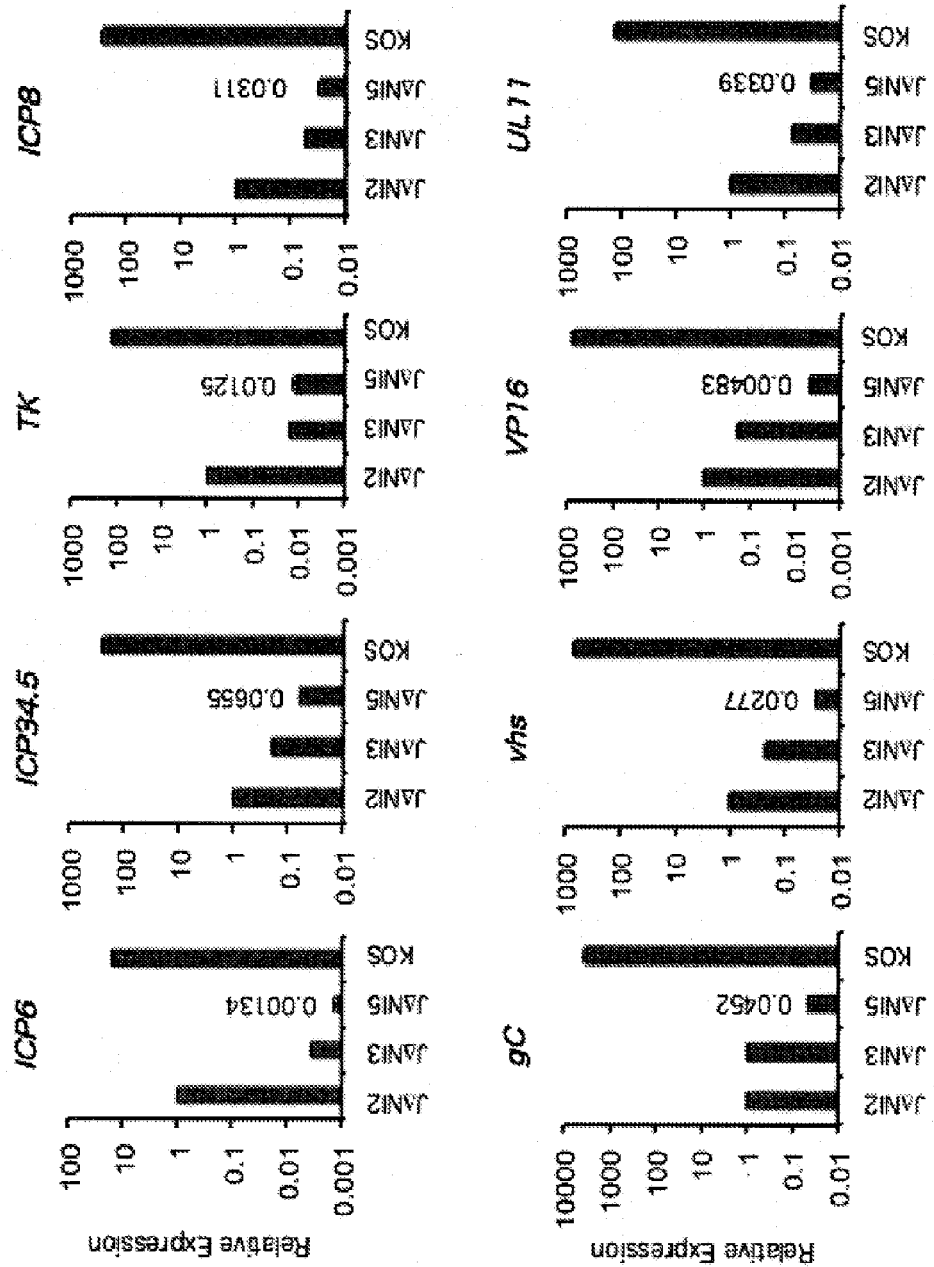

The effects of JΔNI2, JΔNI3 and JΔNI5 infection on the viability of non-complementing HDFs and Vero cells compared with wild-type KOS virus and a previous IE gene-deleted vector, QOZHG (ICP4⁻/ICP27⁻/β-ICP22/β-ICP47; (Chen et al., J. Virol. 74, 10132-41 (2000)) was first examined. At 5 days (d) pi with 25,000 gc/cell, approximately 4-5 times more viable cells remained in the JΔNI-infected HDF cultures than in the KOS- or QQZHG-infected cultures while smaller differences were seen between JΔNI- and QOZHG-infected Vero cells (FIG. 11A). Among the JΔNI viruses, JΔNI2 was somewhat more toxic to HDFs than JΔNI3 (p=0.0017) and 5 (p=0.0430) while toxicity for Vero cells decreased from JΔNI2 to JΔNI3 (p<0.001) to JΔNI5 (p<0.001). To correlate these findings with IE gene expression, Western blots of infected HDFs at 24 hpi were probed with antibodies to 4 of the 5 IE proteins (FIG. 11B). JΔNI2 and JΔNI3 both showed residual ICP27 expression, indicating that the TK promoter in front of the ICP27 gene in both vectors is not silent in these cells, but no IE proteins were detected in JΔNI5-infected cells despite the use of 2-3 fold more gc/cell (equal PFU/cell, see Table 2). The KOS and QOZHG patterns were consistent with the reported down-regulation of ICP0 expression by ICP4 (Douville et al., Virology 207, 107-16 (1995); Resnick et al., J. Virol. 63, 2497-503 (1989)). Using quantitative reverse transcription-PCR (qRT-PCR) analysis, ICP0 mRNA was detected in JΔNI2-infected HDFs and decreasing levels of ICP22 and ICP27 mRNAs between JΔNI2-, JΔNI3- and JΔNI5-infected cells at 12 hpi with equal gc/cell (FIG. 11C). These results suggested that JΔNI2 produced sufficient levels of ICP0 to enhance ICP22 and ICP27 expression and confirmed that progressive deletion of IE genes reduces HSV vector cytotoxicity (Krisky et al., Gene Ther. 5, 1593-603 (1998); Samaniego et al., J. Virol. 72, 3307-20 (1998); Samaniego et al., J. Virol. 71, 4614-25 (1997)).

qRT-PCR was used to examine the expression of selected early and late viral genes (FIG. 11D). At 12 hpi, JΔNI2 generally expressed the highest levels of these genes and JΔNI5 the lowest, similar to the pattern observed for the IE genes. These results showed that substitution of the native ICP0 and ICP27 promoters with an early promoter was not sufficient to silence the viral genome in the absence of ICP4 while deletion of both genes drastically reduced residual gene expression.

JΔNI Reporter Gene Expression

Figure 12:
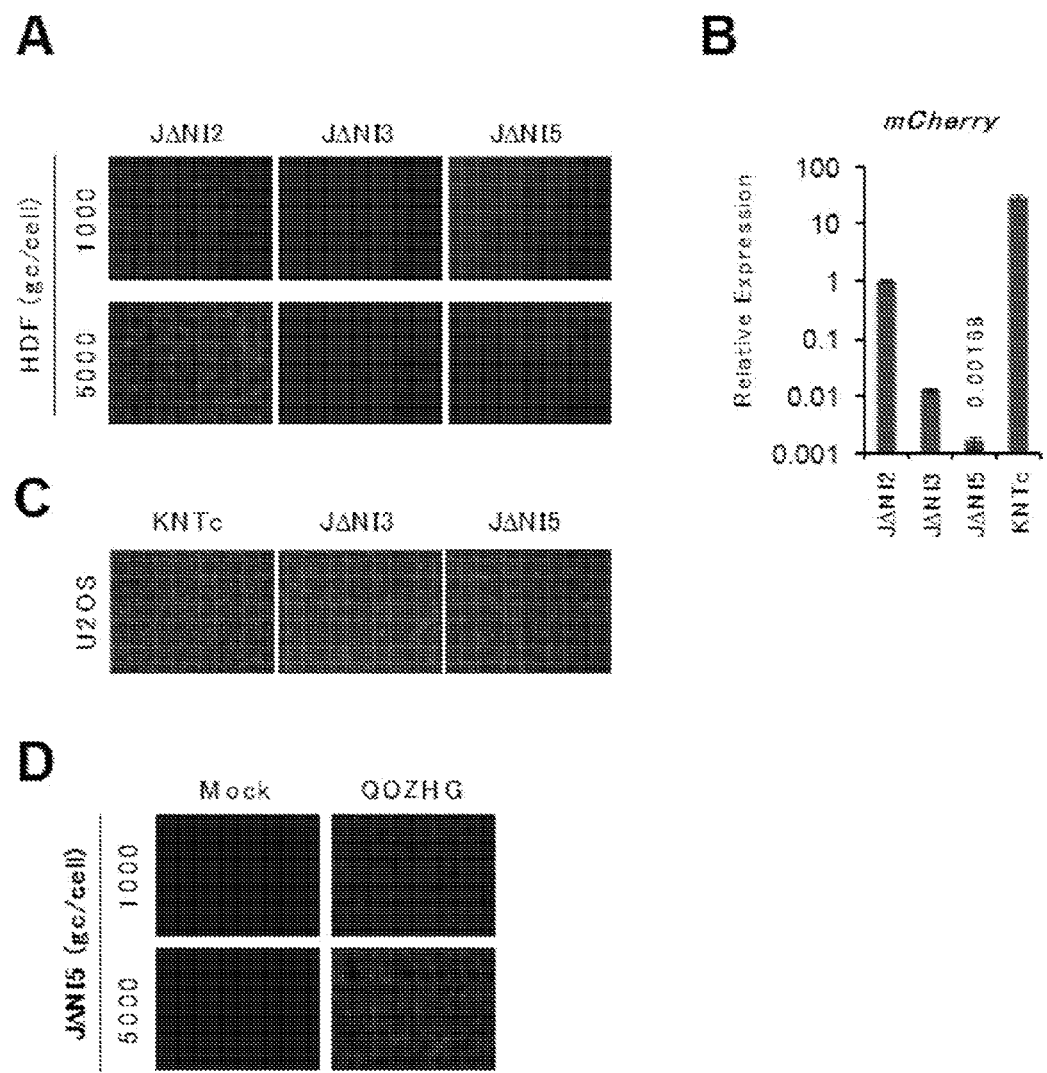
FIGS. 12A-12D. Reporter gene expression in JΔNI-infected HDFs.

To determine whether the activity of the exogenous human ubiquitin C (UbC) promoter (p) introduced with the mCherry reporter gene into the deleted ICP4 locus of the JΔNI vectors was also down-regulated in JΔNI3- and JΔNI5-infected cells compared to JΔNI2-infected cells, mCherry expression in infected HDFs was examined. At 24 hpi with 5,000 gc/cell, mCherry fluorescence was readily detectable in JΔNI2-infected cells but not in JΔNI3- or JΔNI5-infected cells (FIG. 12A). Measurement of mCherry mRNA levels at 6 hpi by qRT-PCR revealed a reduction in transcriptional activity from the UbC promoter of some 100-fold between JΔNI2- and JΔNI3-infected cells, and an additional reduction of approximately 5-fold in JΔNI5-infected cells (FIG. 12B); the KNTc control virus used in this experiment was replication-competent and contained the UbCp-mCherry cassette in the intergenic region between UL3 and UL4. These data were consistent with the interpretation that the residual ICP0 and ICP27 expression from JΔNI2 (FIG. 11C) is sufficient to prevent global transcriptional silencing of the viral genome while deletion of these two genes essentially eliminates all native (FIG. 11D) as well as exogenous (FIG. 12A, 12B) promoter activity. In contrast to HDFs, standard U2OS cells infected with JΔNI3 or JΔNI5 showed strong mCherry expression (FIG. 12C), suggesting that the ICP0-complementing activity of U2OS cells was sufficient to activate these otherwise silent genomes. To confirm that the viral ICP0 protein possessed the same activity, JΔNI5-infected HDFs were superinfected with the ICP0+QOZHG virus (see FIG. 11B). As illustrated in FIG. 12D, superinfection induced mCherry expression, while mock superinfection did not. Together, these results demonstrated that ICP27 was not required to derepress the silent JΔNI5 genome, at least in the presence of abundant ICP0 expression or complementing activity, and suggested that the minimal amount of ICP0 expressed in JΔNI2-infected HDFs sufficed to maintain limited transcriptional activity throughout the viral genome.

High-Level Transgene Expression from the Silent JΔNI5 Genome

Upon infection of neuronal cells, HSV enters a latent state in which the viral genome is transcriptionally silent except for the LAT locus. Whether the LAT locus would similarly remain active in non-neuronal cells in the context of an otherwise silent viral genome was investigated. To this end, an expression cassette consisting of the CAG enhancer/promoter and EGFP gene (CAGp-GFP) was introduced into the LAT 2-kb intron region of JΔNI5, creating a vector construct referred to as JΔNI7GFP (FIG. 13A). As a control, the same CAGp-GFP cassette was introduced into the UL3-UL4 intergenic region of JΔNI5, producing vector JΔNI6GFP (FIG. 13A); the UL3-UL4 intergenic region has been used for non-disruptive insertion of transgene cassettes (Baines et al., J. Virol. 65, 938-44 (1991); Menotti et al., J. Virol. 76, 5463-71 (2002)) and is close to but outside the LAT locus. Elsewhere herein, "JΔNI6GFP" is referred to as "JΔNI6-CAGGFP" (See also FIG. 1A). Infectious viruses were produced on U2OS-ICP4/27 cells and the gc:PFU ratios of the new virus stocks were similar to that of JΔNI5 (Table 2). Both JΔNI6-CAGGFP and JΔNI7GFP produced abundant green and red fluorescence during amplification in U2OS-ICP4/27 cells, confirming the integrity of their transgene expression cassettes. To examine the abilities of these viruses to express the EGFP transgene in non-complementing cells, HDFs were infected with increasing gc/cell and EGFP fluorescence was recorded at 3 dpi (FIG. 13B). JΔNI7GFP-infected cells showed abundant, viral dose-dependent EGFP expression, whereas JΔNI6-CAGGFP infection produced limited expression even at the highest dose. Although a higher virus input was used here than in earlier JΔNI5 infections, mCherry expression remained minimal. These results were confirmed by qRT-PCR measurements of EGFP and mCherry mRNA levels at 3 and 5 dpi (FIG. 13C) and were consistent with the suggestion that the JΔNI6-CAGGFP and JΔNI7GFP virus genomes, like the JΔNI5 genome, were silent in infected HDFs while the LAT locus remained transcriptionally active. Since EGFP mRNA levels in JΔNI7GFP-infected cells were at least as high at 5 dpi as at 3 dpi (FIG. 13C), whether expression could be detected at later times when the cells are fully contact-inhibited was investigated. The results showed that expression could persist for at least 4 weeks in some of the cells (FIG. 13D). Together, these observations indicated that the LAT locus is a privileged site for durable transgene expression from an HSV genome that is non-toxic due to functional deletion of all IE gene expression.

CTRLs and LATP2 Support Transgene Expression from the LAT Locus

Figure 14:
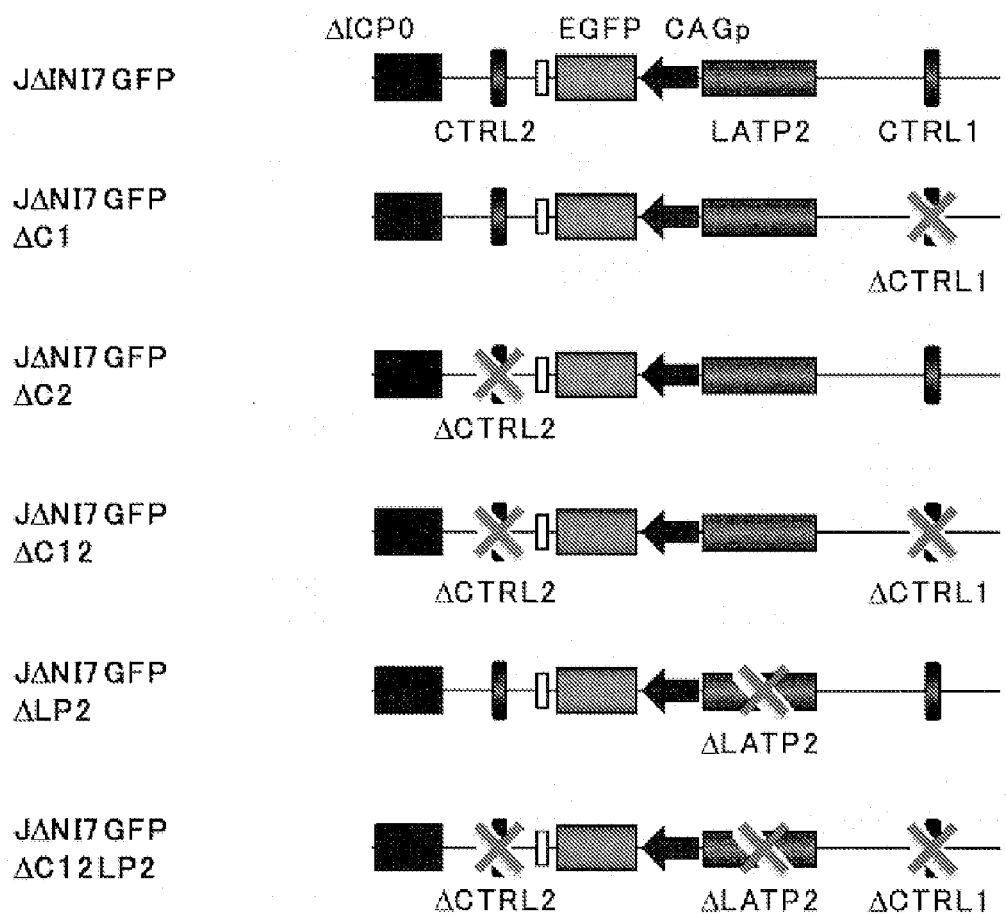
FIGS. 14A-14C. The effect of LAT locus elements on EGFP expression from JΔNI7GFP.
Figure 14:
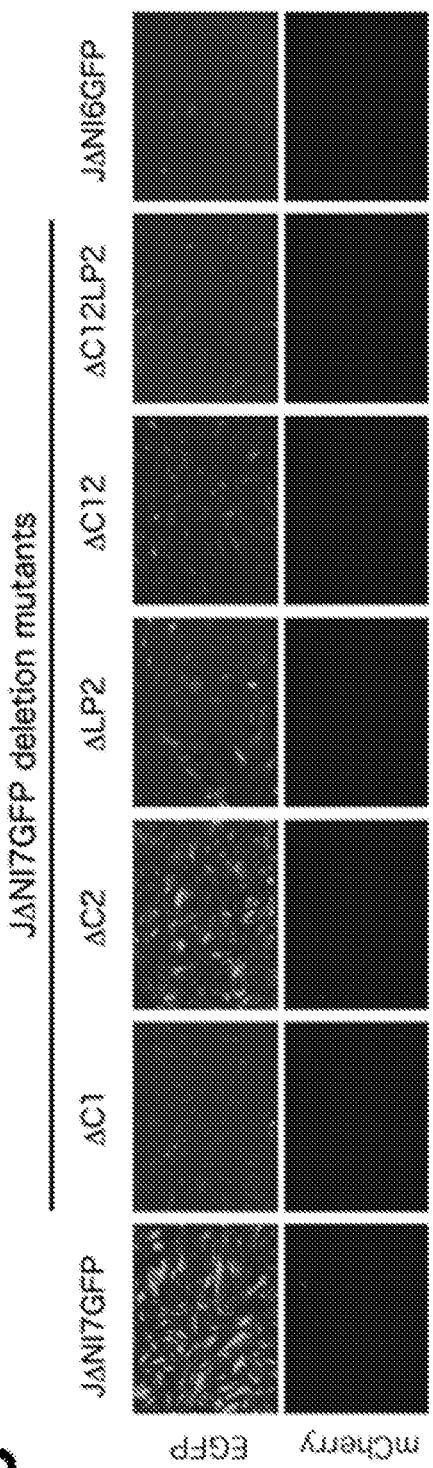
Figure 14:
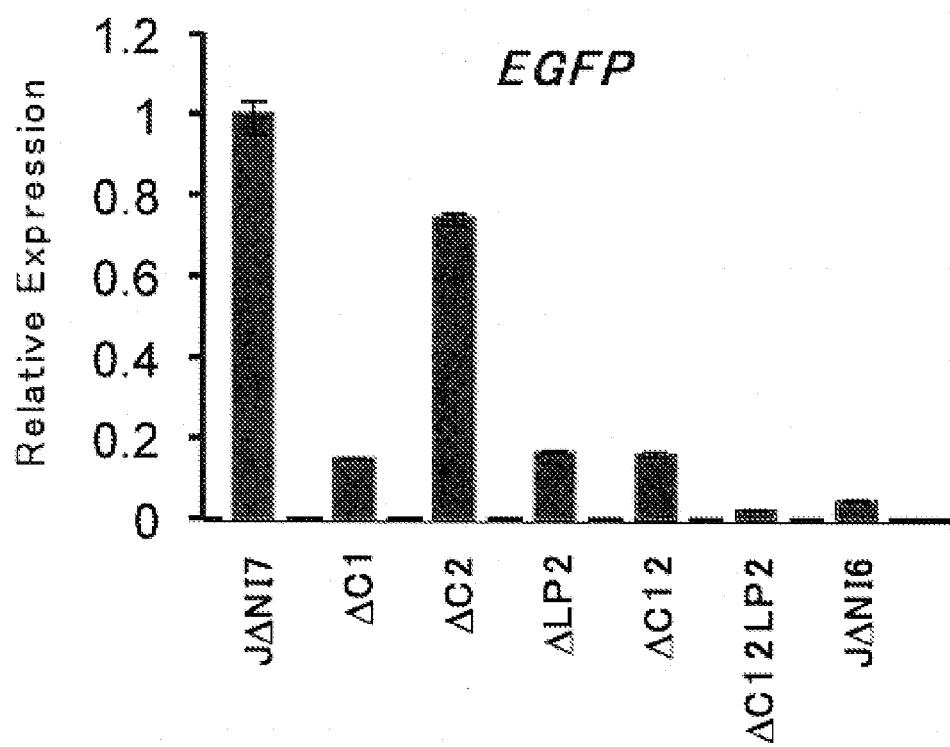

It has been demonstrated that LAT expression during latency is controlled by the latency-associated promoters (LAPs) 1 and 2 (Goins et al., *J. Virol.* 68, 2239-52 (1994); Zwaagstra et al., *Virology* 182, 287-97 (1991)). LAP1 is located upstream of the transcription initiation site of the ~8.7-kb unstable primary LAT transcript that is processed to a stable 2-kb LAT intron, while LAP2 is located downstream of LAP1 in the first exon and extending into the 2-kb intron region. A LAP2-containing region extending somewhat further into the intron has been referred to as LATP2. In addition to acting as a promoter, it has been shown that the LAP2/LATP2 region can act as a position-independent long-term expression/enhancer element for transgene expression in neurons (Berthomme et al., *J. Virol.* 74, 3613-22 (2000); Palmer et al., *J. Virol.* 74, 5604-18 (2000)). However, it has also been reported that the LAT locus is protected from global silencing of the viral genome during latency by regions rich in CTCF binding sites, termed CTRLs, one located upstream of LAP1 (CTRL1) and the other in the 2-kb intron just downstream of LATP2 (CTRL2) (Blooom et al., *Biochim. Biophys. Acta* 1799, 246-56 (2010)). Thus, the potential roles of the LATP2 and CTRL elements in enabling the observed EGFP expression in JΔNI7GFP-infected HDFs was explored. The three elements were deleted separately and in combinations from the JΔNI7GFP genome (FIG. 14A) and reporter gene expression in infected HDFs was examined (FIGS. 14B, 14C). Deletion of either CTRL1 (ΔC1) or LATP2 (ΔLP2) caused a marked decrease in green fluorescence and EGFP mRNA levels whereas the deletion of CTRL2 (ΔC2) had only a minor effect. Deletion of both CTRLs (ΔC12) had the same effect as the deletion of CTRL1 alone while deletion of all three elements (ΔC12LP2) reduced expression further to the level observed in JΔNI6-CAGGFP-infected cells. No mCherry fluorescence was detectable in any of the infected cells (FIG. 14B), suggesting that the different deletions did not cause derepression of other sites in the viral genome. These results indicated that both CTRL1 and the LATP2 region play significant roles in protecting the linked transgene from transcriptional silencing in the context of a viral genome that is functionally devoid of all IE genes.

LAT Locus Protection of Transgene Expression is Position-Independent

Figure 13:
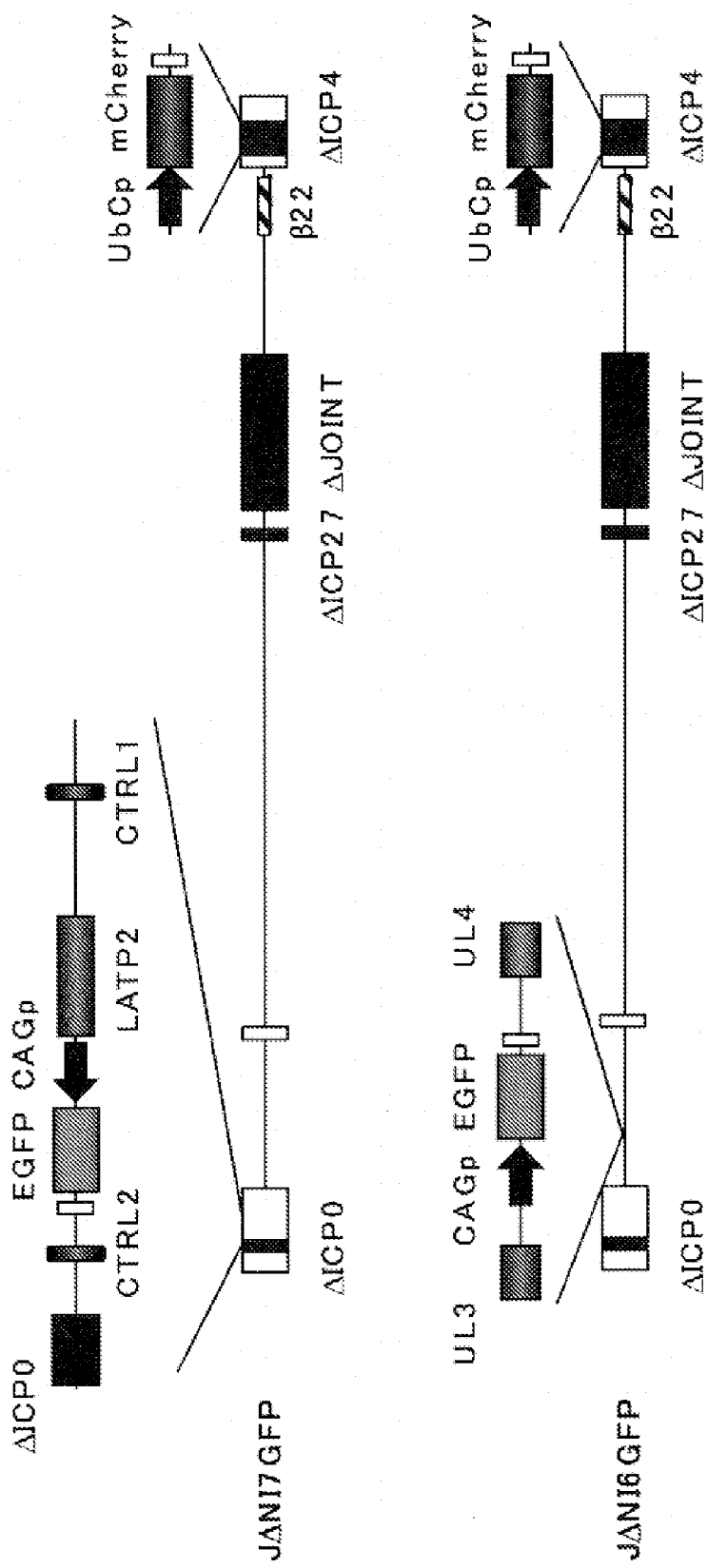
FIGS. 13A-13D. JΔNI6GFP and JΔNI7GFP genome structures and reporter gene expression.
Figure 13:
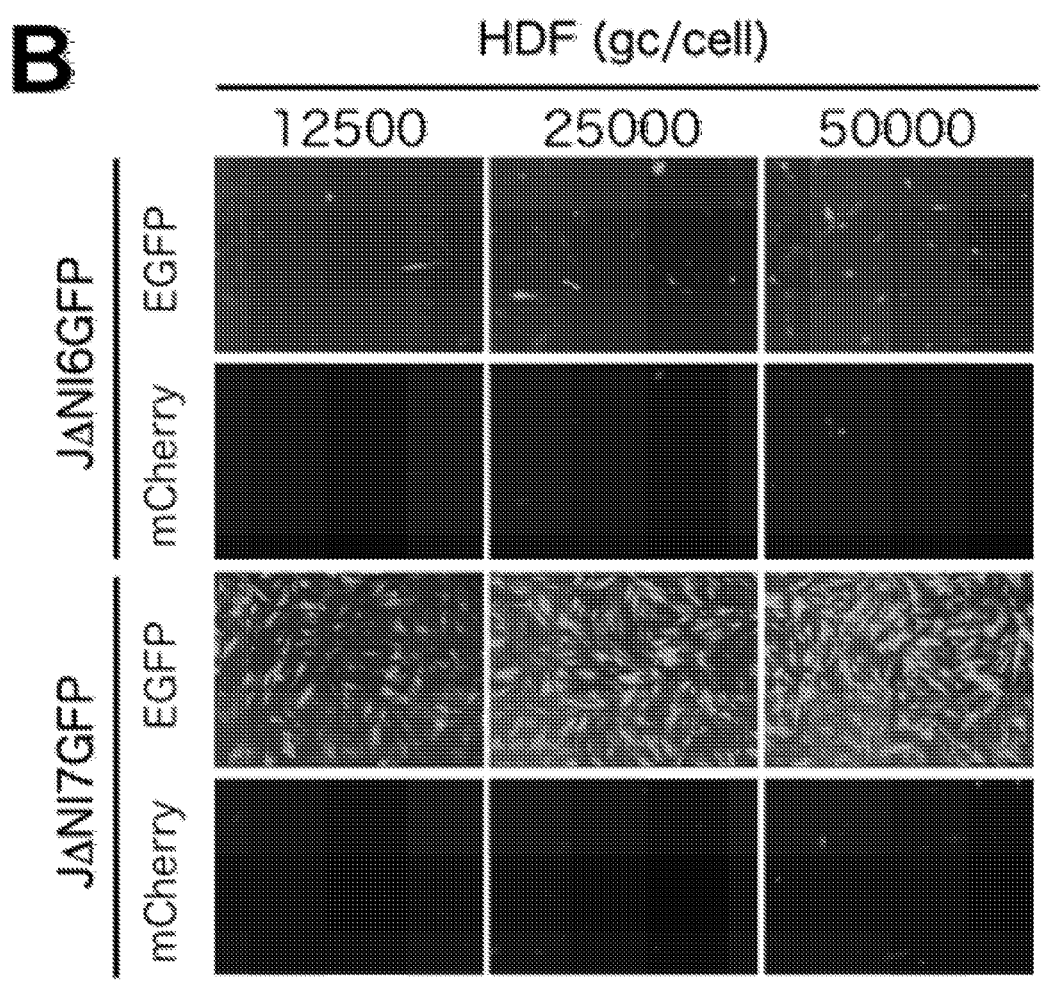
Figure 13:
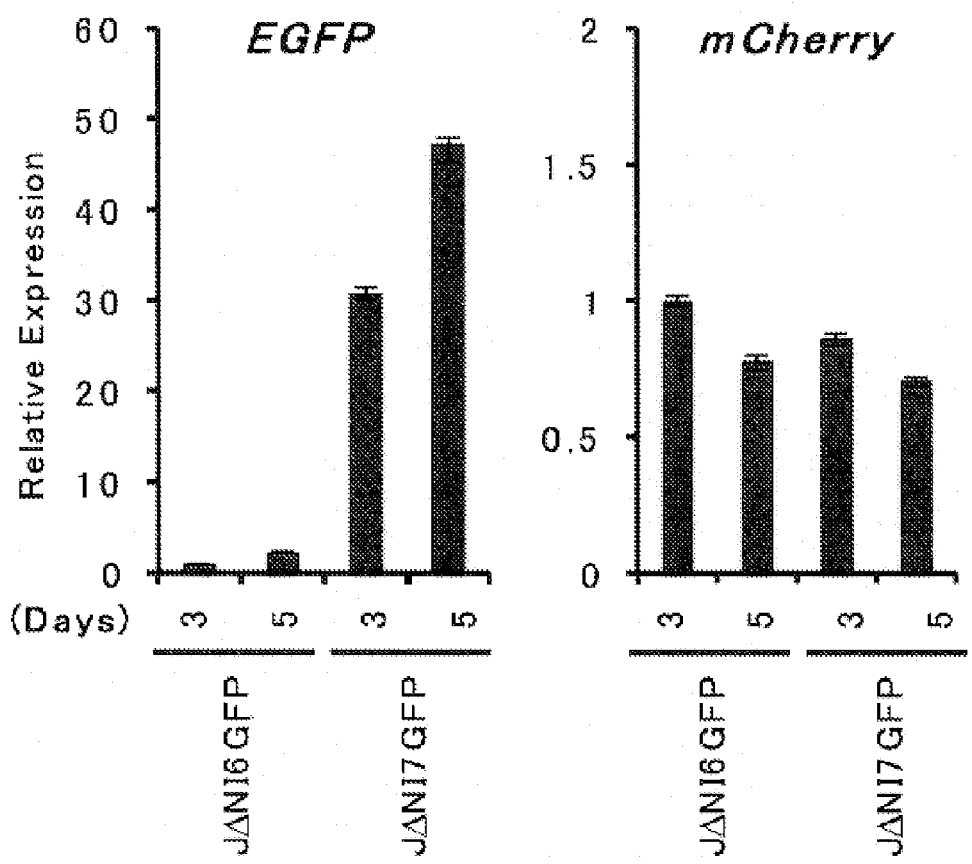
Figure 13:
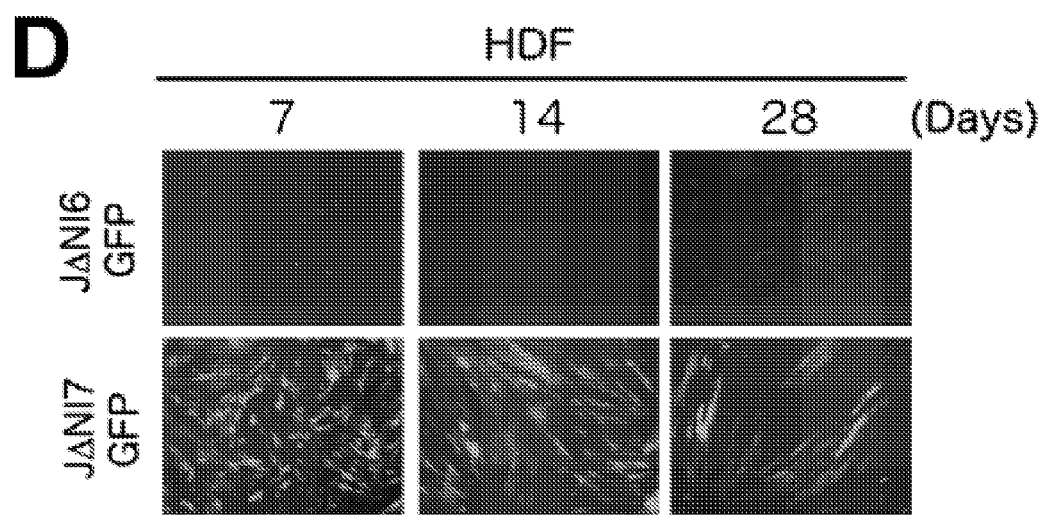
Figure 15:
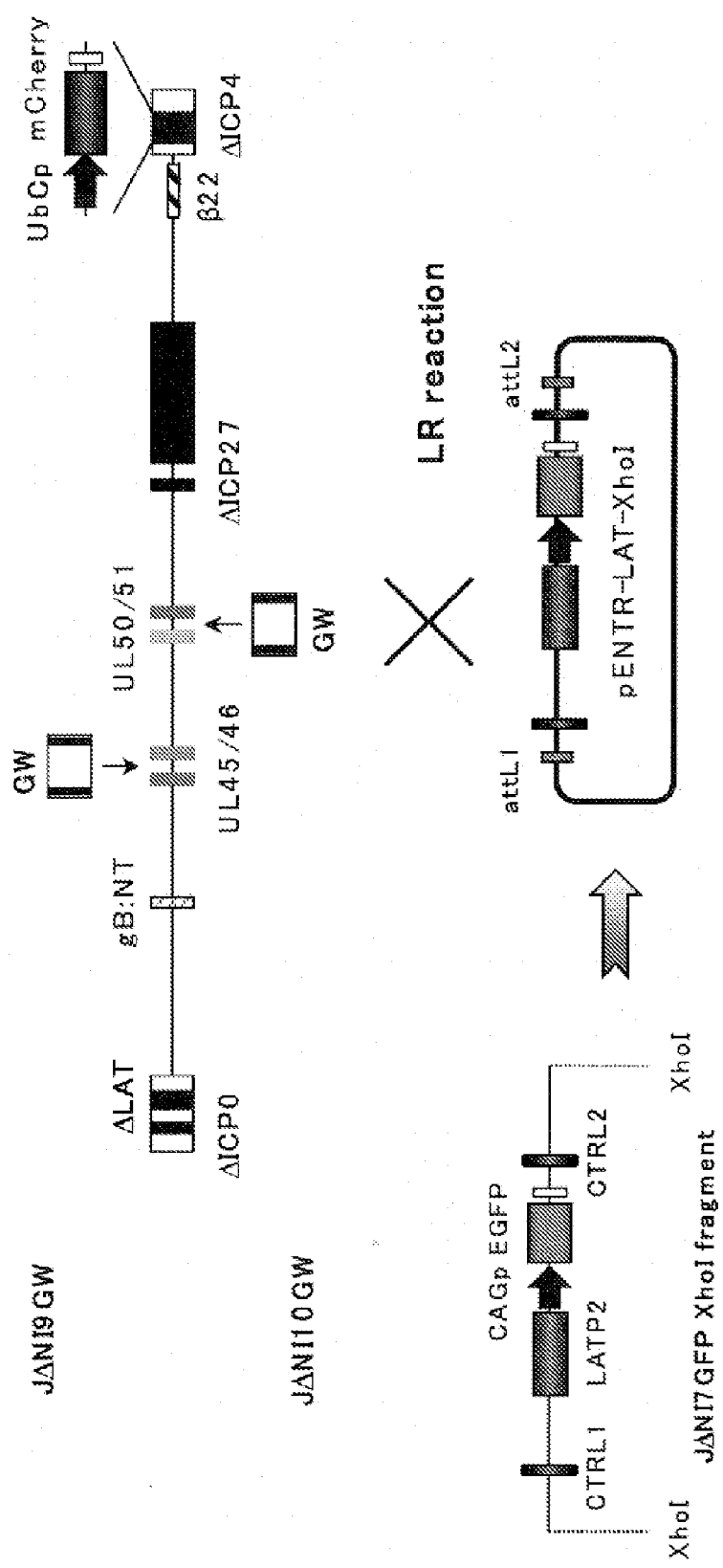
FIGS. 15A-15D. Anti-silencing activity of LAT sequences positioned elsewhere in the viral genome.
Figure 15:
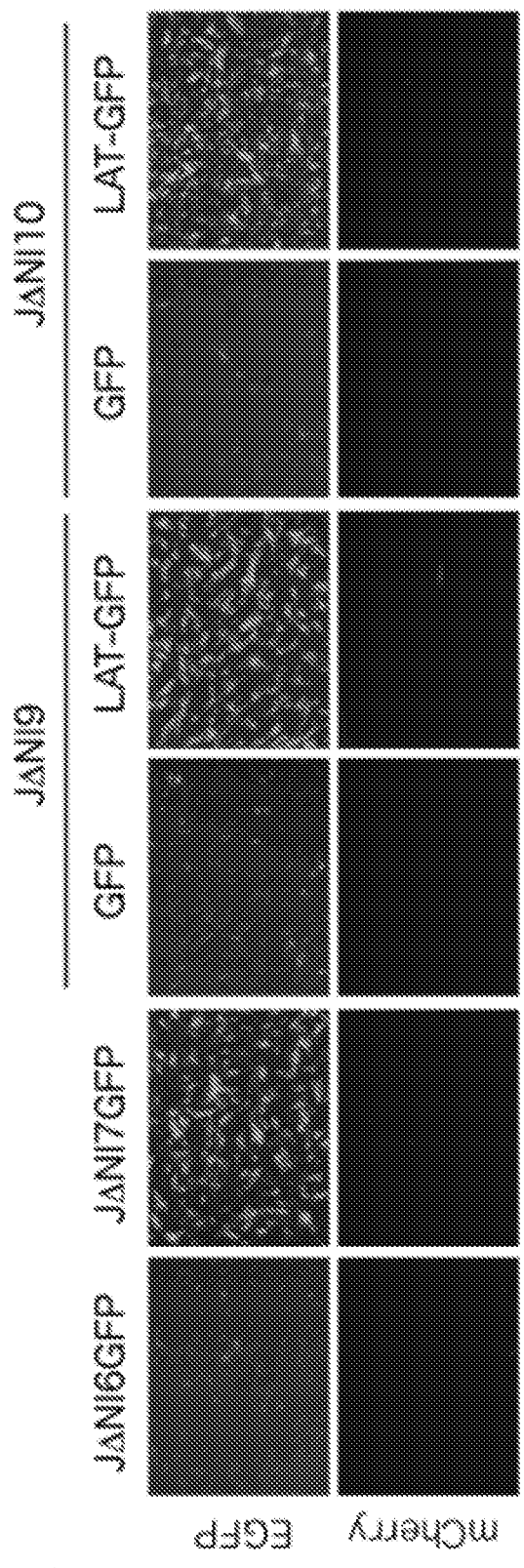
Figure 15:
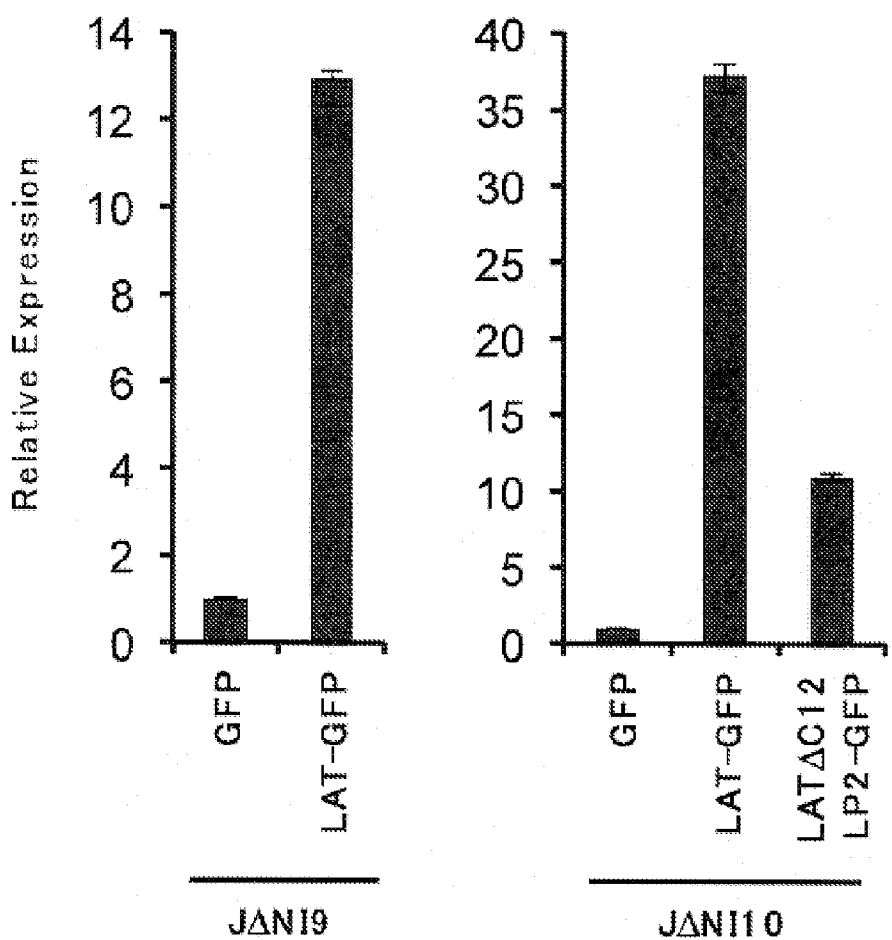
Figure 15:
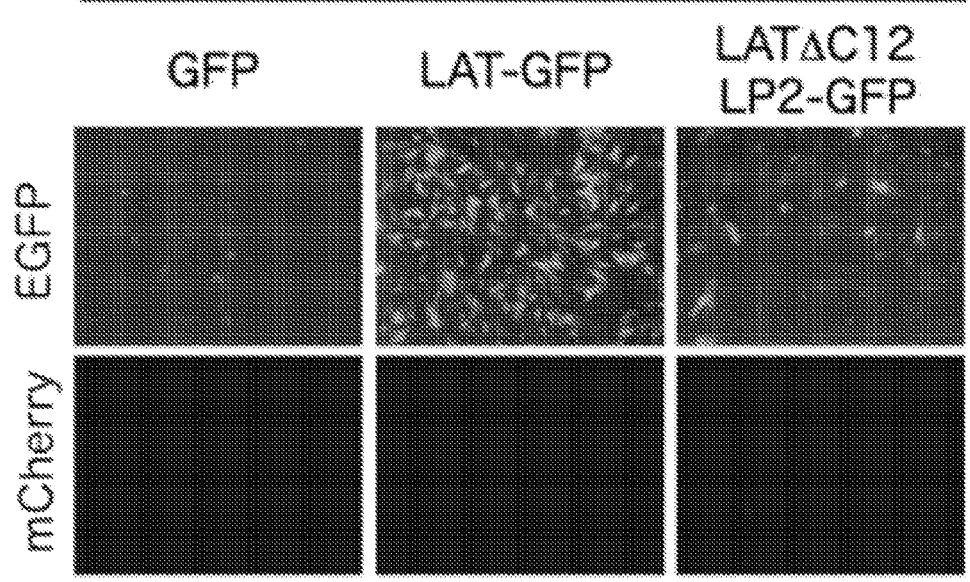

To determine whether sequences associated with the LAT locus are sufficient to protect an embedded transgene expression cassette against silencing in the absence of IE gene products, a restriction fragment corresponding to the LAT:CAGp-GFP region of JΔNI7GFP, including the two CTRLs, LAP1 and LATP2, was inserted at one of two ectopic positions in a JΔNI5 derivative that was deleted for the same LAT region to avoid recombination between the native and new sites. First, a Gateway (GW) recombination cassette was introduced into the intergenic region between UL45 and 46 (JΔNI9GW) or between UL50 and UL51 (JΔNI10GW) of the LAT-deleted JΔNI5 genome and then the LAT:CAGp-GFP fragment or just CAGp-GFP without LAT sequences were introduced by recombination with the GW cassette (FIG. 15A). Following virus production on U2OS-ICP4/27 cells (Table 2), the vectors were tested for reporter gene expression in infected HDFs. At 3 dpi, the vectors that lacked LAT sequences surrounding the reporter cassette (JΔNI9GFP and JΔNI10GFP) showed low levels of EGFP fluorescence (FIG. 15B) and mRNA (FIG. 15C) in infected cells, similar to the JΔNI6-CAGGFP control vector, suggesting that the two intergenic insertion sites were transcriptionally repressed, like the intergenic region between UL3 and UL4 (FIG. 13). However, when the reporter cassette was flanked at both sides by LAT sequences (vectors JΔNI9LAT-GFP and JΔNI10LAT-GFP), EGFP expression increased to the level observed in JΔNI7GFP-infected cells (FIG. 15B), indicating that the anti-silencing activity of the LAT-derived regions is functional in a position-independent manner. To confirm the dependence of this activity on LATP2 and either or both CTRLs, a LATP2- and CTRL-deleted version of the LAT:CAGp-GFP fragment was introduced by GW recombination into JΔNI10GW genome; the deletions were the same as those in the LAT region of the earlier JΔNI7GFPΔC12LP2 vector (FIG. 14A). The deletions reduced EGFP expression in infected HDFs, although not fully down to the level observed with the LAT-free JΔNI10GFP vector (FIG. 15C, 15D); it is unclear why the ΔC12LP2 deletions appear to have a smaller effect here (~3.5-fold) than in JΔNI7GFP (~50-fold, FIG. 14C). However, these results clearly demonstrate that a portion of the LAT locus that includes the 2 CTRLs, LAP1 and LATP2 can protect an embedded transgene expression cassette in a position independent-manner against global silencing of the viral genome in the absence of IE gene expression and indicate that at least CTRL1 and LATP2 play a role in this activity.

LAT Locus Elements Protect Transgene Expression in Other Cell Types

Figure 16:
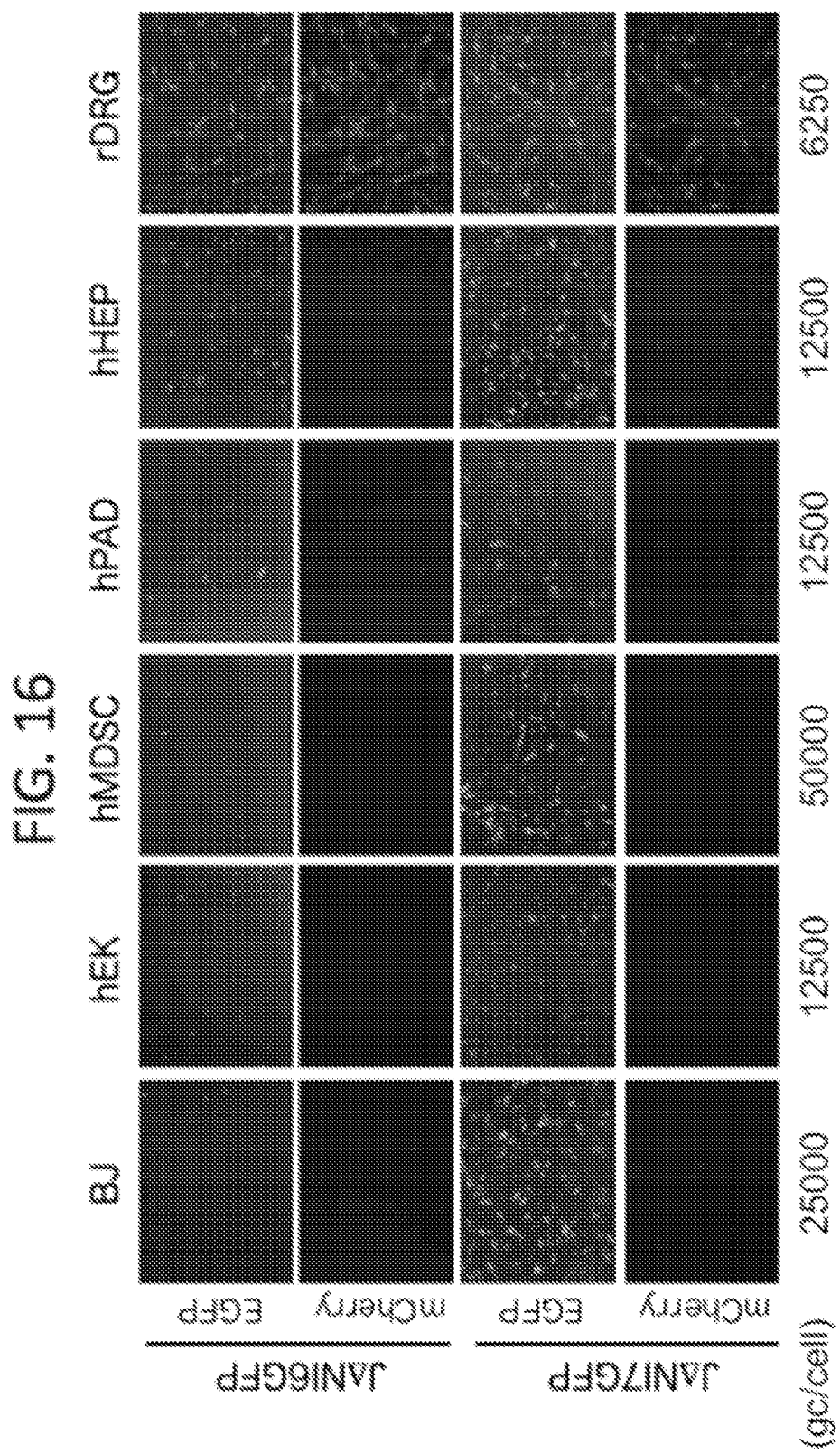
FIGS. 16A-16D. Reporter gene expression from JΔNI vectors in other non-complementing cells.
Figure 16:
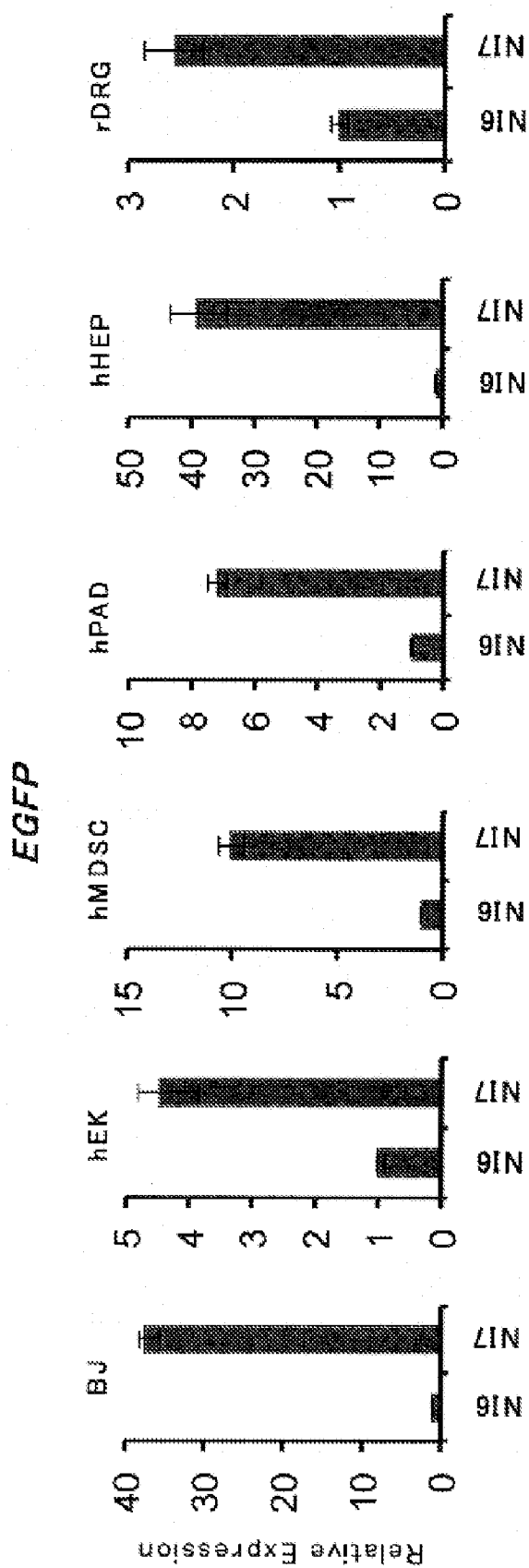
Figure 16:
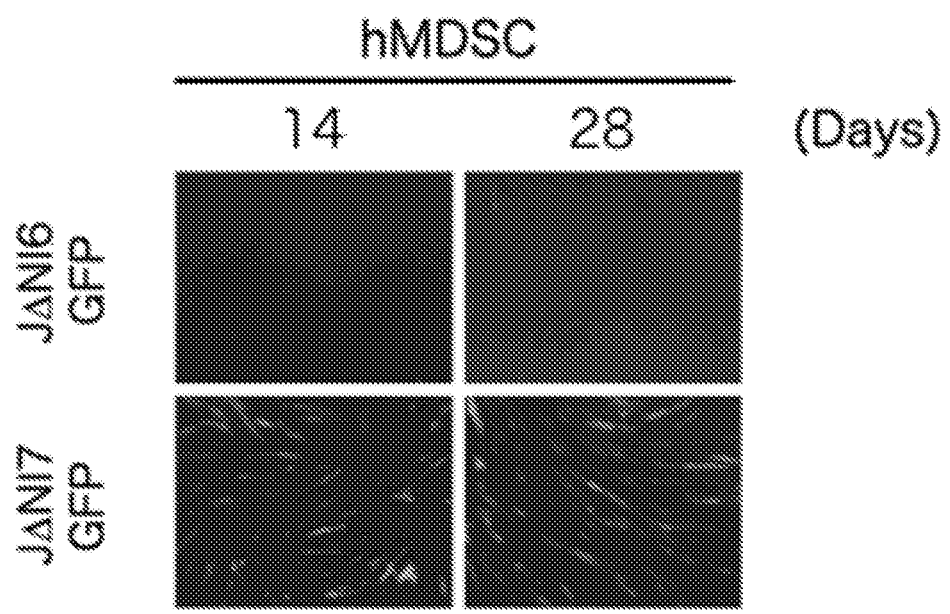
Figure 16:
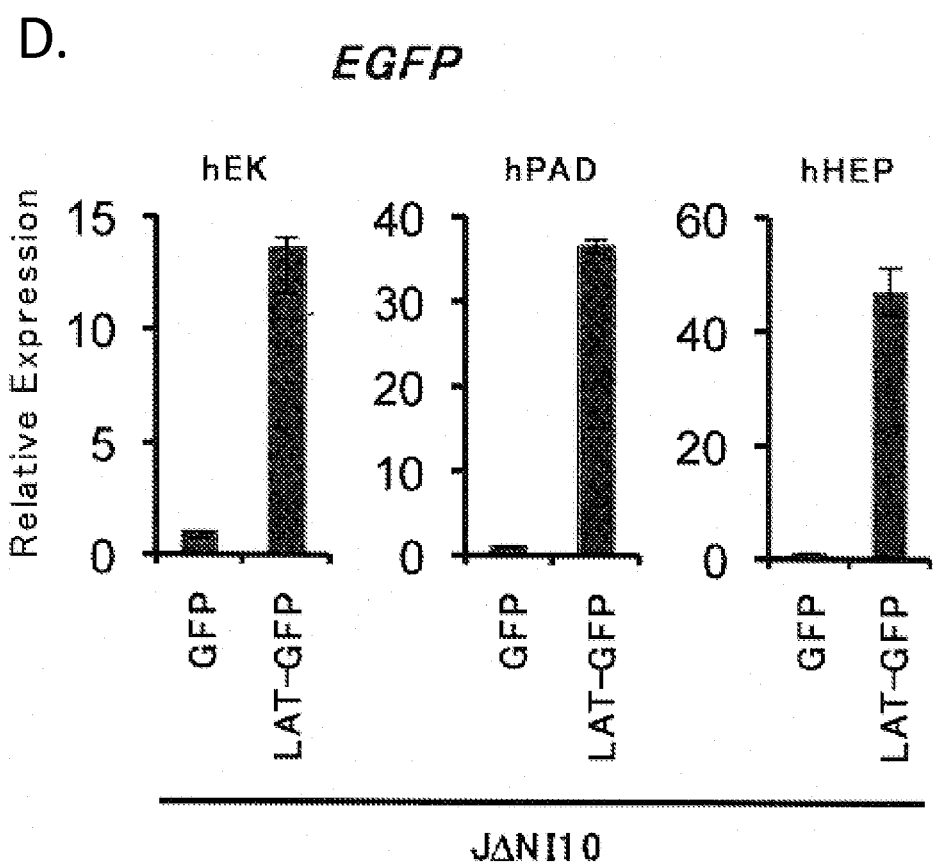

To evaluate the applicability of these findings beyond HDFs, EGFP and mCherry expression from selected vectors was tested in other cell types. By qRT-PCR, higher EGFP mRNA levels were observed in JΔNI7GFP- than in JΔNI6-CAGGFP-infected human cells at 3 dpi (FIG. 16B). The greatest differences were observed in BJ human foreskin fibroblasts (~35-fold), similar to the difference in HDFs (~30-fold, FIG. 13C), and in human hepatocytes (hHEP) (~40-fold). Human neonatal keratinocytes (hEK) showed the smallest difference (~4.5-fold) with intermediate values seen in muscle-derived stem cells (hMDSC) (~10-fold) and preadipocytes (hPAD) (~7-fold). Comparison of the 2 vectors in fetal rat dorsal root ganglion (rDRG) neurons revealed only a ~2.5-fold difference. FIG. 16A shows representative fluorescence images at 3 dpi from an independent experiment performed under the same infection conditions. With the exception of hHEPs that were from a different donor here than in FIG. 16B, the results were largely consistent with the qRT-PCR data. Of interest, while none of the human cells showed significant mCherry fluorescence, abundant mCherry expression was observed in both the JΔNI6-CAGGFP- and JΔNI7GFP-infected rat DRG cultures. It is not yet known whether this observation is unique to neuronal cells and may be a function of the promoter in front of the mCherry gene, the location of the expression cassette in the viral genome, and/or the rat origin of the cells. hMDSCs were maintained for an extended period of time, allowing the monitoring of EGFP expression over time in JΔNI7GFP-infected cells. As shown in FIG. 16C, EGFP was readily detectable for at least 4 weeks after infection in JΔNI7GFP-infected cells but not in JΔNI6GFP-infected cells, similar to the observation with JΔNI7GFP-infected HDFs (FIG. 13D).

Lastly, for some of the cells, whether CAGp-GFP activity in the UL50/51 intergenic region was enhanced by flanking LAT sequences as in HDFs was determined. The results in FIG. 16D show a substantial enhancement in all three cell types that may, for unknown reasons, exceed the difference between JΔNI6-CAGGFP and JΔNI7GFP in the same cells. Overall, these results indicated that the position-independent anti-silencing activity of genetic elements in the LAT locus is not limited to HDFs, but is operative in a variety of non-neuronal human cell types.

Tables for Example 8

TABLE 1

Primer Sequences
PCR primers for qRT-PCR and qPCR

| SEQ ID NO | Target gene | Forward (F)/Reverse (R) | Sequence |
| --- | --- | --- | --- |
| 2 | Human S18 | F | GCGGCGGAAAATAGCCTTTG |
| 3 | | R | GATCACACGTTCCACCTCATC |
| 4 | EGFP | F | ATCATGGCCGACAAGCAGAAGAAC |
| 5 | | R | GTACAGCTCGTCCATGCCGAGAGT |
| 6 | mCherry | F | CCTGTCCCCTCAGTTCATGT |
| 7 | | R | GCTTCAAGTAGTCGGGGATG |
| 8 | ICP0 | F | ACCACCATGACGACGACTC |
| 9 | | R | AGCCCCGTCTCGAACAGT |
| 10 | ICP22 | F | CGTGTGCAAGCTTCCTTGT |
| 11 | | R | TCTCGAGATTACTAAGATCACACTCC |
| 12 | ICP27 | F | AGTCGTGTCTGCGAGTTGAC |
| 13 | | R | AAAACAGGGAGTTGCAATAAAAA |
| 14 | ICP4 | F | ATGGGGTGGCTCCAGAAC |
| 15 | | R | CTGCCGGTGATGAAGGAG |
| 16 | ICP34.5 | F | GTAACCTCCACGCCCAACT |
| 17 | | R | AGCAGCAGCGAACAAGAAG |
| 18 | UL11 | F | ATGGGCCTCTCGTTCTCC |
| 19 | | R | CGGTGATGAGGACGTTGTT |
| 20 | UL23 (TK) | F | TCATCTTCGACCGCCATC |
| 21 | | R | TGCTGCCCATAAGGTATCG |
| 22 | UL27 (gB) | F | GTCAGCACCTTCATCGACCT |
| 23 | | R | CAGGGGGACAAACTCGTG |
| 24 | UL29 (ICP8) | F | AGCTGCAGATCGAGGACTG |
| 25 | | R | CCATCATCTCCTCGCTTAGG |
| 26 | UL30 | F | GTCTGCTCTACGACCTGTCCA |
| 27 | | R | AACCGAGCGAAAACAGGAG |
| 28 | UL41 (vhs) | F | TCCATCCCAATAACACCTACG |
| 29 | | R | GGGGTCCAGTGACATTCG |
| 30 | UL44 (gC) | F | GAGGGTCAGCCGTTCAAG |
| 31 | | R | AACTCCACGGGGTTACGC |
| 32 | UL48 (VP16) | F | GCGCTCTCTCGTTTCTTCC |
| 33 | | R | GGCCAACACGGTTCGATA |

TABLE 1-continued

Primer Sequences
PCR primers for qRT-PCR and qPCR

| SEQ ID NO | | Forward (F)/Reverse (R) | Sequence |
|---|---|---|---|
| 34 | UL39 (ICP6) | F | CAATCTGGGAAGCGTGAATC |
| 35 | | R | CGCCCAAAGTCAAACGTC |
| 36 | Rat S18 | F | CCACAGGAGGCCTACACG |
| 37 | | R | CTGAAACTTCTCGGGGATCA |
| 38 | HSV gD | F | CCCCGCTGGAACTACTATGACA |
| 39 | | R | GCATCAGGAACCCCAGGTT |
| 40 | | Probe | FAM-TTCAGCGCCGTCAGCGAGGA-TAMRA |
| | Red mediated recombination Target gene/locus | | |
| 41 | ΔICP0 | F1 | CCCGATATCCAATTGCGGGCGCTGGGTGGTCTCTGGCCGCGCCCACTACACCAGCCAATCCGTGTAGGATGACGACGATAAGTAGGGATA |
| 42 | | F2 | GATCTCGAGCTCAAGCTTCGAATTCTGCAGTCGACGGTACCGCGGGCCCCGATATCCAATTGCGGGC |
| 43 | | R | ACACGGATTGGCTGGTGTAGTGGGCGCGGCCAGAGACCACCCAGCGCCCGCAACCAATTAACCAATTCTGATTAG |
| 44 | ΔICP27 | F | TATGGATCCCGGACCTGGTTAACCACCCGCCGGTCCTACGCGAACTGGAGGATAAGCGCAGGATGACGACGATAAGTAGGGATA |
| 45 | | R | CAGGAATTCGCGCTTATCCTCCAGTTCGCGTAGGACCGGCGGGTGGTTAACCAGGTCCGCAACCAATTAACCAATTCTGATTAG |
| 46 | Joint deletion | F1 | GGGCCCTGGAAATGGCGGACACCTTCCTGGACACCATGCGGGTTGGGCCCAGGATGACGACGATAAGTAGGGATAACAGGG |
| 47 | | R | GGGCCCAACCCGCATGGTGTCCAGGAAGGTGTCCGCCATTTCCAGGGCCCCAACCAATTAACCAATTCTGATTAG |
| 48 | | F2 | TTTATAACCCCGGGGGTCATTCCCAACGATCACATGCAATCTAACTGGCTGGGCCCTGGAAATGGCGGACACC |
| 49 | UbC-mCherry insertion | F1 | TATGGATCCCCGCGGATGGTGAGCAAGGGCGAGGAGGATAACATGGCCATCATAGGATGACGACGATAAGTAGGG |
| 50 | | R1 | AATCTGCAGGGATCCCTACAACCAATTAACCAATTCTGATTAG |
| 51 | | F2 (For ΔICP4) | CTTGGGGCGGTCCCGCCCGCCGGCCAATGGGGGGCGGCAAGGCGGGCGGTGGCGGCCGCTCTAGAAGATCTGGC |
| 52 | | R2 (For ΔICP4) | CCGCGGGGGCCCGGGCTGCCACAGGTGAAACCAACAGAGCACGGCGCACGCTGGGTACCGGGCCCCCCCTCGAG |
| 53 | | F3 (For UL3 and 4) | CCTCACTGCCCGTCGCGCGTGTTTGATGTTAATAAATAACACATAAATTTTGGCGGCCGCTCTAGAAGATCTGGC |
| 54 | | R3 (For UL3 and 4) | CCGACACTGAAATGCCCCCCCCCCCTTGCGGGCGGTCCATTAAAGACAACGCTGGGTACCGGGCCCCCCCTCGAG |
| 55 | CAG-EGFP insertion | F1 | TATTACGTATTAGTCATCGCTATTACCATGGTCGAGGTGAGCCCCACGTTCTGCTTAGGATGACGACGATAAGTAGGGATA |
| 56 | | R1 | AATCTGCAGTACGTACTACAACCAATTAACCAATTCTGATTAG |
| 57 | | F2 | GCAATTGGCTCTGCCCCGCCGTCCCCGTGTTCGTCC |
| 58 | | R2 | TTTTTGCAAAAGCCTAGGCCTCCAATAACTAGTCAATAATCAATGTCGACTTATTTATTAACATCAAACACGCGC |
| 59 | | F3 | GCACGCGTAGAGGTGCTGCGGGAGATTCAACTGAGC |

TABLE 1-continued

Primer Sequences
PCR primers for qRT-PCR and qPCR

| SEQ ID NO | | Forward (F)/Reverse (R) | Sequence |
|---|---|---|---|
| 60 | | R3 | TATTGACTAGTTATTGGAGGCCTAGGCTTTTGCAAAAAAGCTTATAATGGGTCTTTAATGGACCGCCCGCAAGGG |
| 61 | gB:N/T insertion | F | TATTACGTACAACCACATACAGCGCCATGTCAACGATATGTTGGGCCGCGTTGAGGATGACGACGATAAGTAGGG |
| 62 | | R | AATCTGCAGTACGTACTACAACCAATTAACCAATTCTGATTAG |
| 63 | ΔCTRL1 | F1 | TATACCCGTGACACCCGACGCTGGGGGGCGTGGCTGCCGGGAGGGGCCGCGTATGAGGATGACGACGATAAGTAGGGATA |
| 64 | | F2 | CCACACAAGCCCCGTATCCCCGTTCCCGCGCTTTTCGTTGGTITATATACCCGTGACACCCGACGCTGGG |
| 65 | | R | CATACGCGGCCCCTCCCGGCAGCCACGCCCCCAGCGTCGGGTGTCACGGCAACCAATTAACCAATTCTGATTAG |
| 66 | ΔCTRL2 | F1 | AATCCAACACAGACAGGGAAAAGATACAAAAGTAAACCTTTATTTCCCAACAAGGATGACGACGATAAGTAGGGATAACA |
| 67 | | F2 | GTCAGGCAGCCCGGGCCGCGGCTCTGTGGTTAACACCAGAGCCTGCCCAATCCAACACAGACAGGGAAAA |
| 68 | | R | TGTTGGGAAATAAAGGTTTACTTTTGTATCTTTTCCCTGTCTGTGTTGGACAACCAATTAACCAATTCTGATTAG |
| 69 | ΔLATP2 | F1 | CAGATAGTAATCAATTACGGGGTCATTAGTTCATAGCCCATATATGGAGTTCCAGGATGACGACGATAAGTAGGGATAAC |
| 70 | | F2 | AGACTTTCCGGGCGCGTCCGGGTGCCGCGGCTCTCCGGGCCCCCTGCAGATAGTAATCAATTACGGGGT |
| 71 | | R | GGAACTCCATATATGGGCTATGAACTAATGACCCCGTAATTGATTACTATCAACCAATTAACCAATTCTGATTAG |
| 72 | GW | F1 (For LAT) | TGACAATTGACTAGTTATACAAGTTTGTACAAAAAAGCTGAAC |
| 73 | | R1 (For LAT) | CCATTATAACAATTGAGATCTCCACITTGTACAAGAAAGCTGAACG |
| 74 | | F2 (For UL45 and 46) | CGGACCCAAAATAATAAACACACAATCACGTGCGATAAAAAGAACACGCGACAAGTTTGTACAAAAAAGCTGAAC |
| 75 | | R2 (For UL45 and 46) | CCTGTTTGTCGACGAGATTTAATAAAAATAACCAAAAACACCACAGGGGACCACTTTGTACAAGAAAGCTGAACG |
| 76 | | F3 (For UL50 and 51) | AAACGTTTGTATCTCATCTTTCCTGTGTGTAGTTGTTTCTGTTGGATGCCATATCACAAGTTTGTACAAAAAAGC |
| 77 | | R3 (For UL50 and 51) | TGCGTGTTTTCATCCAACCCGTGTGTTCTGTGTTTGTGGGATGGAGGGGCCGAGAAACGTAAAATGATATAAATA |
| 78 | ΔLAT | F1 | CCGGGGACACCGCCAGCAAACGCGAGCAACGGGCCACGGGGATGAAGCAGAGGATGACGACGATAAGTAGGGATA |
| 79 | | F2 | CCACACAAGCCCCGTATCCCCGTTCCCGCGCTTTTCGTTGGTTTATATACCCGGGGACACCGCCAGCAAACGCGA |
| 80 | | R | CTGCTTCATCCCCGTGGCCCGTTGCTCGCGTTTGCTGGCGGTGTCCCCGGCAACCAATTAACCAATTCTGATTAG |
| 81 | Insertion of TK promoter | F1 (for ICP0 pro) | CCCGGCCAACCAGCGTCCGCCGAGTCTTCGG |
| 82 | | R1 (for ICP0 pro) | GCCGGTTCCAGTGTAAGGGTCGGGGGTCCC |

TABLE 1-continued

Primer Sequences
PCR primers for qRT-PCR and qPCR

| SEQ ID NO | Forward (F)/Reverse (R) | Sequence |
|---|---|---|
| 83 | F2 (for ICP27 pro) | CCTGACAGAGCTGTATTGTA |
| 84 | R2 (for ICP27 pro) | AGATCGCTGTCGGAGAGGTCC |
| 85 | F3 (for ICP0 pro) | TATAGATCTCGAGCTCAAGCTTCGAATTCTGCAGTCGACGGTACCGCGGGCCCAGGATGACGACGATAAGTAGGG |
| 86 | R3 (for ICP0 pro) | AATCTGCAGAGATCTCTACAACCAATTAACCAATTCTGATTAG |
| 87 | F4 (for ICP27 pro) | TATGTTAACAACAACAATTGCATTCATTTTATGTTTCAGGTTCAGGGGAGGTAGGATGACGACGATAAGTAGGG |
| 88 | R4 (for ICP27 pro) | AATCTGCAGGTTAACCTACAACCAATTAACCAATTCTGATTAG |

TABLE 2

Viruses used in this Example

| Virus | gc/ml | pfu/ml | gc/pfu | ICP0 | ICP4* | ICP22** | ICP27 | ICP47 | gB |
|---|---|---|---|---|---|---|---|---|---|
| KOS | 5.33E+11 | 1.30E+10 | 4.10E+01 | + | + | + | + | + | + |
| KNTc | 8.15E+11 | 2.96E+09 | 2.75E+02 | + | + | + | + | + | N/T*** |
| QOZHG | 1.55E+11 | 2.33E+08 | 6.64E+02 | + | − | β | CMV-GFP | β | + |
| JΔNI2 | 3.28E+11 | 4.00E+08 | 8.20E+02 | β | − | β | β | − | N/T |
| JΔNI3 | 3.46E+11 | 3.36E+08 | 1.03E+03 | − | − | β | β | − | N/T |
| JΔNI5 | 1.17E+12 | 5.00E+08 | 2.35E+03 | − | − | β | − | − | N/T |
| JΔNI6GFP | 7.30E+11 | 2.66E+08 | 2.74E+03 | − | − | β | − | − | N/T |
| JΔNI7GFP | 3.99E+11 | 1.86E+08 | 2.14E+03 | − | − | β | − | − | N/T |
| JΔNI7GFPΔC1 | 1.66E+11 | 5.00E+07 | 3.31E+03 | − | − | β | − | − | N/T |
| JΔNI7GFPΔC2 | 8.42E+11 | 3.50E+08 | 2.41E+03 | − | − | β | − | − | N/T |
| JΔNI7GFPΔLP2 | 4.75E+11 | 1.70E+08 | 2.80E+03 | − | − | β | − | − | N/T |
| JΔNI7GFPΔC12 | 5.97E+11 | 1.86E+08 | 3.21E+03 | − | − | β | − | − | N/T |
| JΔNI7GFPΔC12LP2 | 8.03E+11 | 3.00E+08 | 2.68E+03 | − | − | β | − | − | N/T |
| JΔNI9GW | — | — | — | − | − | β | − | − | N/T |
| JΔNI9GFP | 6.70E+11 | 2.00E+08 | 3.35E+03 | − | − | β | − | − | N/T |
| JΔNI9LAT-GFP | 5.58E+11 | 2.66E+08 | 2.10E+03 | − | − | β | − | − | N/T |
| JΔNI10GW | — | — | — | − | − | β | − | − | N/T |
| JΔNI10GFP | 1.05E+12 | 1.66E+08 | 6.33E+03 | − | − | β | − | − | N/T |
| JΔNI10LAT-GFP | 2.30E+11 | 9.33E+07 | 2.46E+03 | − | − | β | − | − | N/T |
| JΔNI10LAT-GFPΔC12LP2 | 2.69E+11 | 1.23E+08 | 2.19E+03 | − | − | β | − | − | N/T |

| Virus | LAT | UL$_{3-4}$ | UL$_{50-51}$ | UL$_{45-46}$ |
|---|---|---|---|---|
| KOS | + | − | − | − |
| KNTc | + | UbC-mCherry | − | − |
| QOZHG | + | − | − | − |
| JΔNI2 | + | − | − | − |
| JΔNI3 | + | − | − | − |
| JΔNI5 | + | − | − | − |
| JΔNI6GFP | + | CAG-GFP | − | − |
| JΔNI7GFP | CAG-GFP | − | − | − |
| JΔNI7GFPΔC1 | CAG-GFP, ΔCTRL1 | − | − | − |
| JΔNI7GFPΔC2 | CAG-GFP, ΔCTRL2 | − | − | − |
| JΔNI7GFPΔLP2 | CAG-GFP, ΔLATP2 | − | − | − |
| JΔNI7GFPΔC12 | CAG-GFP, ΔCTRL1/2 | − | − | − |
| JΔNI7GFPΔC12LP2 | CAG-GFP, ΔCTRL1/2/LATP2 | − | − | − |
| JΔNI9GW | − | − | − | GW**** |
| JΔNI9GFP | − | − | − | CAG-GFP |
| JΔNI9LAT-GFP | − | − | − | LAT-CAG-GFP |
| JΔNI10GW | − | − | GW**** | − |

TABLE 2-continued

Viruses used in this Example

| | | | | |
|---|---|---|---|---|
| JΔNI10GFP | – | – | CAG-GFP | – |
| JΔNI10LAT-GFP | – | – | LAT-CAG-GFP | – |
| JΔNI10LAT-GFPΔC12LP2 | – | – | LAT-ΔCTRL1/2/LATP2-CAG-GFP | – |

*All BAC-mediated ΔICP4 viruses have the same UbC promoter-driving mCherry expression cassette in the deleted ICP4 locus
**For all BAC-mediated ICP22 viruses, the regulatory sequences of ICP22 promoter (TAATGARAT) were deleted to convert the kinetics of ICP22 gene expression from IE to early gene
***gB: D285N/A549T, referred to herein as gB: N/T
****GW: Gateway recombination site

TABLE 3

JΔNI5 plaquing efficiency on
U2OS-ICP4/27 cells at different passage numbers

| Passage number | Plaque number (mean ± S.D.) |
|---|---|
| p5 | 17.33 ± 6.35 |
| p10 | 15 ± 2.64 |
| p20 | 16 ± 4 |

U2OS-ICP4/27 cells were infected with JΔNI5 virus at 0.1 gc/cell and the cells were overlayed with methylcellulose at 2 hpi.
Plaques were counted at 4 dpi.
Means +/− SD of 3 determinations.

Example 9

This example demonstrates the construction and properties of JΔNI8.

Figure 17:
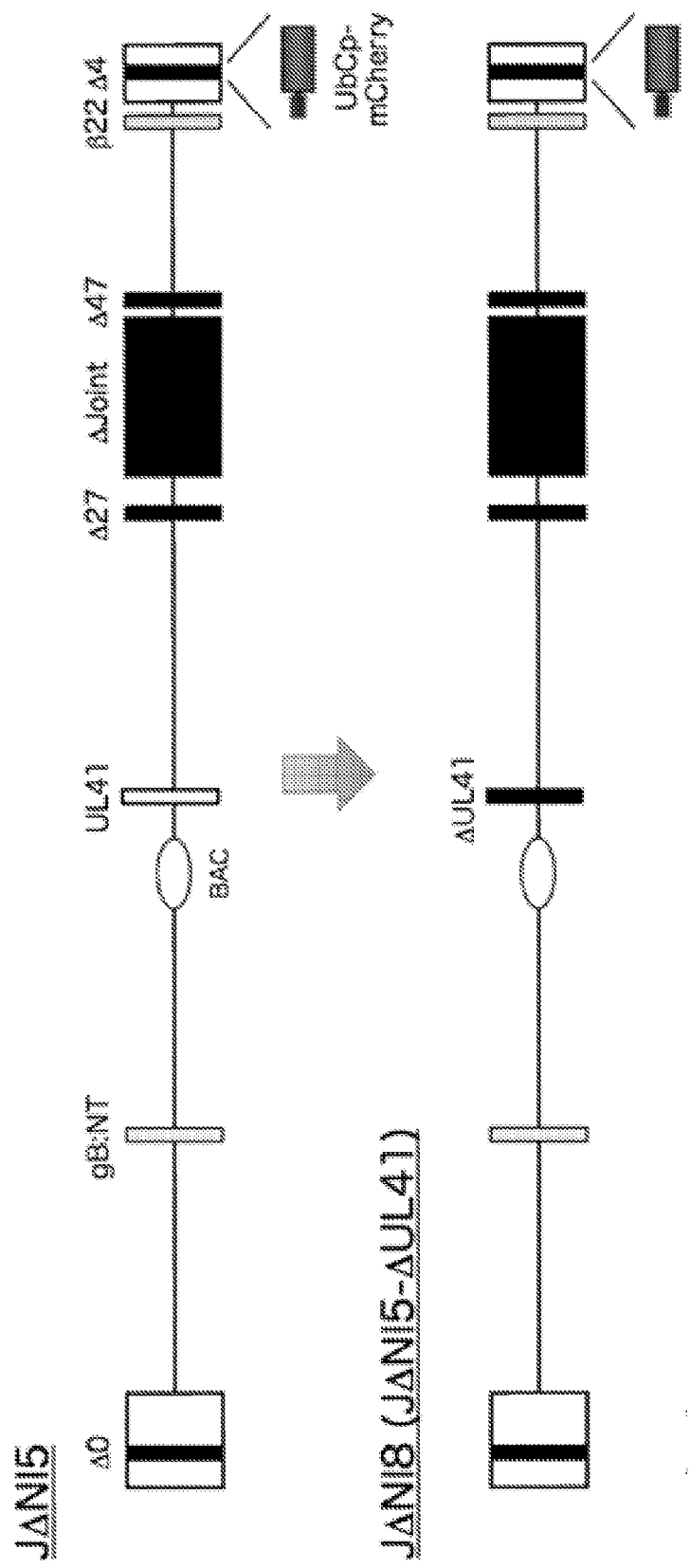
FIG. 17 graphically depicts the construction of JΔNI8 from JΔNI5.
Figure 20:
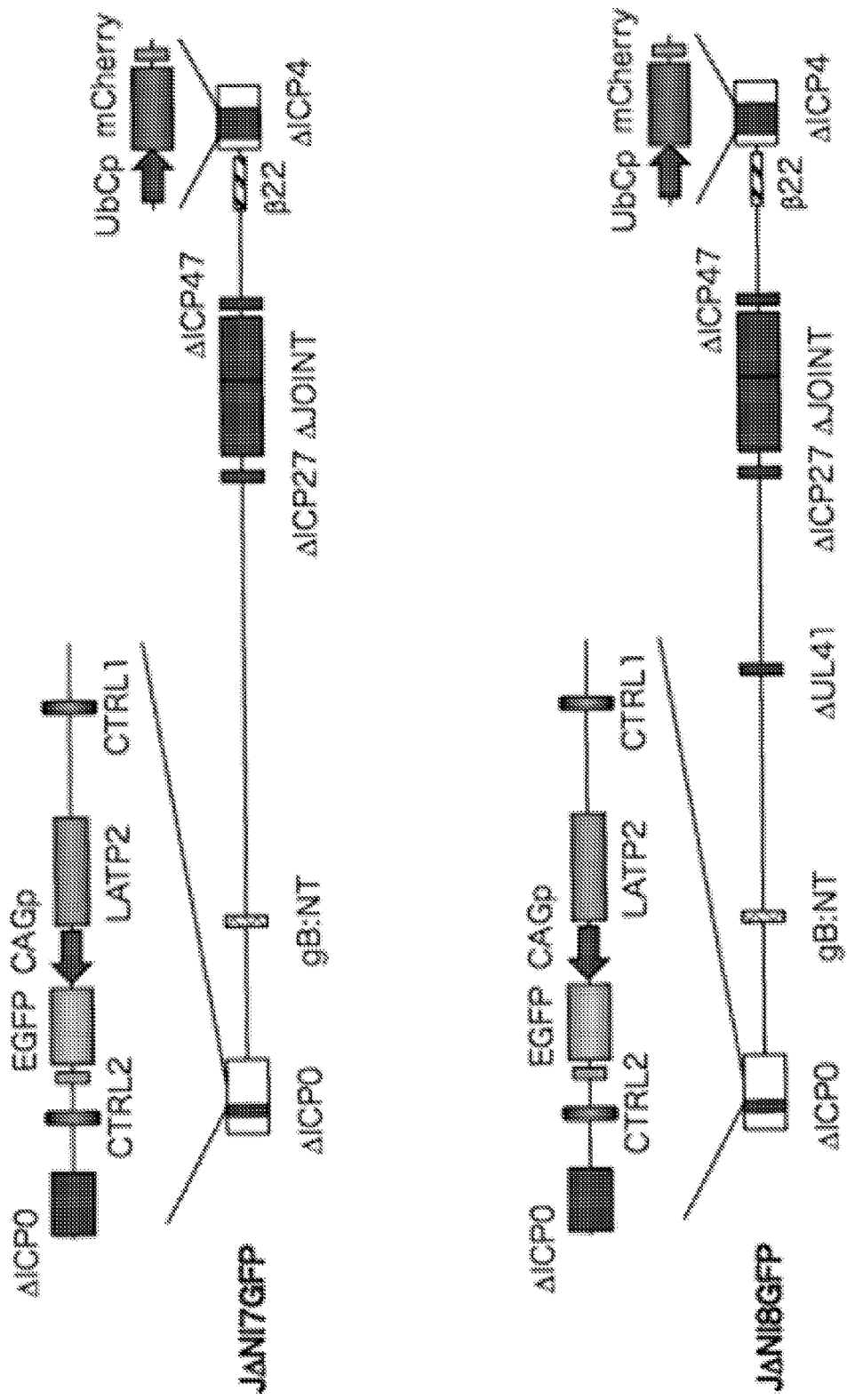
FIG. 20 graphically depicts the genomic structure of JDNI7GFP (also referred to as JΔNI7GFP) and JDNI8GFP (also referred to as JΔNI8GFP).

JΔNI8 was constructed by deletion of UL41 from the JΔNI5 vector discussed above. This is presented graphically in FIG. 17. JΔNI7GFP essentially is JΔNI5 with an insertion of CAGp-EGFP-polyA in the LAT locus between LATP2 and CTRL2. JΔNI8GFP is identical to JΔNI7GFP except for the deletion of UL41. See also FIG. 20.

Figure 19:
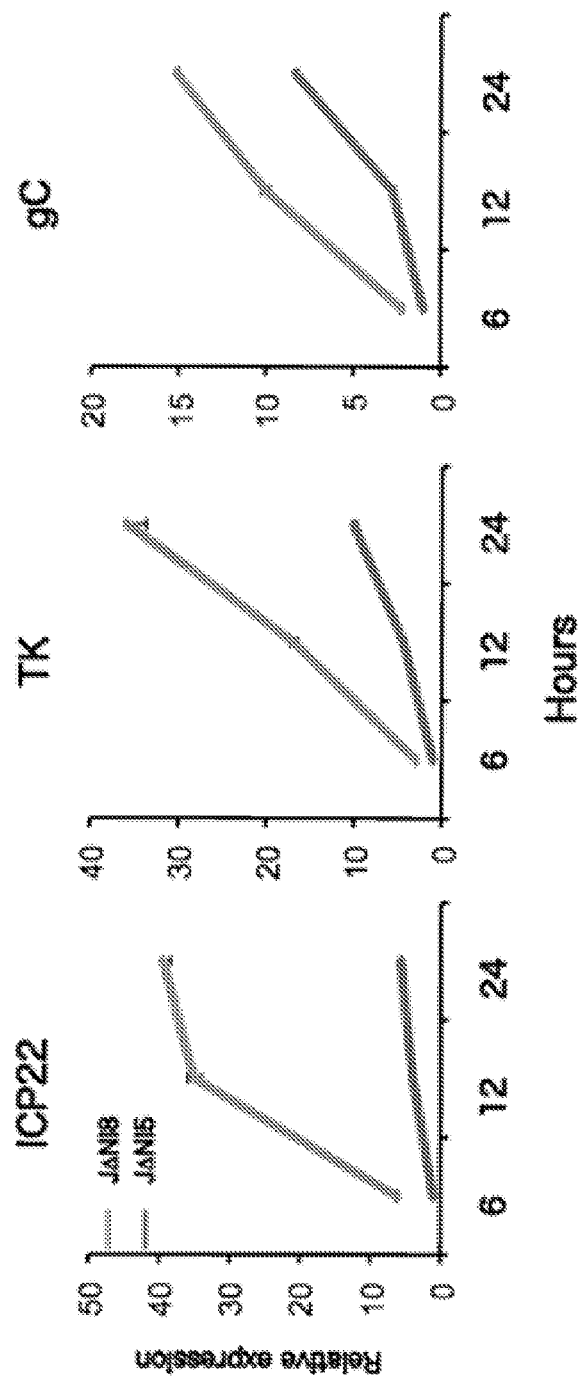
FIG. 19 depicts data demonstrating that viral genes are expressed earlier from JΔNI8 than from JΔNI5 in complementing cells. In each panel, the lower line represents data for JΔNI5, whereas the upper line represents data for JΔNI8. Data were collected by qRT-PCR and is expressed as the fold difference relative to the JΔNI5 data point at 6 hours post-infection (hpi).

The growth of JΔNI8 was assessed relative to JΔNI5 in complementing cells, which, as described above, are U2OS cells engineered to express ICP4 and ICP27. The complementing cells were infected with the respective vector at 1 viral genome copy (gc) per cell. As depicted in FIG. 18, as measured by plaque forming units (PFU), genomic copy (gc) and expression of the mCherry transgene, JΔNI8 exhibited more robust growth than JΔNI5. Furthermore, native HSV genes were observed to be expressed earlier during infection in complementing cells from JΔNI8 as opposed to JΔNI5 (FIG. 19, representing fold expression relative to each JDNI5 gene at 6 hpi arbitrarily assigned a value of 1).

As revealed in Table 9-1, JΔNI8 and JΔNI8GFP produced more plaques per genomic copy (gc) (on complementing cells) than JΔNI5 and JΔNI7GFP, respectively. This reveals that the ratio of functional over defective particles (a measure of quality) in JΔNI8 and JΔNI8GFP preparations is higher than in JΔNI5 and JΔNI7GFP preparations.

TABLE 9-1

| Virus | gc/ml | pfu/ml | gc/pfu |
|---|---|---|---|
| JΔNI5 #1 | 1.98E+11 | 8.33E+07 | 2.38E+03 |
| JΔNI5 #2 | 1.17E+12 | 5.00E+08 | 2.35E+03 |
| JΔNI7GFP | 3.99E+11 | 1.86E+08 | 2.14E+03 |
| JΔNI8 #1 | 3.72E+10 | 4.66E+07 | 7.99E+02 |
| JΔNI8 #2 | 5.56E+11 | 1.06E+09 | 5.24E+02 |
| JΔNI8GFP | 5.33E+11 | 8.33E+08 | 6.40E+02 |

Figure 21:
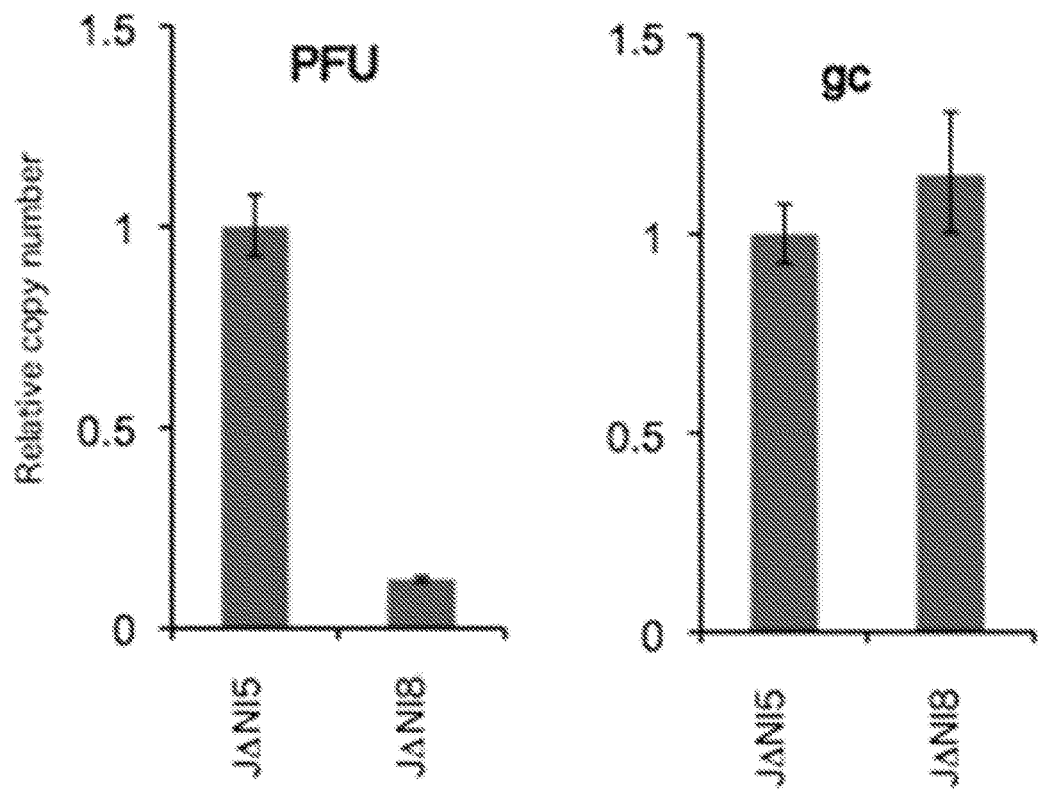
FIG. 21 presents data demonstrating that infection of human dermal fibroblast (HDF) cells with equal amounts of JΔNI8 and JΔNI5 (expressed as gc) results in equal amounts of viral DNA in the nucleus. Data are representative of two hours post infection (hpi).
Figure 22:
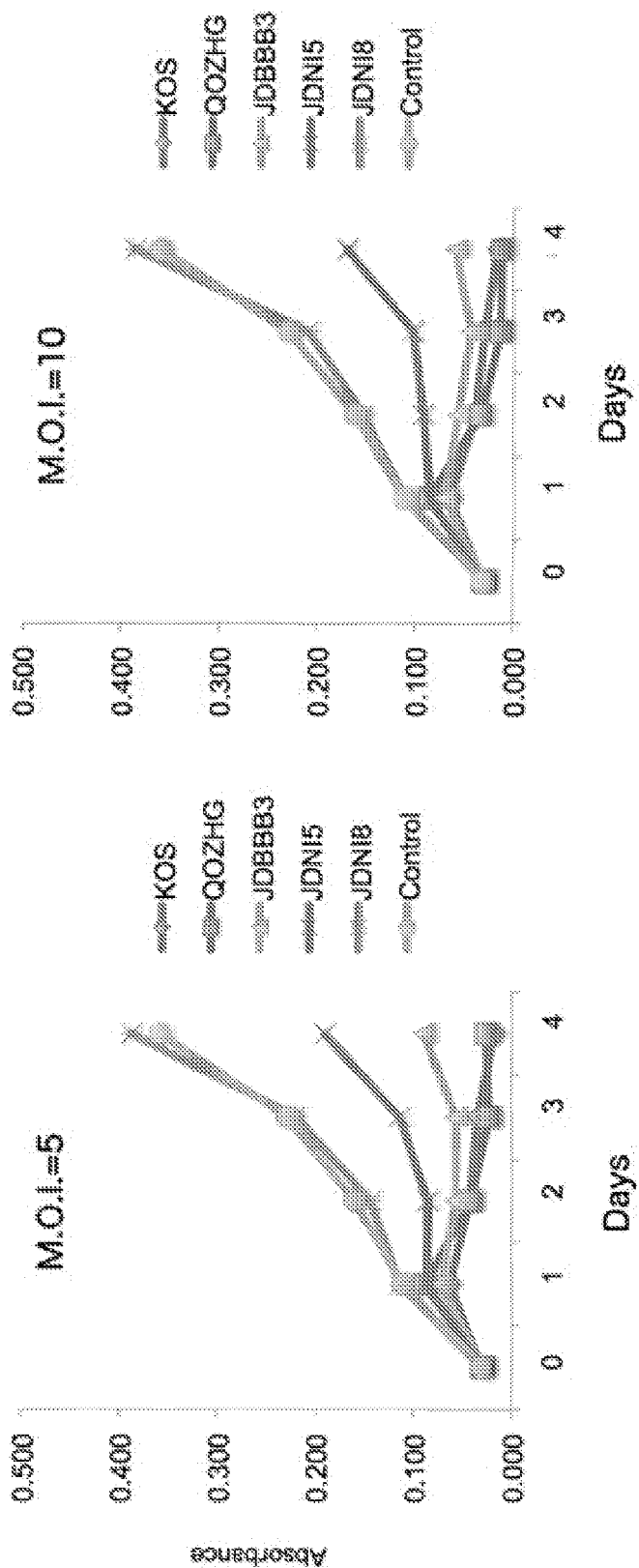
FIG. 22 presents data comparing the cell viability (MTT) of HDF infected with various HSV vectors at two M.O.I. The lower -X-line in each panel represents the results for JΔNI5, while the upper -X-line in each graph represents the results for JΔNI8.
Figure 23:
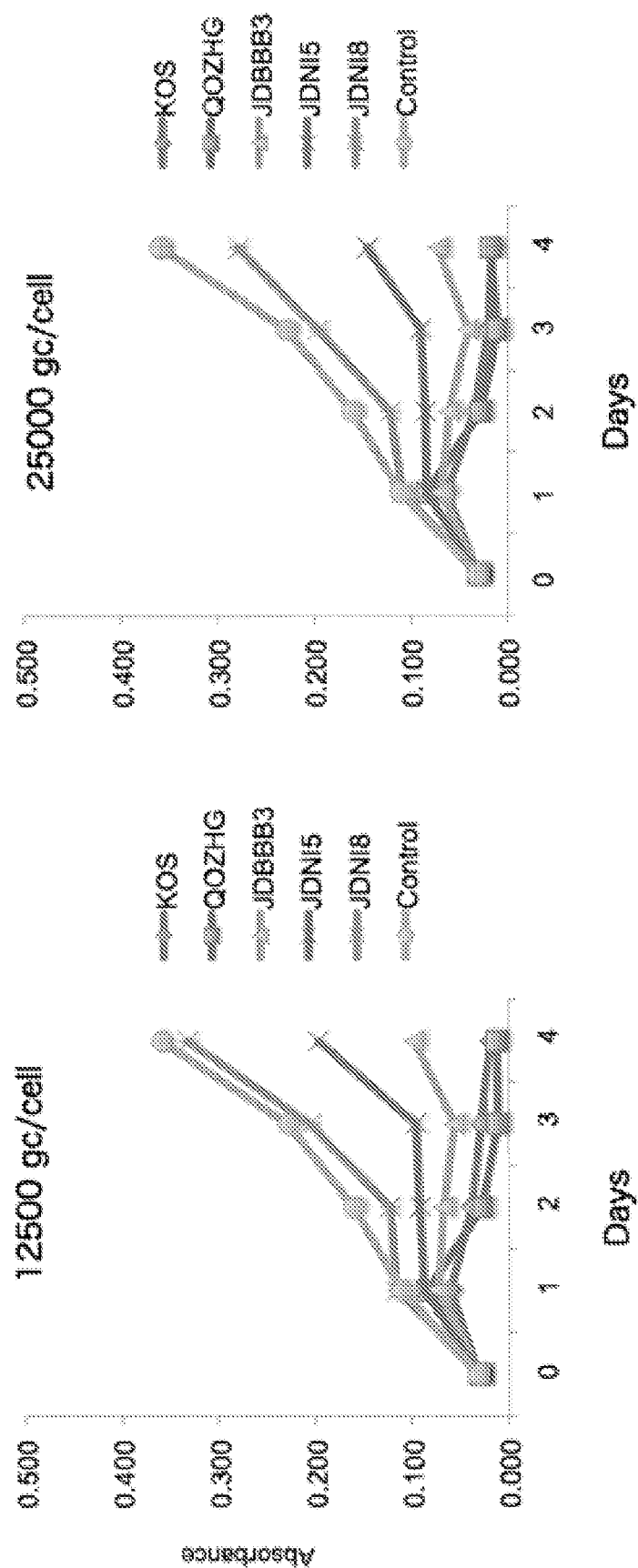
FIG. 23 presents data comparing the cell viability analysis (MTT) of HDF infected with various HSV vectors at different numbers of viral genomic copies per cell. For the left panel (12500 gc/cell), the M.O.I. of JΔNI5 was 5 PFU/cell, whereas the M.O.I. for JΔNI8 was 18 PFU/cell. For the right panel (25000 gc/cell), the M.O.I. of JΔNI5 was 11, whereas the M.O.I. for JΔNI8 was 33. The lower -X-line in each panel represents the results for JΔNI5, while the upper -X-line in each graph represents the results for JΔNI8.
Figure 24:
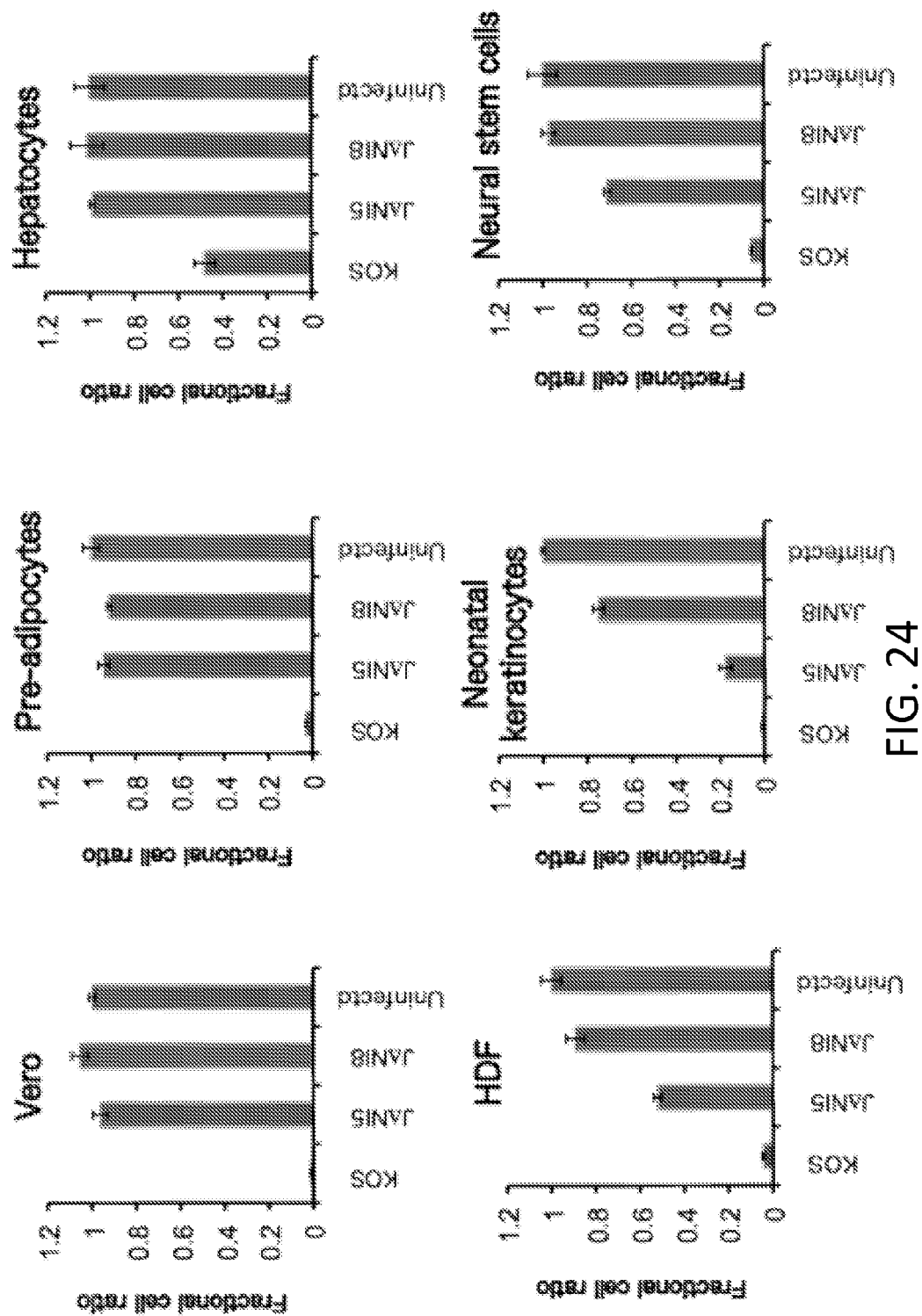
FIG. 24 presents data comparing the viability of cells infected with KOS, JΔNI5, and JΔNI8 in six cell types (HDF, human neonatal keratinocytes, human neural stem cells, Vero, human preadipocytes, and human hepatocytes). The MTT assay was conducted using 25,000 gc/cell, with data reported at 5 days post infection (dpi).

Also, it was observed that infection at equal levels of gc resulted in equal amounts of viral DNA in the nucleus of human dermal fibroblasts. However, using the protocol discussed in connection with FIG. 10, this was accomplished by much lower PFU for JΔNI8 vs. JΔNI5. (FIG. 21) These data reveal that infections at equal gc should be used for studies comparing JΔNI8 to JΔNI5 (or JΔNI7GFP vs JΔNI8GFP). MTT cell viability analysis (see FIG. 22) demonstrated that JΔNI8 (upper -X-line in each graph) was measurably less toxic (approaching or exceeding the viability of uninfected control cells) than any of the other vectors at 5 or 10 PFU/cell (M.O.I.=5 or =10). The lower -X-line in each graph represents the results for JΔNI5. These data also reveal that vectors that have an intact ICP0 gene, even under a β promoter (JΔBBB3 (also termed JDBBB3 or JAβββ3 or JDβββ3)) or without UL41 (QOZHG), are more toxic than JΔNI5 or JΔNI8. As expected, replicating virus (KOS) kills the cells. Additional MTT experiments using HDFs reveal that, although JΔNI8 showed slight toxicity at higher MOIs it was much less than JΔNI5 at 3-fold lower MOIs (equal gc/cell) (FIG. 23). Other MTT data revealed that JΔNI8 is less toxic than JΔNI5 in some (HDF, human neonatal keratinocytes, and human neural stem cells) but not all (Vero, human preadipocytes, and human hepatocytes) cell types (see FIG. 24).

Figure 25:
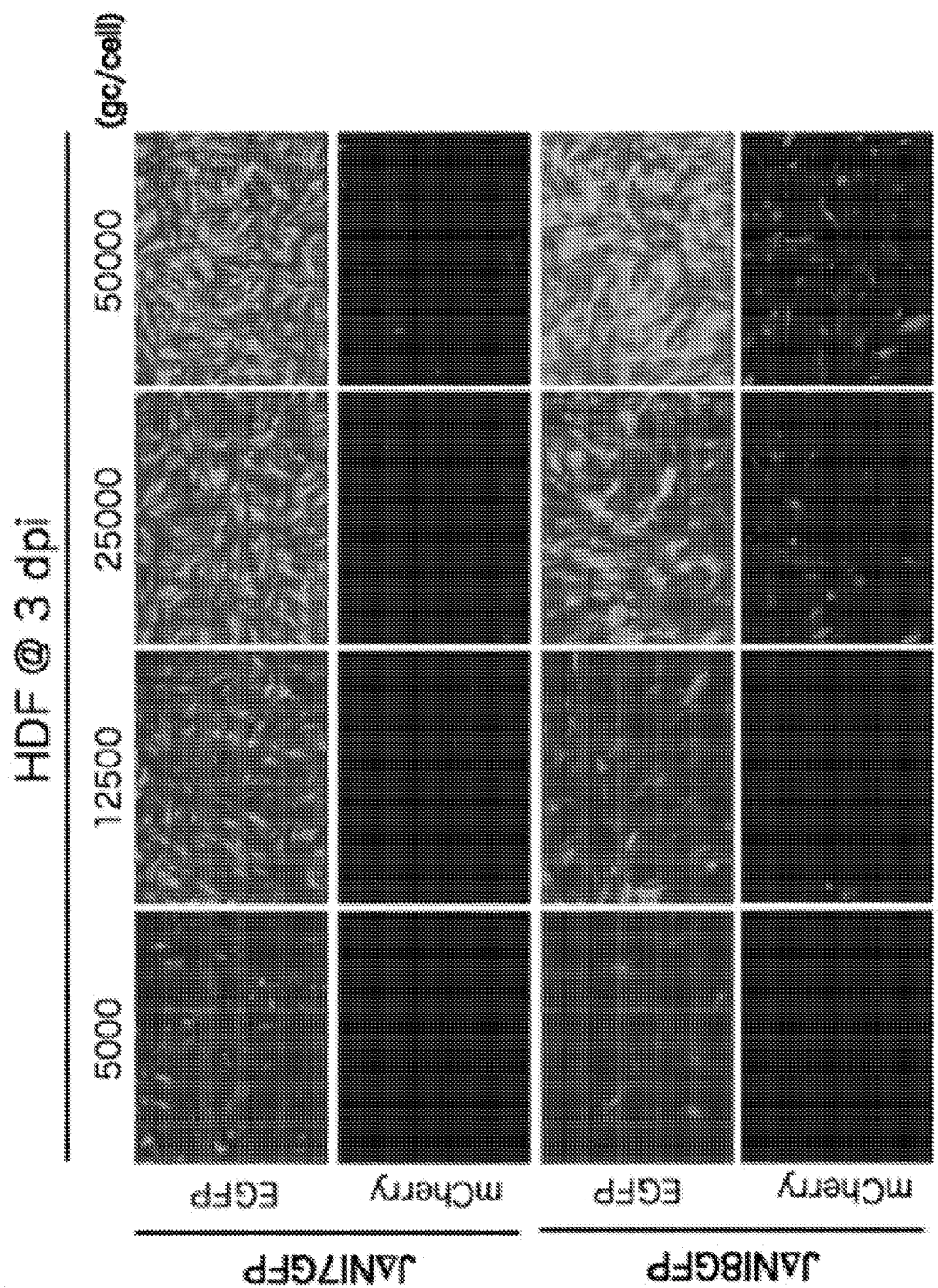
FIG. 25 presents dose-response data at three days post infection comparing reporter gene expression (mCherry or Enhanced Green Fluorescent Protein (EGFP)) between human dermal fibroblasts (HDF) infected at the indicated gc/cell with either JΔNI7GFP and JΔNI8GFP.
Figure 26:
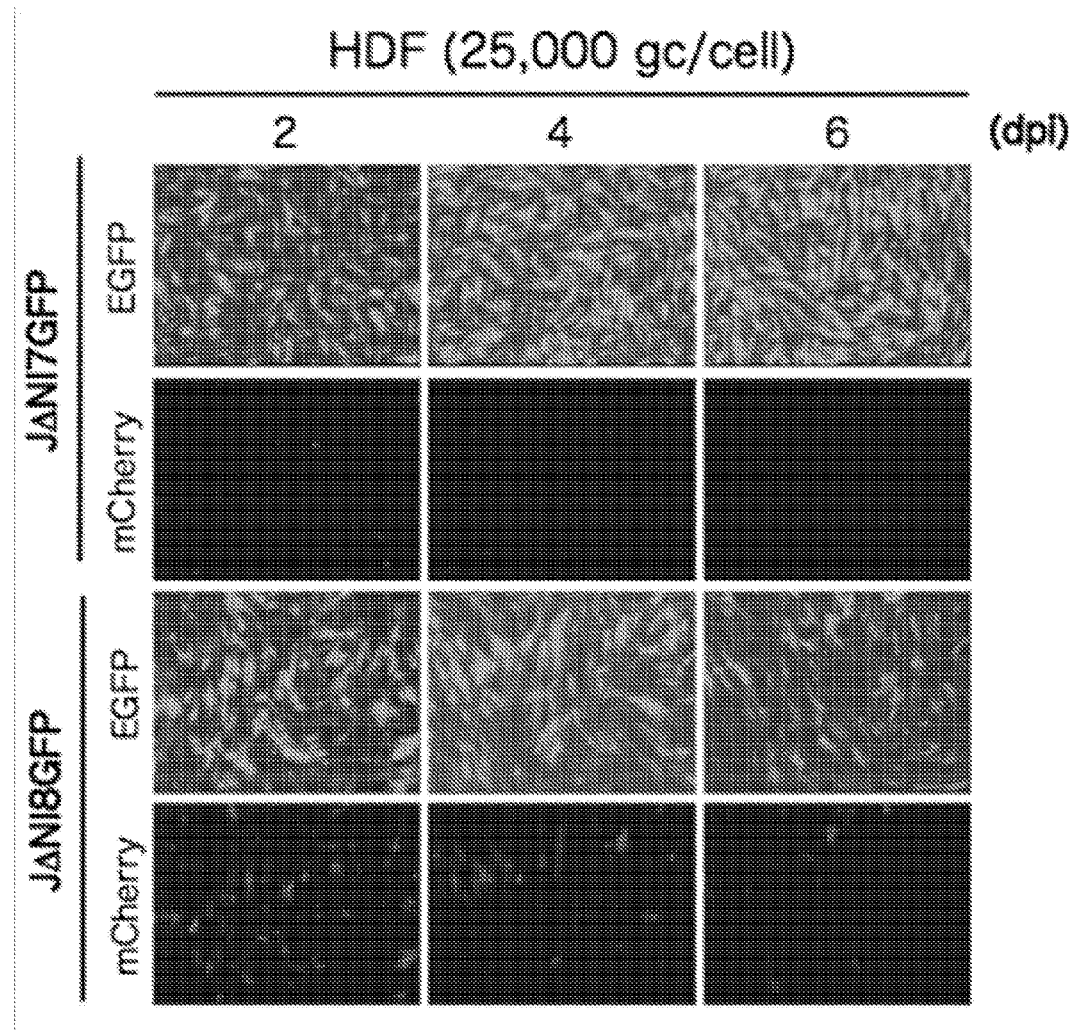
FIG. 26 presents time-course data comparing reporter gene expression (mCherry or EGFP) between human dermal fibroblasts (HDF) infected at 25,000 gc/cell with either JΔNI7GFP and JΔNI8GFP.

Reporter gene expression from both transgenes (i.e., EGFP and mCherry) present within JΔNI7GFP and JΔNI8GFP, respectively, were compared in HDF cells at 3 dpi. The results are presented in FIGS. 25 and 26. It was observed that GFP expression by JΔNI8GFP increased with dose (from 5000 to 50,000 gc/cell, FIG. 25), but leveled off for JΔNI7GFP. Without wishing to be bound by theory, it is believed that the leveling-off observed for expression from JΔNI7GFP may be attributed to high-dose toxicity of the vector in HDF cells, which implies that such toxicity is lower in JΔNI8GFP. Also, notable mCherry was observed from the HDF cells infected with JΔNI8GFP but not by HDF cells infected with JΔNI7GFP. Similar experiments were conducted with a constant dose of either JΔNI7GFP or JΔNI8GFP (25,000 gc/cell) with the level of EGFP or mCherry fluorescence assayed over time (2, 4, and 6 days post infection (FIG. 26)). Reporter signals in JΔNI8GFP-infected cultures decreased between 4 and 6 dpi, likely a result of viral genome dilution by unimpaired cell division. Signals were more stable in JΔNI7GFP-infected cultures, likely due to reduced cell division.

Figure 27:
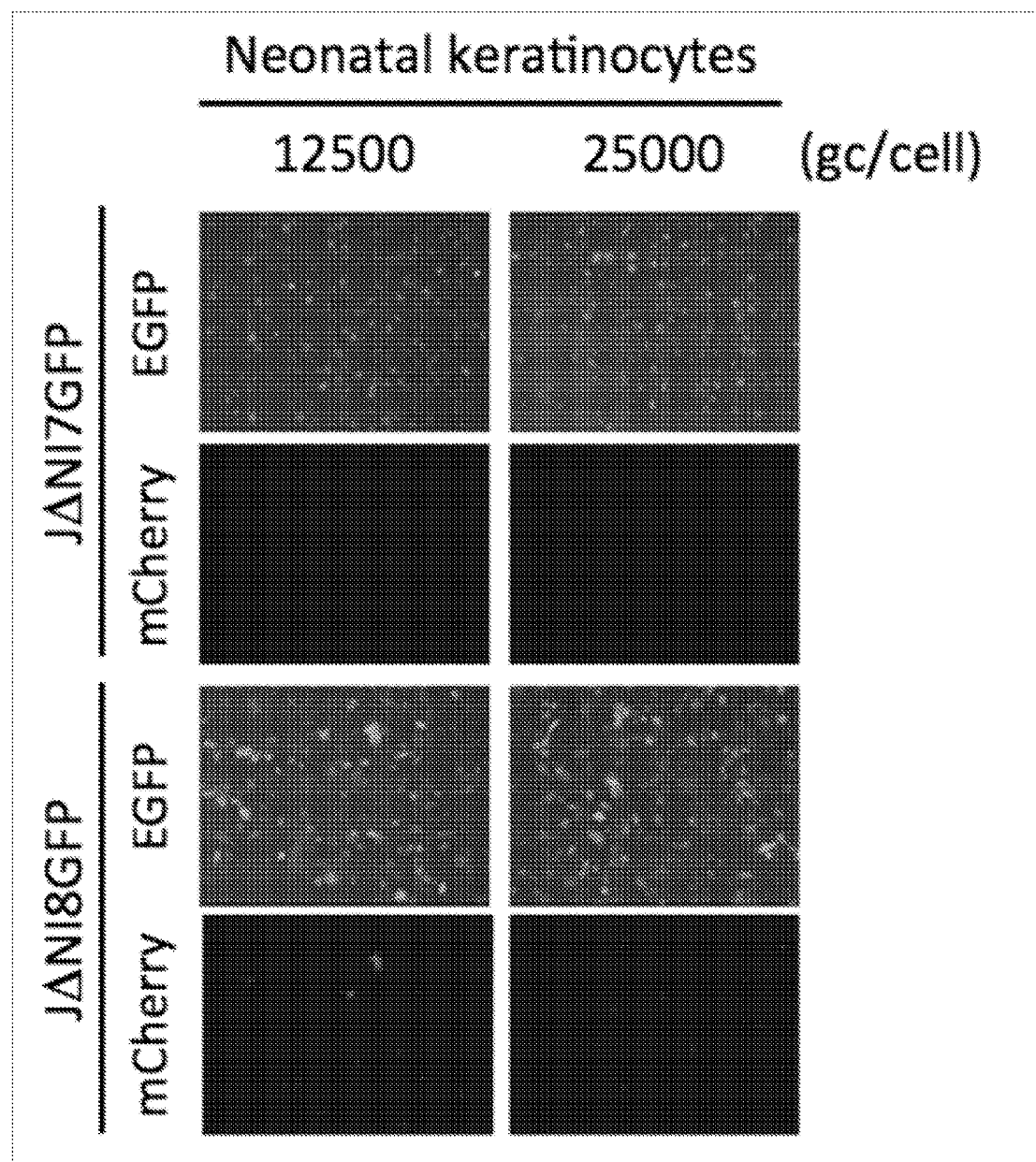
FIG. 27 presents the results of experiments comparing reporter gene expression (mCherry or EGFP) for human neonatal keratinocytes three days post infection with either 12,500 gc/cell or 25,000 gc/cell of either JΔNI7GFP or JΔNI8GFP.

Transgene (EGFP or mCherry) expression from other cells infected with either JΔNI7GFP vs. JΔNI8GFP also was investigated. As depicted in FIG. 27, at two measured doses (12,500 gc/cell and 25,000 gc/cell) JΔNI8GFP expressed more GFP in human neonatal keratinocytes than JΔNI7GFP.

Figure 28:
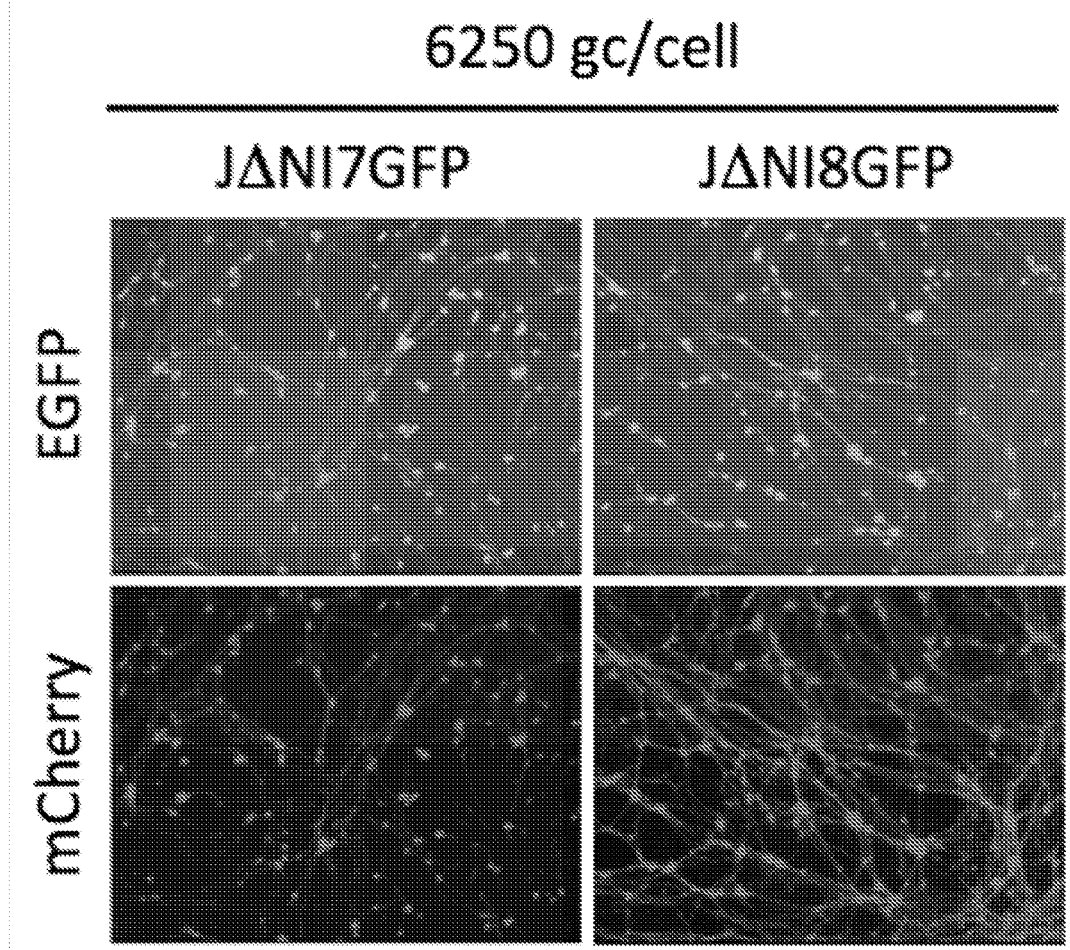
FIG. 28 presents the results of experiments comparing reporter gene expression (mCherry or EGFP) for rat dorsal root ganglion (DRG) neurons three days post infection with 6250 gc/cell of either JΔNI7GFP or JΔNI8GFP.

Also, transgene expression from rat dorsal root ganglion (DRG) cells infected with either either JΔNI7GFP or JΔNI8GFP (at 6250 gc/cell) was assayed. As depicted in FIG. 28, mCherry (inserted in the ICP4 deleted locus of both vectors) expression from JΔNI7GFP was enhanced in rat DRG neurons relative to GFP compared to non-neuronal cells, and relatively more in JΔNI8GFP- than in JΔNI7GFP-infected cells. These results reveal that JΔNI8 is non toxic and provides for transgene expression in neurons from both the LAT and the ICP4 locus.

Example 10

This example demonstrates in vivo expression from the JΔNI7-GFP vector in a long-term experiment.

Figure 29:
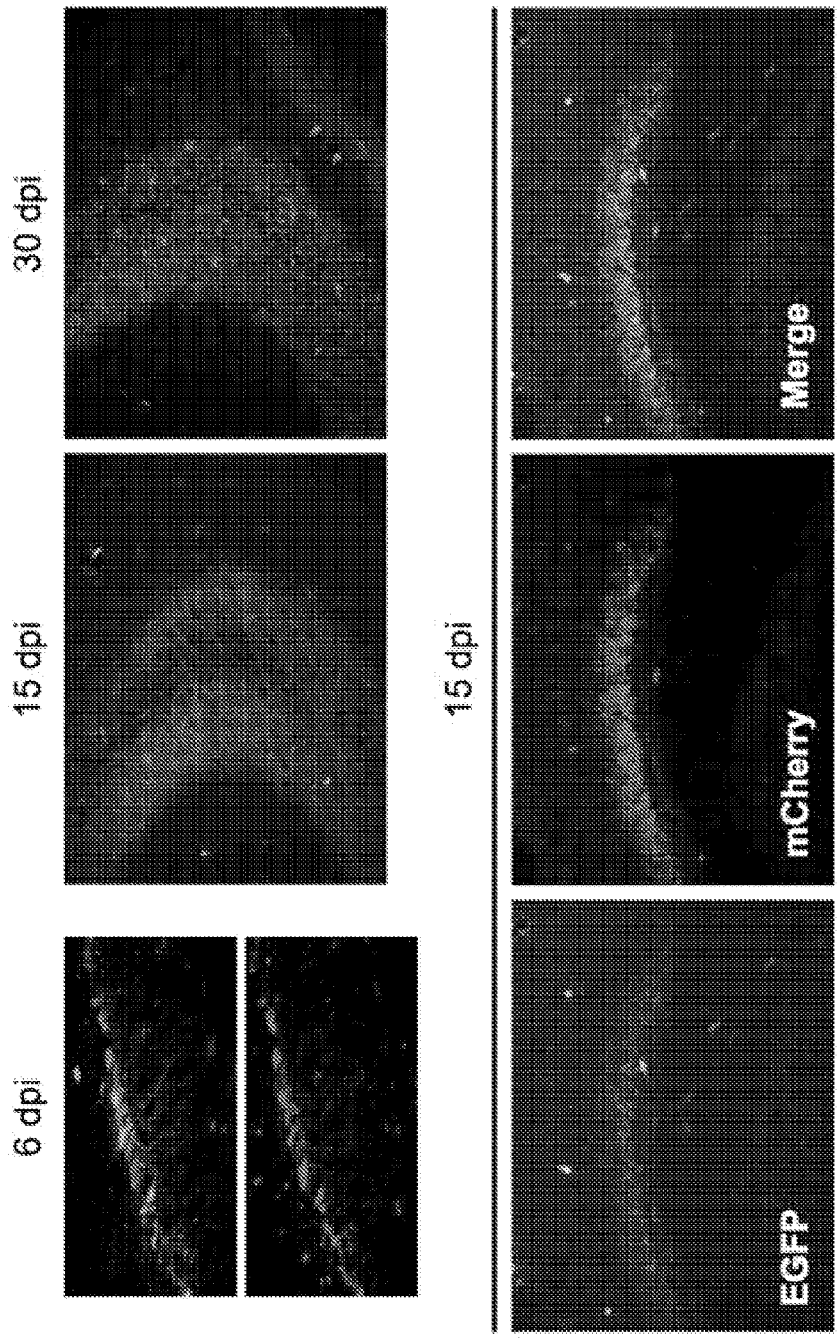
FIG. 29 presents the results of experiments investigating transgene expression (mCherry or EGFP) in neural cells infected with JΔNI7GFP. Top, separate (left; 40×) or merged (center, right; 20×) images of EGFP and mCherry fluorescence at the indicated days post infection (dpi); bottom, separate and merged images at 15 dpi (10×).

JDNI7-GFP ($8.0 \times 10^8$ genome copies/2 μl; $3.7 \times 10^5$ PFU) was sterotactically injected into the hippocampus of rats (AP: −1.8; ML: −1.7; P: +3.5) at a rate of 0.1 μl/min. Animals were euthanized and perfused at 6, 15 or 30 days post vector injection (dpi), and brain cryosections were imaged under a fluorescence microscope. FIG. 29 reveals robust expression of both EGFP and mCherry co-localized within the same cells within the hippocampus. In FIG. 29 top, separate (left; 40×) or merged (center, right; 20×) images of EGFP and mCherry fluorescence at the indicated days post infection (dpi); bottom, separate and merged images are depicted at 15 dpi (10×).

Example 11

This example relates to the expression of the mCherry transgene from the JΔNI7-GFP vector within infected primary astrocytes.

Mouse astrocytes were infected (M.O.I.=5) and cultured. After 25 days post infection, the cells were fixed and exposed to an antibody specific to glial fibrillary acidic protein (GFAP), positive binding of which identifies astrocytes. Immunofluorescence imaging revealed that JΔNI7-GFP is non toxic and provides for persistent expression in astrocytes.

Example 12

This example demonstrates the generation of a cell line for complementing the inventive HSV vectors and which also facilitates exision of a loxP-flanked BAC cassette during viral propagation.

The U2OS-ICP4/27 cell line discussed above was engineered to express Cre recombinase. The resulting cell line, U2OS-ICP4/27/Cre, complements the functions of all of the deficient HSV IE genes in vectors JDNI5, 7, 8 and their derivatives except that of the dispensable ICP47 gene, and removes the BAC cassette during virus growth.

Figure 30:
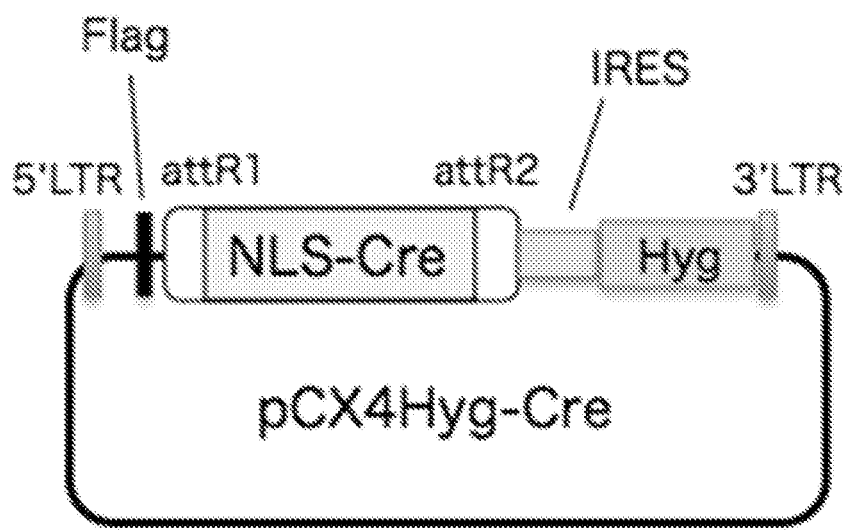
FIG. 30 is a schematic diagram of pCX4Hyg-Cre.
Figure 31:
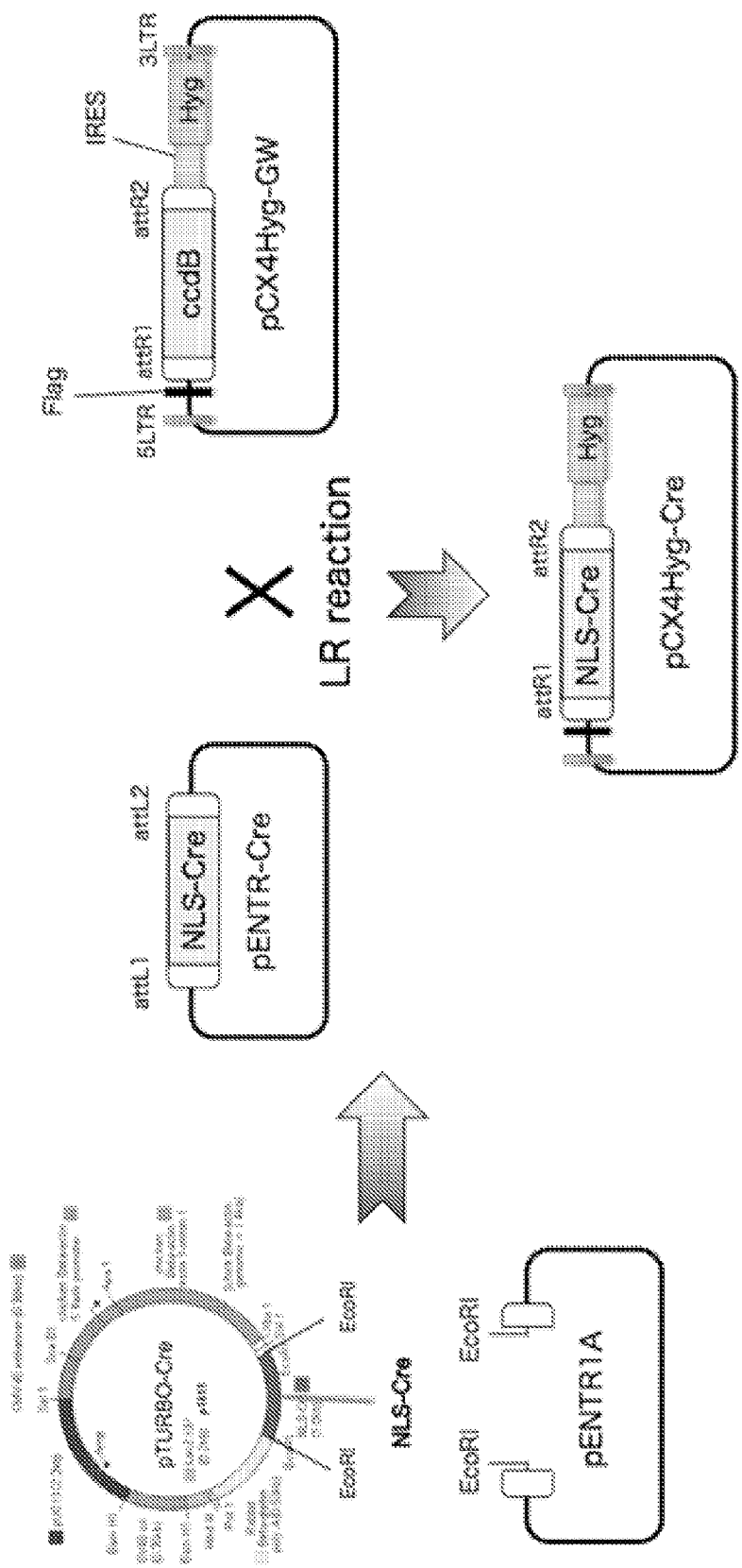
FIG. 31 is a schematic representation of the generation of pCX4Hyg-Cre.

U2OS-ICP4/27/Cre cells were generated by infection of U2OS-ICP4/27 cells with a Cre-expressing retroviral vector. For construction of the retroviral vector, plasmid pCX4Hyg (PNAS 2003, 100: 13567-13572; GenBank accession number AB086387) was modified by insertion of a Gateway recombination cassette into the multi cloning site to create pCX4Hyg-GW. The complete NLS-Cre coding sequence from plasmid pTurbo-Cre (GenBank accession number AF334827.1) was inserted between the attL1 and attL2 sites of pENTR1A (Invitrogen) and then transferred into pCX4Hyg-GW by LR Clonase-mediated Gateway recombination to create pCX4Hyg-Cre. This plasmid and its construction are schematically depicted in FIGS. 30 and 31. Retroviral particles were produced as described by Makino et al. (*Exp Cell Res* 2009, 315: 2727-2740). Briefly, pCX4Hyg-Cre was co-transfected with Gag-Pol and VSV-G expression plasmids into 293T cells and supernatant was collected 48 hours later, filtered through a 0.45 micron filter, and concentrated by centrifugation. Suitable Gag-Pol & VSV-G plasmids are commercially available (e.g., pCMV-Gag-Pol from Cell Biolabs (Cat. No. RV-111) and pCMV-VSV-G from Addgene).

U2OS-ICP4/27 cells were infected with the purified Cre retrovirus and cells were selected for resistance to puromycin, blasticidin and hygromycin. Resistant colonies were isolated, amplified, infected with JΔNI7-GFP at 0.001-1 PFU/cell, and stained for β-galactosidase activity at 2 days post infection (dpi). Clones showing few blue cells were found to undergo rapid cytopathic effect (100% CPE at 4 dpi after infection at MOI=0.01) whereas the parental U2OS-ICP4/27 cells showed plaque-forming clusters of blue cells and approximately 25% CPE at 9 dpi. These results indicated that Cre-mediated removal of the BAC elements along with the linked LacZ expression cassette in JΔNI7-GFP facilitated virus growth. Accurate removal of the BAC and LacZ sequences between the loxP sites of JΔN17-GFP has been confirmed by PCR on viral DNA from individual JΔNI7-GFP plaques on a selected U2OS-ICP4$^+$/27$^+$/Cre$^+$ clone.

It thus has been observed that passage through this U2OS-ICP4/27/Cre cell line removes the approximately 11 KB BAC sequence, recovering room for transgenes, and markedly accelerates virus growth.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and

The invention claimed is:

1. A cell for the production of a herpes simplex virus (HSV) vector, wherein the cell is a U2OS cell that comprises an expression cassette comprising the HSV ICP4 gene and an expression cassette comprising the HSV ICP27 gene, wherein the cell supports the production of infectious viral particles upon infection with an HSV that comprises an inactivating mutation in the HSV ICP0 gene, the HSV ICP4 gene, and the HSV ICP27 gene or the promoters thereof.

2. The cell according to claim 1, wherein the cell does not detectably express the HSV ICP0 gene.

3. The cell according to claim 1, wherein the expression cassette comprises an inducible promoter that is operably linked to the HSV ICP4 gene and an inducible promoter that is operably linked to the HSV ICP27 gene.

4. The cell according to claim 3, wherein one or more inducible promoter is active in the presence of VP16.

5. The cell according to claim 3, wherein one or more inducible promoter is active when the cell is infected with HSV.

6. The cell according to claim 3, wherein the inducible promoter that is operably linked to the ICP4 gene is the cognate viral promoter for the HSV ICP4 gene.

7. The cell according to claim 3, wherein the inducible promoter that is operably linked to the ICP27 gene is the cognate viral promoter for the HSV ICP27 gene.

8. The cell according to claim 1, wherein the cell comprises an HSV vector that comprises an inactivating mutation in the HSV ICP0 gene, the HSV ICP4 gene, and the HSV ICP27 gene or the promoters thereof.

9. A clonal population comprising a plurality of cells according to claim 1.

10. A system for the production of a herpes simplex virus (HSV) vector, the system comprising:

a) the cell according to claim 1, and
b) an HSV vector that comprises an inactivating mutation in the HSV ICP0 gene, the HSV ICP4 gene and the HSV ICP27 gene or the promoters thereof.

11. The system according to claim 10, wherein the HSV vector does not detectably express the HSV ICP22 gene as an immediate early gene.

12. The system according to claim 10, wherein the HSV vector does not detectably express the HSV ICP47 gene.

13. The system according to claim 10, wherein the HSV vector is does not detectably express the HSV UL41 gene.

* * * * *

SEQUENCE LISTING

<160> NUMBER OF SEQ ID NOS: 88

<210> SEQ ID NO 1
<211> LENGTH: 5730
<212> TYPE: DNA
<213> ORGANISM: Artificial Sequence
<220> FEATURE:
<223> OTHER INFORMATION: LAT-derived sequence

<400> SEQUENCE: 1

```
cacggcggcc accgccgccg ccgccgccga caccgcagag ccggcgcgcg cacacacaag      60
cggcagaggc agaaaggccc cgagtcattg tttatgtggc cgcgggccag cagacggccc     120
gcgacacccc cccccgcccg tgtgggtatc cggccccccg ccccgcgccg gtccattaag     180
ggcgcgcgtg cccgcgagat atcaatccgt taagtgctct gcagacaggg gcaccgcgcc     240
cggaaatcca ttaggccgca gacgaggaaa ataaaattac atcacctacc catgtggtgc     300
tgtggcctgt ttttgctgcg tcatctgagc ctttataaaa gcggggcgc ggccgtgccg      360 atcgccggtg gtgcgaaaga ctttccgggc gcgtccgggt gccgcggctc tccgggcccc     420
cctgcagccg gggcggccaa ggggcgtcgg cgacatcctc cccctaagcg ccggccggcc     480
gctggtctgt tttttcgttt tccccgtttc ggggtggtg ggggttgcgg tttctgtttc      540
tttaacccgt ctgggtgtt tttcgttccg tcgccggaat gtttcgttcg tctgtccct       600 cacggggcga aggccgcgta cggcccggga cgaggggccc ccgaccgcgg cggtccgggc     660
cccgtccgga cccgctcgcc ggcacgcgac gcgaaaaagg cccccggag gcttttccgg      720 gttcccggcc cggggcctga gatgaacact cggggttacc gccaacggcc ggcccccgtg     780
gcggcccggc ccggggcccc ggcggaccca aggggccccg gcccggggcc ccacaacggc     840
ccggcgcatg cgctgtggtt ttttttcct cggtgttctg ccgggctccg tcgcctttcc      900
tgttctcgct tctccccccc cccttcacc cccagtaccc tcctccctcc cttcctcccc      960
cgttatccca ctcgtcgagg gcgccccggt gtcgttcaac aaagacgccg cgtttccagg    1020
taggttagac acctgcttct ccccaataga ggggggggga cccaaacgac aggggcgcc     1080 ccagaggcta aggtcggcca cgccactcgc gggtgggctc gtgttacagc acaccagccc    1140
gttattttcc cccctccca cccttagtta gactctgtta cttaccgtc cgaccaccaa      1200 ctgccccctt atctaagggc cggctggaag accgccaggg ggtcggccgg tgtcgctgta    1260
accccccacg ccaatgaccc acgtactcca agaaggcatg tgtcccaccc cgcctgtgtt    1320
tttgtgcctg gctctctatg cttgggtctt actgcctggg ggggggagt gcgggggagg     1380 gggggggtgt ggaaggaaat gcacggcgcg tgtgtacccc ccctaaagtt tgtcctaaag    1440
cgaggatatg gaggagtggc gggtgccggg ggaccggggt gatctctggc acgcggggt     1500 gggaagggtc gggggagggg gggatgggt accggcccac ctggccggcg cgggtgcgcg     1560
tgcctttgca caccaacccc acgtcccccg gcggtctcta agaaacaccg cccccccctcc    1620 ttcataccac cgagcatgcc tggtgtggg ttggtaacca acacgcccat cccctcgtct     1680
cctgtgattc tctggctgca ccgcattctt gttttctaac tatgttcctg tttctgtctc    1740 ccccccacc cctccgcccc accccccaac acccacgtct gtgggcgtta cataacttac     1800
ggtaaatggc ccgcctggct gaccgccaa cgaccccgc ccattgacgt caataatgac      1860
```

```
gtatgttccc atagtaacgc aataggggac tttccattga cgtcaatggg tggagtattt    1920
acggtaaact gcccacttgg cagtacatca agtgtatcat atgccaagta cgcccctat     1980
tgacgtcaat gacggtaaat ggcccgcctg gcattatgcc cagtacatga ccttatggga    2040
ctttcctact tggcagtaca tctacgtatt agtcatcgct attaccatgg tcgaggtgag    2100
ccccacgttc tgcttcactc tccccatctc ccccccctcc ccacccccaa ttttgtattt    2160
atttattttt taattatttt gtgcagcgat ggggggcgggg gggggggggg aaaaagcgaa   2220
gcgcgcggcg ggcgggagtc gctgcgcgct gccttcgccc cgtgccccgc tccgcgccgc    2280
ctcgcgccgc ccgccccggc tctgactgac gcgttactcc cacaggtga gcgggcggga    2340
cggcccttct cctccgggct gtaattagcg cttggtttaa tgacggcttg tttcttttct    2400
gtggctgcgt gaaagccttg aggggctccg ggagggccct ttgtgcgggg ggagcggctc    2460
gggggggtgcg tgcgtgtgtg tgtgcgtggg gagcgccgcg tgcggctccg cgctgccgg    2520
cggctgtgag cgctgcgggc gcggcgcggg gctttgtgcg ctccgcagtg tgcgcgaggg    2580
gagcgcggcc gggggcggtg ccccgcgtg cgggggggggc tgcgagggga acaaaggctg    2640
cgtgcgggt gtgtgcgtgg ggggtgagc aggggtgtg ggcgcgtcgg tcgggctgca      2700
acccccctg cacccccctc cccgagttgc tgagcacggc ccggcttcgg gtgcgggct      2760
ccgtacgggg cgtggcgcgg ggctcgccgt gccgggcggg gggtggcggc aggtgggggt    2820
gccgggcggg gcggggccgc ctcgggccgg ggagggctcg ggggagggg gcggcggccc    2880
ccggagcgcc ggcggctgtc gaggcgcggc gagccgcagc cattgccttt tatggtaatc    2940
gtgcgagagg gcgcagggac ttcctttgtc ccaaatctgt gcggagccga aatctgggag    3000
gcgccgccgc acccctcta gcgggcgcgg ggcgaagcgg tgcggcgccg gcaggaagga    3060
aatgggcggg gagggcttc gtgcgtcgcc gcgccgccgt ccccttctcc ctctccagcc    3120
tcggggctgt ccgcggggggg acggctgcct tcggggggga cggggcaggg cggggttcgg    3180
cttctggcgt gtgaccggcg gctctagagc ctctgctaac catgttcatg ccttcttctt    3240
tttcctacag ctcctgggca acgtgctggt tattgtgctg tctcatcatt ttggcaaaga    3300
attcgagctc ggctaccggt cgccaccatg gtgagcaagg gcgaggagct gttcaccggg    3360
gtggtgccca tcctggtcga gctggacggc gacgtaaacg gccacaagtt cagcgtgtcc    3420
ggcgagggcg agggcgatgc cacctacggc aagctgaccc tgaagttcat ctgcaccacc    3480
ggcaagctgc ccgtgccctg gcccaccctc gtgaccaccc tgacctacgg cgtgcagtgc    3540
ttcagccgct accccgacca catgaagcag cacgacttct tcaagtccgc catgcccgaa    3600
ggctacgtcc aggagcgcac catcttcttc aaggacgacg gcaactacaa gacccgcgcc    3660
gaggtgaagt tcgagggcga cacctggtg aaccgcatcg agctgaaggg catcgacttc    3720
aaggaggacg gcaacatcct ggggcacaag ctggagtaca actacaacag ccacaacgtc    3780
tatatcatgg ccgacaagca gaagaacggc atcaaggtga acttcaagat ccgccacaac    3840
atcgaggacg gcagcgtgca gctcgccgac cactaccagc agaacacccc catcggcgac    3900
ggccccgtgc tgctgcccga caaccactac ctgagcaccc agtccgccct gagcaaagac    3960
cccaacgaga agcgcgatca catggtcctg ctggagttcg tgaccgccgc cgggatcact    4020
ctcggcatgg acgagctgta caagtccgga ctcagatctt ttccctctg ccaaaaatta    4080
tggggacatc atgaagcccc ttgagcatct gacttctggc taataaagga aatttatttt    4140
cattgcaata gtgtgttgga attttttgtg tctctcactc ggaaggacat atgggagggc    4200
aaatcattta aaacatcaga atgagtattt ggtttagagt ttggcaacat atgcccatat    4260
```

```
gctggctgcc atgaacaaag gttggctata aagaggtcat cagtatatga aacagccccc    4320
tgctgtccat tccttattcc atagaaaagc cttgacttga ggttagattt tttttatatt    4380
ttgttttgtg ttattttttt ctttaacatc cctaaaattt tccttacatg ttttactagc    4440
cagatttttc ctcctctcct gactactccc agtcatagct gtccctcttc tcttatggag    4500
atccctcgac ctgcagccca agcttggcgt aatcatggtc atagctgttt cctgtgtgaa    4560
attgttatcc gctcacaatt ccacacaaca tacgagccgg aagcataaag tgtaaagcct    4620
ggggtgccta atgagtgagc taactcacat taattgcgtt gcgctcactg cccgctttcc    4680
agtcgggaaa cctgtcgtgc cagcggatcc gcatctcaat tagtcagcaa ccatagtccc    4740
gcccctaact ccgcccatcc cgcccctaac tccgcccagt tccgcccatt ctccgcccca    4800
tggctgacta ttttttttta tttatgcaga ggccgaggcc gcctcggcct ctgagctatt    4860
ccagaagtag tgaggaggct ttttggagg cctaggcttt tgcaaaaagc taacttgttt    4920
attgcagctt aaattgccag tggcaggatg ctttcgggga tcggtggtca ggcagcccgg    4980
gccgcggctc tgtggttaac accagagcct gcccaacatg caccccccac tcccacgcac    5040
ccccactccc acgcaccccc actcccacgc accccactc ccacgcaccc ccactcccac    5100 gcaccccac tcccacgcac cccactccc acgcacccc actcccacgc accccactc    5160 ccacgcaccc ccactcccac gcaccccac tcccacgcac cccactccc acgcaccccc    5220 actcccacgc accccactc ccacgcaccc ccactcccac gcaccccgc gatacatcca    5280 acacagacag ggaaaagata caaagtaaa ccttttattc caacagaca gcaaaaatcc    5340 cctgagtttt ttttattagg gccaacacaa agacccgct ggtgtgtggt gcccgtgtct    5400 ttcactttc ccctccccga cacggattgg ctggtgtagt gggcgcggcc agagaccacc    5460
cagcgcccgc aattggatat cggggcccgc ggtaccgtcg actgcagaat tcgaagcttg    5520
agctcgagat ctgcggcacg ctgttgacgc tgttaagcgg gtcgctgcag ggtcgctcgg    5580
tgttcgaggc cacacgcgtc accttaatat gcgaagtgga cctgggaccg cgccgccccg    5640
actgcatctg cgtgttcgaa ttcgccaatg acaagacgct gggcggggtt tgtgtcatca    5700
tagaactaaa gacatgcaaa tatatttctt                                     5730
```

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2

```
gcggcggaaa atagcctttg                                                  20
```

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3

```
gatcacacgt tccacctcat c                                                21
```

<210> SEQ ID NO 4
<211> LENGTH: 24
<212> TYPE: DNA

```
<213> ORGANISM: Artificial Sequence
<220> FEATURE:
<223> OTHER INFORMATION: primer

<400> SEQUENCE: 4
atcatggccg acaagcagaa gaac                                              24

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
gtacagctcg tccatgccga gagt                                              24

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
cctgtcccct cagttcatgt                                                   20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gcttcaagta gtcggggatg                                                   20

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
accaccatga cgacgactc                                                    19

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
agccccgtct cgaacagt                                                     18

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
cgtgtgcaag cttccttgt                                                    19
```

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
tctcgagatt actaagatca cactcc                                          26

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
tctcgagatt actaagatca cactcc                                          26

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
aaaacaggga gttgcaataa aaa                                             23

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
atggggtggc tccagaac                                                   18

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
ctgccggtga tgaaggag                                                   18

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
gtaacctcca cgcccaact                                                  19

<210> SEQ ID NO 17
<211> LENGTH: 19
<212> TYPE: DNA
<213> ORGANISM: Artificial Sequence
<220> FEATURE:

<223> OTHER INFORMATION: primer

<400> SEQUENCE: 17
agcagcagcg aacaagaag        19

<210> SEQ ID NO 18
<211> LENGTH: 18
<212> TYPE: DNA
<213> ORGANISM: Artificial Sequence
<220> FEATURE:
<223> OTHER INFORMATION: primer

<400> SEQUENCE: 18
atgggcctct cgttctcc         18

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
cggtgatgag gacgttgtt        19

<210> SEQ ID NO 20
<211> LENGTH: 18
<212> TYPE: DNA
<213> ORGANISM: Artificial Sequence
<220> FEATURE:
<223> OTHER INFORMATION: primer

<400> SEQUENCE: 20
tcatcttcga ccgccatc         18

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
tgctgcccat aaggtatcg        19

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gtcagcacct tcatcgacct       20

<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23 caggggaca aactcgtg          18

```
<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
agctgcagat cgaggactg                                                19

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ccatcatctc ctcgcttagg                                               20

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
gtctgctcta cgacctgtcc a                                             21

<210> SEQ ID NO 27
<211> LENGTH: 19
<212> TYPE: DNA
<213> ORGANISM: Artificial Sequence
<220> FEATURE:
<223> OTHER INFORMATION: primer

<400> SEQUENCE: 27
aaccgagcga aaacaggag                                                19

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
tccatcccaa taacacctac g                                             21

<210> SEQ ID NO 29
<211> LENGTH: 18
<212> TYPE: DNA
<213> ORGANISM: Artificial Sequence
<220> FEATURE:
<223> OTHER INFORMATION: primer

<400> SEQUENCE: 29
ggggtccagt gacattcg                                                 18

<210> SEQ ID NO 30
<211> LENGTH: 18
<212> TYPE: DNA
<213> ORGANISM: Artificial Sequence
<220> FEATURE:
<223> OTHER INFORMATION: primer
```

<400> SEQUENCE: 30
gagggtcagc cgttcaag                                                 18

<210> SEQ ID NO 31
<211> LENGTH: 18
<212> TYPE: DNA
<213> ORGANISM: Artificial Sequence
<220> FEATURE:
<223> OTHER INFORMATION: primer

<400> SEQUENCE: 31
aactccacgg ggttacgc                                                 18

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
gcgctctctc gtttcttcc                                                19

<210> SEQ ID NO 33
<211> LENGTH: 18
<212> TYPE: DNA
<213> ORGANISM: Artificial Sequence
<220> FEATURE:
<223> OTHER INFORMATION: primer

<400> SEQUENCE: 33
ggccaacacg gttcgata                                                 18

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
caatctggga agcgtgaatc                                               20

<210> SEQ ID NO 35
<211> LENGTH: 18
<212> TYPE: DNA
<213> ORGANISM: Artificial Sequence
<220> FEATURE:
<223> OTHER INFORMATION: primer

<400> SEQUENCE: 35
cgcccaaagt caaacgtc                                                 18

<210> SEQ ID NO 36
<211> LENGTH: 18
<212> TYPE: DNA
<213> ORGANISM: Artificial Sequence
<220> FEATURE:
<223> OTHER INFORMATION: primer

<400> SEQUENCE: 36
ccacaggagg cctacacg                                                 18

<210> SEQ ID NO 37
<211> LENGTH: 20

```
<212> TYPE: DNA
<213> ORGANISM: Artificial Sequence
<220> FEATURE:
<223> OTHER INFORMATION: primer

<400> SEQUENCE: 37
ctgaaacttc tcggggatca                                          20

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
ccccgctgga actactatga ca                                       22

<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
gcatcaggaa ccccaggtt                                           19

<210> SEQ ID NO 40
<211> LENGTH: 20
<212> TYPE: DNA
<213> ORGANISM: Artificial Sequence
<220> FEATURE:
<223> OTHER INFORMATION: probe has a 5' "FAM" and a 3' "TAMRA"

<400> SEQUENCE: 40
ttcagcgccg tcagcgagga                                          20

<210> SEQ ID NO 41
<211> LENGTH: 90
<212> TYPE: DNA
<213> ORGANISM: Artificial Sequence
<220> FEATURE:
<223> OTHER INFORMATION: primer

<400> SEQUENCE: 41
cccgatatcc aattgcgggc gctgggtggt ctctggccgc gcccactaca ccagccaatc    60
cgtgtaggat gacgacgata agtagggata                                    90

<210> SEQ ID NO 42
<211> LENGTH: 67
<212> TYPE: DNA
<213> ORGANISM: Artificial Sequence
<220> FEATURE:
<223> OTHER INFORMATION: primer

<400> SEQUENCE: 42
gatctcgagc tcaagcttcg aattctgcag tcgacggtac cgcgggcccc gatatccaat    60
tgcgggc                                                             67

<210> SEQ ID NO 43
<211> LENGTH: 75
<212> TYPE: DNA
<213> ORGANISM: Artificial Sequence
<220> FEATURE:
```

<223> OTHER INFORMATION: primer

<400> SEQUENCE: 43
acacggattg gctggtgtag tgggcgcggc cagagaccac ccagcgcccg caaccaatta     60
accaattctg attag                                                     75

<210> SEQ ID NO 44
<211> LENGTH: 84
<212> TYPE: DNA
<213> ORGANISM: Artificial Sequence
<220> FEATURE:
<223> OTHER INFORMATION: primer

<400> SEQUENCE: 44
tatggatccc ggacctggtt aaccacccgc cggtcctacg cgaactggag gataagcgca     60
ggatgacgac gataagtagg gata                                           84

<210> SEQ ID NO 45
<211> LENGTH: 84
<212> TYPE: DNA
<213> ORGANISM: Artificial Sequence
<220> FEATURE:
<223> OTHER INFORMATION: primer

<400> SEQUENCE: 45
caggaattcg cgcttatcct ccagttcgcg taggaccggc gggtggttaa ccaggtccgc     60
aaccaattaa ccaattctga ttag                                           84

<210> SEQ ID NO 46
<211> LENGTH: 81
<212> TYPE: DNA
<213> ORGANISM: Artificial Sequence
<220> FEATURE:
<223> OTHER INFORMATION: primer

<400> SEQUENCE: 46
gggccctgga aatggcggac accttcctgg acaccatgcg ggttgggccc aggatgacga     60
cgataagtag ggataacagg g                                              81

<210> SEQ ID NO 47
<211> LENGTH: 75
<212> TYPE: DNA
<213> ORGANISM: Artificial Sequence
<220> FEATURE:
<223> OTHER INFORMATION: primer

<400> SEQUENCE: 47
gggcccaacc cgcatggtgt ccaggaaggt gtccgccatt tccagggccc caaccaatta     60
accaattctg attag                                                     75

<210> SEQ ID NO 48
<211> LENGTH: 73
<212> TYPE: DNA
<213> ORGANISM: Artificial Sequence
<220> FEATURE:
<223> OTHER INFORMATION: primer

<400> SEQUENCE: 48
tttataaccc cgggggtcat tcccaacgat cacatgcaat ctaactggct gggccctgga     60
aatggcggac acc                                                       73

```
<210> SEQ ID NO 49
<211> LENGTH: 75
<212> TYPE: DNA
<213> ORGANISM: Artificial Sequence
<220> FEATURE:
<223> OTHER INFORMATION: primer

<400> SEQUENCE: 49
tatggatccc cgcggatggt gagcaagggc gaggaggata acatggccat cataggatga      60
cgacgataag taggg                                                      75

<210> SEQ ID NO 50
<211> LENGTH: 43
<212> TYPE: DNA
<213> ORGANISM: Artificial Sequence
<220> FEATURE:
<223> OTHER INFORMATION: primer

<400> SEQUENCE: 50
aatctgcagg gatccctaca accaattaac caattctgat tag                       43

<210> SEQ ID NO 51
<211> LENGTH: 75
<212> TYPE: DNA
<213> ORGANISM: Artificial Sequence
<220> FEATURE:
<223> OTHER INFORMATION: primer

<400> SEQUENCE: 51
cttggggcgg tcccgcccgc cggccaatgg gggggcggca aggcgggcgg tggcggccgc      60
tctagaagat ctggc                                                      75

<210> SEQ ID NO 52
<211> LENGTH: 75
<212> TYPE: DNA
<213> ORGANISM: Artificial Sequence
<220> FEATURE:
<223> OTHER INFORMATION: primer

<400> SEQUENCE: 52
ccgcgggggg cccgggctgc acaggtgaa accaacagag cacggcgcac gctgggtacc       60
gggccccccc tcgag                                                      75

<210> SEQ ID NO 53
<211> LENGTH: 75
<212> TYPE: DNA
<213> ORGANISM: Artificial Sequence
<220> FEATURE:
<223> OTHER INFORMATION: primer

<400> SEQUENCE: 53
cctcactgcc cgtcgcgcgt gtttgatgtt aataataac acataaattt tggcggccgc       60
tctagaagat ctggc                                                      75

<210> SEQ ID NO 54
<211> LENGTH: 75
<212> TYPE: DNA
<213> ORGANISM: Artificial Sequence
<220> FEATURE:
<223> OTHER INFORMATION: primer

<400> SEQUENCE: 54
ccgacactga aatgccccccc ccccttgcg ggcggtccat taaagacaac gctgggtacc      60
```

```
gggcccccccc tcgag                                                          75
```

<210> SEQ ID NO 55
<211> LENGTH: 81
<212> TYPE: DNA
<213> ORGANISM: Artificial Sequence
<220> FEATURE:
<223> OTHER INFORMATION: primer

<400> SEQUENCE: 55

```
tattacgtat tagtcatcgc tattaccatg gtcgaggtga gccccacgtt ctgcttagga         60
tgacgacgat aagtagggat a                                                   81
```

<210> SEQ ID NO 56
<211> LENGTH: 43
<212> TYPE: DNA
<213> ORGANISM: Artificial Sequence
<220> FEATURE:
<223> OTHER INFORMATION: primer

<400> SEQUENCE: 56

```
aatctgcagt acgtactaca accaattaac caattctgat tag                           43
```

<210> SEQ ID NO 57
<211> LENGTH: 36
<212> TYPE: DNA
<213> ORGANISM: Artificial Sequence
<220> FEATURE:
<223> OTHER INFORMATION: primer

<400> SEQUENCE: 57

```
gcaattggct ctgccccgcc gtccccgtgt tcgtcc                                   36
```

<210> SEQ ID NO 58
<211> LENGTH: 75
<212> TYPE: DNA
<213> ORGANISM: Artificial Sequence
<220> FEATURE:
<223> OTHER INFORMATION: primer

<400> SEQUENCE: 58

```
tttttgcaaa agcctaggcc tccaataact agtcaataat caatgtcgac ttatttatta         60
acatcaaaca cgcgc                                                          75
```

<210> SEQ ID NO 59
<211> LENGTH: 36
<212> TYPE: DNA
<213> ORGANISM: Artificial Sequence
<220> FEATURE:
<223> OTHER INFORMATION: primer

<400> SEQUENCE: 59

```
gcacgcgtag aggtgctgcg ggagattcaa ctgagc                                   36
```

<210> SEQ ID NO 60
<211> LENGTH: 75
<212> TYPE: DNA
<213> ORGANISM: Artificial Sequence
<220> FEATURE:
<223> OTHER INFORMATION: primer

<400> SEQUENCE: 60

```
tattgactag ttattggagg cctaggcttt tgcaaaaaag cttataatgg gtctttaatg         60
gaccgcccgc aaggg                                                          75
```

<210> SEQ ID NO 61
<211> LENGTH: 75
<212> TYPE: DNA
<213> ORGANISM: Artificial Sequence
<220> FEATURE:
<223> OTHER INFORMATION: primer

<400> SEQUENCE: 61
tattacgtac aaccacatac agcgccatgt caacgatatg ttgggccgcg ttgaggatga    60
cgacgataag taggg    75

<210> SEQ ID NO 62
<211> LENGTH: 43
<212> TYPE: DNA
<213> ORGANISM: Artificial Sequence
<220> FEATURE:
<223> OTHER INFORMATION: primer

<400> SEQUENCE: 62
aatctgcagt acgtactaca accaattaac caattctgat tag    43

<210> SEQ ID NO 63
<211> LENGTH: 80
<212> TYPE: DNA
<213> ORGANISM: Artificial Sequence
<220> FEATURE:
<223> OTHER INFORMATION: primer

<400> SEQUENCE: 63
tatacccgtg acacccgacg ctgggggggcg tggctgccgg gaggggccgc gtatgaggat    60
gacgacgata agtagggata    80

<210> SEQ ID NO 64
<211> LENGTH: 70
<212> TYPE: DNA
<213> ORGANISM: Artificial Sequence
<220> FEATURE:
<223> OTHER INFORMATION: primer

<400> SEQUENCE: 64
ccacacaagc cccgtatccc cgttcccgcg cttttcgttg gtttatatac ccgtgacacc    60
cgacgctggg    70

<210> SEQ ID NO 65
<211> LENGTH: 75
<212> TYPE: DNA
<213> ORGANISM: Artificial Sequence
<220> FEATURE:
<223> OTHER INFORMATION: primer

<400> SEQUENCE: 65
catacgcggc ccctcccggc agccacgccc cccagcgtcg ggtgtcacgg caaccaatta    60
accaattctg attag    75

<210> SEQ ID NO 66
<211> LENGTH: 75
<212> TYPE: DNA
<213> ORGANISM: Artificial Sequence
<220> FEATURE:
<223> OTHER INFORMATION: primer

<400> SEQUENCE: 66

```
catacgcggc ccctcccggc agccacgccc cccagcgtcg ggtgtcacgg caaccaatta    60
accaattctg attag                                                   75

<210> SEQ ID NO 67
<211> LENGTH: 70
<212> TYPE: DNA
<213> ORGANISM: Artificial Sequence
<220> FEATURE:
<223> OTHER INFORMATION: primer

<400> SEQUENCE: 67
gtcaggcagc ccgggccgcg gctctgtggt taacaccaga gcctgcccaa tccaacacag    60
acagggaaaa                                                         70

<210> SEQ ID NO 68
<211> LENGTH: 75
<212> TYPE: DNA
<213> ORGANISM: Artificial Sequence
<220> FEATURE:
<223> OTHER INFORMATION: primer

<400> SEQUENCE: 68
tgttgggaaa taaaggttta cttttgtatc ttttccctgt ctgtgttgga caaccaatta    60
accaattctg attag                                                   75

<210> SEQ ID NO 69
<211> LENGTH: 80
<212> TYPE: DNA
<213> ORGANISM: Artificial Sequence
<220> FEATURE:
<223> OTHER INFORMATION: primer

<400> SEQUENCE: 69
cagatagtaa tcaattacgg ggtcattagt tcatagccca tatatggagt tccaggatga    60
cgacgataag tagggataac                                              80

<210> SEQ ID NO 70
<211> LENGTH: 70
<212> TYPE: DNA
<213> ORGANISM: Artificial Sequence
<220> FEATURE:
<223> OTHER INFORMATION: primer

<400> SEQUENCE: 70
agactttccg ggcgcgtccg ggtgccgcgg ctctccgggc cccctgcag atagtaatca    60 attacggggt                                                         70

<210> SEQ ID NO 71
<211> LENGTH: 75
<212> TYPE: DNA
<213> ORGANISM: Artificial Sequence
<220> FEATURE:
<223> OTHER INFORMATION: primer

<400> SEQUENCE: 71
ggaactccat atatgggcta tgaactaatg accccgtaat tgattactat caaccaatta    60
accaattctg attag                                                   75

<210> SEQ ID NO 72
<211> LENGTH: 43
<212> TYPE: DNA
<213> ORGANISM: Artificial Sequence
```

```
<220> FEATURE:
<223> OTHER INFORMATION: primer

<400> SEQUENCE: 72
tgacaattga ctagttatac aagtttgtac aaaaaagctg aac                    43

<210> SEQ ID NO 73
<211> LENGTH: 46
<212> TYPE: DNA
<213> ORGANISM: Artificial Sequence
<220> FEATURE:
<223> OTHER INFORMATION: primer

<400> SEQUENCE: 73
ccattataac aattgagatc tccactttgt acaagaaagc tgaacg                 46

<210> SEQ ID NO 74
<211> LENGTH: 75
<212> TYPE: DNA
<213> ORGANISM: Artificial Sequence
<220> FEATURE:
<223> OTHER INFORMATION: primer

<400> SEQUENCE: 74
cggacccaaa ataataaaca cacaatcacg tgcgataaaa agaacacgcg acaagtttgt  60
acaaaaaagc tgaac                                                   75

<210> SEQ ID NO 75
<211> LENGTH: 75
<212> TYPE: DNA
<213> ORGANISM: Artificial Sequence
<220> FEATURE:
<223> OTHER INFORMATION: primer

<400> SEQUENCE: 75
cctgtttgtc gacgagattt aataaaaata accaaaaaca ccacagggga ccactttgta  60
caagaaagct gaacg                                                   75

<210> SEQ ID NO 76
<211> LENGTH: 75
<212> TYPE: DNA
<213> ORGANISM: Artificial Sequence
<220> FEATURE:
<223> OTHER INFORMATION: primer

<400> SEQUENCE: 76
aaacgtttgt atctcatctt tcctgtgtgt agttgtttct gttggatgcc atatcacaag  60
tttgtacaaa aaagc                                                   75

<210> SEQ ID NO 77
<211> LENGTH: 75
<212> TYPE: DNA
<213> ORGANISM: Artificial Sequence
<220> FEATURE:
<223> OTHER INFORMATION: primer

<400> SEQUENCE: 77
tgcgtgtttt catccaaccc gtgtgttctg tgtttgtggg atggaggggc cgagaaacgt  60
aaaatgatat aaata                                                   75

<210> SEQ ID NO 78
<211> LENGTH: 75
<212> TYPE: DNA
```

```
<213> ORGANISM: Artificial Sequence
<220> FEATURE:
<223> OTHER INFORMATION: primer

<400> SEQUENCE: 78
ccggggacac cgccagcaaa cgcgagcaac gggccacggg gatgaagcag aggatgacga    60
cgataagtag ggata                                                    75

<210> SEQ ID NO 79
<211> LENGTH: 75
<212> TYPE: DNA
<213> ORGANISM: Artificial Sequence
<220> FEATURE:
<223> OTHER INFORMATION: primer

<400> SEQUENCE: 79
ccacacaagc cccgtatccc cgttcccgcg cttttcgttg gtttatatac ccggggacac    60
cgccagcaaa cgcga                                                    75

<210> SEQ ID NO 80
<211> LENGTH: 75
<212> TYPE: DNA
<213> ORGANISM: Artificial Sequence
<220> FEATURE:
<223> OTHER INFORMATION: primer

<400> SEQUENCE: 80
ctgcttcatc cccgtggccc gttgctcgcg tttgctggcg gtgtccccgg caaccaatta    60
accaattctg attag                                                    75

<210> SEQ ID NO 81
<211> LENGTH: 31
<212> TYPE: DNA
<213> ORGANISM: Artificial Sequence
<220> FEATURE:
<223> OTHER INFORMATION: primer

<400> SEQUENCE: 81
cccggccaac cagcgtccgc cgagtcttcg g                                  31

<210> SEQ ID NO 82
<211> LENGTH: 30
<212> TYPE: DNA
<213> ORGANISM: Artificial Sequence
<220> FEATURE:
<223> OTHER INFORMATION: primer

<400> SEQUENCE: 82
gccggttcca gtgtaagggt cggggtccc                                     30

<210> SEQ ID NO 83
<211> LENGTH: 20
<212> TYPE: DNA
<213> ORGANISM: Artificial Sequence
<220> FEATURE:
<223> OTHER INFORMATION: primer

<400> SEQUENCE: 83
cctgacagag ctgtattgta                                               20

<210> SEQ ID NO 84
<211> LENGTH: 21
<212> TYPE: DNA
<213> ORGANISM: Artificial Sequence
```

```
<220> FEATURE:
<223> OTHER INFORMATION: primer

<400> SEQUENCE: 84
agatcgctgt cggagaggtc c                                            21

<210> SEQ ID NO 85
<211> LENGTH: 75
<212> TYPE: DNA
<213> ORGANISM: Artificial Sequence
<220> FEATURE:
<223> OTHER INFORMATION: primer

<400> SEQUENCE: 85
tatagatctc gagctcaagc ttcgaattct gcagtcgacg gtaccgcggg cccaggatga   60
cgacgataag taggg                                                   75

<210> SEQ ID NO 86
<211> LENGTH: 43
<212> TYPE: DNA
<213> ORGANISM: Artificial Sequence
<220> FEATURE:
<223> OTHER INFORMATION: primer

<400> SEQUENCE: 86
aatctgcaga gatctctaca accaattaac caattctgat tag                    43

<210> SEQ ID NO 87
<211> LENGTH: 75
<212> TYPE: DNA
<213> ORGANISM: Artificial Sequence
<220> FEATURE:
<223> OTHER INFORMATION: primer

<400> SEQUENCE: 87
tatgttaaca acaacaattg cattcatttt atgtttcagg ttcagggga ggtaggatga    60 cgacgataag taggg                                                   75

<210> SEQ ID NO 88
<211> LENGTH: 43
<212> TYPE: DNA
<213> ORGANISM: Artificial Sequence
<220> FEATURE:
<223> OTHER INFORMATION: primer

<400> SEQUENCE: 88
aatctgcagg ttaacctaca accaattaac caattctgat tag                    43
```